(12) United States Patent
Van Roosmalen et al.

(10) Patent No.: US 11,270,782 B2
(45) Date of Patent: Mar. 8, 2022

(54) DIAGNOSTIC METHOD EMPLOYING HNL

(71) Applicant: KONINKLIJKE PHILIPS N.V., Eindhoven (NL)

(72) Inventors: Markus Hendrikus Van Roosmalen, Berkel-Enschot (NL); Veronique Semjonow, Suresnes (FR); Jeroen Hans Nieuwenhuis, Waalre (NL); Per Venge, Uppsala (SE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/528,141

(22) PCT Filed: Nov. 19, 2015

(86) PCT No.: PCT/EP2015/077045
§ 371 (c)(1),
(2) Date: May 19, 2017

(87) PCT Pub. No.: WO2016/079219
PCT Pub. Date: May 26, 2016

(65) Prior Publication Data
US 2017/0356921 A1 Dec. 14, 2017

(30) Foreign Application Priority Data

Nov. 19, 2014 (EP) .................................. 14193886

(51) Int. Cl.
*G16H 10/40* (2018.01)
*C07K 16/18* (2006.01)
(Continued)

(52) U.S. Cl.
CPC ............. *G16H 10/40* (2018.01); *C07K 16/18* (2013.01); *G01N 33/56911* (2013.01);
(Continued)

(58) Field of Classification Search
CPC ....... G01N 33/6893; G01N 2333/4703; G01N 2800/26; C07K 16/18; C07K 2317/34;
(Continued)

(56) References Cited

U.S. PATENT DOCUMENTS

| 535,968 A | 3/1895 | Ware |
| 3,850,752 A | 11/1974 | Schuurs et al. |

(Continued)

FOREIGN PATENT DOCUMENTS

| EP | 404097 A2 | 6/1990 |
| EP | 0756708 B1 | 7/2001 |

(Continued)

OTHER PUBLICATIONS

Human NGAL ELISA Kit http://www.piercenet.com/product/human-ngal-elisa-kits, Available in web on Dec. 4, 2013.
(Continued)

*Primary Examiner* — Jana A Hines

(57) ABSTRACT

The present invention relates to the means and methods for the detection of bacterial infections, methods discriminating between viral and bacterial infections, methods of stratifying patients for subsequent treatment and further diagnostic purposes and methods to monitor antibiotherapy. The present invention is based on the detection of specific epitopes of human neutrophil lipocalin (HNL) using specific binding agents.

7 Claims, 8 Drawing Sheets

Specification includes a Sequence Listing.

(51) Int. Cl.
G01N 33/569 (2006.01)
G01N 33/68 (2006.01)
G16H 50/20 (2018.01)

(52) U.S. Cl.
CPC ..... *G01N 33/6893* (2013.01); *C07K 2317/34* (2013.01); *C07K 2317/51* (2013.01); *C07K 2317/515* (2013.01); *G01N 2333/4703* (2013.01); *G01N 2800/26* (2013.01); *G01N 2800/56* (2013.01); *G16H 50/20* (2018.01); *Y02A 90/10* (2018.01)

(58) Field of Classification Search
CPC .......... C07K 2317/51; C07K 2317/515; G16H 50/201; G06F 19/325
See application file for complete search history.

(56) References Cited

U.S. PATENT DOCUMENTS

| | | |
|---|---|---|
| 3,901,654 A | 8/1975 | Gross |
| 3,935,074 A | 1/1976 | Leute |
| 3,984,533 A | 10/1976 | Uzgiris |
| 3,996,345 A | 12/1976 | Schwarzberg |
| 4,034,074 A | 7/1977 | Miles |
| 4,098,876 A | 7/1978 | Piasio |
| RE30,985 E | 6/1982 | Cartaya |
| 4,376,110 A | 3/1983 | David |
| 4,452,901 A | 6/1984 | Gordon |
| 4,560,655 A | 12/1985 | Baker |
| 4,657,866 A | 4/1987 | Kumar |
| 4,767,704 A | 8/1988 | Cleveland |
| 4,927,762 A | 5/1990 | Darfler |
| 5,122,469 A | 6/1992 | Mather |
| 5,591,828 A | 1/1997 | Behringwerke |
| 6,306,393 B1 | 10/2001 | Goldenberg |
| 2002/0199213 A1 | 12/2002 | Ed |
| 2003/0031667 A1 | 2/2003 | Deo |
| 2003/0194404 A1 | 10/2003 | Corvalan |
| 2004/0115728 A1 | 6/2004 | Villanueva |
| 2005/0003742 A1 | 1/2005 | Makoto |
| 2005/0013604 A1 | 1/2005 | Ogawa |
| 2013/0072580 A1 | 3/2013 | Barasch |
| 2017/0144333 A1 | 5/2017 | Coquel et al. |

FOREIGN PATENT DOCUMENTS

| | | | |
|---|---|---|---|
| WO | 1987000195 A1 | 1/1987 | |
| WO | 1990003430 A1 | 4/1990 | |
| WO | 199110741 A1 | 7/1991 | |
| WO | 1991017271 A1 | 11/1991 | |
| WO | 1992001047 A1 | 1/1992 | |
| WO | 1993011161 A1 | 6/1993 | |
| WO | 1993011236 A1 | 6/1993 | |
| WO | 1993019172 A1 | 9/1993 | |
| WO | 1995015388 A1 | 6/1995 | |
| WO | 1995029404 A1 | 11/1995 | |
| WO | 199634096 A1 | 10/1996 | |
| WO | 1998024893 A2 | 6/1998 | |
| WO | 1998025965 A1 | 6/1998 | |
| WO | 2006066587 A1 | 6/2006 | |
| WO | 2008049330 A1 | 5/2008 | |
| WO | 2008072156 A2 | 6/2008 | |
| WO | 2008102218 A1 | 8/2008 | |
| WO | 2009052390 A1 | 4/2009 | |
| WO | WO 2009/052390 | * 4/2009 | ............. C07K 14/49 |
| WO | 2010033963 A2 | 3/2010 | |
| WO | 2010035204 A1 | 4/2010 | |
| WO | 2011036638 A1 | 3/2011 | |
| WO | 2013117746 A1 | 8/2013 | |
| WO | 2013132347 A2 | 9/2013 | |
| WO | 2014006408 A1 | 1/2014 | |

OTHER PUBLICATIONS

Sandwich ELISA http://www.abcam.com/index.html?pageconfig=resource&rid=11422 Available in Web on Dec. 4, 2013.
Cai, Linjun et al "The Origin of Multiple Molecular Forms in Urine of HNL/NGAL", Clinical Journal of American Society Nephrol. Dec. 2010, vol. 5, No. 12, pp. 2229-2235.
http://www.who.int/mediacentre/factsheets/fs194/en/; Antimicrobial Resistance—Fact Sheet No. 194, Apr. 2014.
Xu et al: "Lipocalins as Biochemical Markers of Disease"; Biochima et Biophysics Acta, 1482 92000), pp. 298-307.
Olejniczak et al: "Rapid Determination of Antigenic Epitopes in Human NGAL Using NMR"; Biopolymers, vol. 93, No. 7, pp. 657-667.
Al-Lazikani, Bissan et al "Standard Conformations for the Canonical Structures of Immunoglobulins", Journal Molecular Biology, 1997, vol. 273, pp. 927-948.
Bhatnagar, Pradip K. et al "Structure-Activity Relationships of NOvel Hematoregulatory Peptides", Journal Medical Chemistry, 1996, vol. 39, pp. 3814-3819.
Bich, Claudia et al "Reactivity and Applications of New Amine Reactive Cross-Linkers for Mass Spectrometric Detection of Protein-Protein Complexes" Anal. Chem., 2010, vol. 82, pp. 172-179.
Bird, Robert E. et al "Single-Chain Antigen-Binding Proteins", Science, Oct. 21, 1988, vol. 242.
"Detection of High Molecular Weight Forms of Platelet-Derived Growth Factor by Sequence-Specific Antisera", Science, vol. 226, No. 4675, Nov. 1984.
Brooks, D.A. et al "Human Lymphocyte Markers defined by antibodies derived from somatic cell hybrids", Clin. Exp. Immunol. 1980, vol. 39, pp. 477-485.
Brown, Joseph P. et al "Protein Antigens of Normal and Malignant Human Cells Identified by Immunoprecipitation with Monoclonal Antibodies", The Journal of Biolocal Chemistry, vol. 255, No. 11, Jun. 1980. pp. 4980-4983.
Bruggemann, Marianne et al "Production of Human Antibody Repertoires in Transgenic Mice", Current Opinion in Biotechnology, 1997, vol. 8, pp. 455-458.
Caton, Andrew J. et al "Influenza virus hemagglutinin-specific antibodies isolated from a combinatorial expression library are closely related to the immune response of the donor", Proceddings National Academy of Science, vol. 87, pp. 6450-6454, Aug. 1990.
Chothia, Cyrus et al "Conformations of Immunoglobulin Hypervariable Regions", Nature, vol. 342, Dec. 1989.
Chothia, Cyrus et al, "Canonical Structures for the Hypervariable Regions of Immunoglobulins", Journal of Molecular Biology, vol. 196, pp. 901-917, 1987.
Clothia, Cyrus et al, "Structural Repertoire of the Human Vh Segments", Ournal of Molecular Biology, vol. 227, pp. 799-817, 1982.
Chowdhury, Partha S. "Targeting Random Mutations to Hotspots in Antibody Variable Domains for Affinity Improvement", Methods in Molecular Biology, vol. 178, 2000.
Co, M.S. et al "A Humanized Antibody Specific for the Platelet Integrin gpIIb/IIIa", The Journal of Immunology, 1994, vol. 152, pp. 2968-2976.
Cook, Nancy R. "Use and Misuse of the Receiver Operating Characteristic Curve in Risk Prediction", Circulation, 2007.
Cortez-Retamozo, Vima et al "Efficient Cancer Therapy with a Nanobody-Based Conjugate", Cancer Research, vol. 64, Apr. 2004, pp. 2853-2857.
Cunningham, Brian C. et al. "High-Resolution Epitope Mapping of hGH-Receptor Interactions by Alanine-Scanning Mutagenesis", Science, vol. 244, 1989.
Cuthbertson, Alan S. et al "Design of Low Molecular Weight Hematoregulatory Agents from the Structure-Activity Relationship of a Dimeric Pentapeptide", Journal Medical Chemistry, vol. 40, pp. 2876-2882. 1997.
D'Agostino, Ralph B. et al "Validation of the Framingham Coronary Heart Disease Prediction Scores", American Medical Association, vol. 286, No. 2, Jul. 2011.
Dall'acqua, William et al "Contribution of Domain Interface Residues to the Stability of Antibody CH3 Domain Homodimers" Biochemistry, vol. 37, pp. 9266-9273, 1998.

(56) References Cited

OTHER PUBLICATIONS

Daugherty, Patrick S. etal "Quantitative Analysis of the Effect of the Mutation Frequency on the Affinity Maturation of Single Chain Fv Antibodies", PNAS, vol. 97, No. 5, pp. 2029-2034, 2000.

Desmyter, Aline et al "Antigen Specificty and High Affinity Binding Provided by One Single Loop of a Camel Single-Domain Antibody", The Journal of Biological Chemistry, vol. 276, No. 28, pp. 26285-26290, 2001.

Ewert, Stefan et al "Biophysical Properties of Camelid VHH Domains compared to those of Human VH3 Domains", Biochemistry, vol. 41, p. 3628-3636, 2002.

Fermer, Christian et al Specificity Rescue and Affinity Maturation of a Low-Affinity IgM Antibody Against Pro-Gastrin-Releasing Peptide using Phage Display and DNA Shuffling, Tumor Biology, vol. 25, pp. 7-13, 2004.

Graham, F.L. et al Characteristics of a Human Cell Line Transformed by DNA from Human Adenovirus Type 5, Journal Gen. Virol., vol. 36, pp. 59-72, 1977.

Gruber, M. et al Efficient Tumor Cell Lysis Mediated by a Bispecific Single Chain Antibody Expressed in *Escherichia coli*. Journal Immunology, vol. 152, pp. 5368-5374, 1994.

Guss, Bengt et al Structure of the IgG-Binding Regions of Streptococcal Protein G, The EMBO Journal, vol. 5, No. 7, pp. 1567-1575, 1986.

Hawkins, Robert E. et al "Selection of Phage Antibodies by Binding Affinity Mimicking Affinity Maturation", Journal of Molecular Biology, vol. 226, pp. 889-896. 1992.

Holliger, Philipp et al "Diabodies": Small Bivalent and Bispecific Antibody Fragments, Oroc. National Academy of Science, vol. 90, pp. 6444-6448, Jul. 1993.

Huls, Gerwin et al Tumor Cell Killing by in Vitro Affinity-Matured Recombinant Human Monoclonal Antibodies Cancer Immunology Immunother, vol. 50, pp. 163-171, 2001.

Juston, James S. et al "Protein Engineering of Antibody Binding Sites: Recovery of Specific Activity in an Anti-Digoxin Single-Chain Fv Analogue proceded in *Escherichia coli*", Proc. National Academy of Science, vol. 85, pp. 5879=5883, 1988.

Jakovobits, Aya et al "Analysis of Homozygous Mutant Chimeric mice: Deletion of the immunoglobulin heavy-chain joining region blocks B-cell development and antibody production", Proc. National Academy of Science, vol. 90, pp. 2551-2555, 1993.

Jakovobits, Aya, et al "Germ-Line Transmission and Expression of a Human Derived Yeast Artificial Chromosome", Letters to Nature, vol. 362, 1993.

Jermutus, Lutz et al "Tailoring in vitro evolution for protein affinity or stability", PNAS, vol. 98, No. 1, pp. 75-80, 2001.

Jones, Peter T. etal "Replacing the complementairty-determining regions in a human antibody with those from a mouse", Nature, vol. 321, May 1986.

Kettleborough, C.A. et al "Humanization of a mouse monoclonal antibody by CDR-graftng: the importance of framework residues on loop conformation", Protein Engineering, vol. 4, No. 7, pp. 773-783. 1991.

Kleldsen, Lars et al "Isolation and Primary Structure of NGAL, a Novel Protein Associated with Human Neutrophil Gelatinase", The Journal of Biological Chemistry, vO. 268, No. 14, pp. 10425-10432, 1993.

Lefranc, Marie-Paule et al IMGT, the international ImMunoGeneTics database, Nucleic Acids Research, vol. 27, No. 1, pp. 209-212, 1999.

Lindmark, Roger et al "Binding of Immunoglobulins to Protein A and Immunoglobulin Levels in Mammalian Sera", Journal of Immunological Methods, vol. 62, pp. 1-13, 1983.

Low, Nigel M. et al "Mimicking SOmatic Hypermutation: Affinity Maturation of Antibodies Displayed on Bacteriophage using a Bacterial Mutator Strain", Journal of Molecular Biology, vol. 260, pp. 359-368, 1996.

Lowman, H.B. "Bacteriophage Display and Discover of Peptide Leads for Drug Development", Annu. Rev. Biophys. Biomol. Struct. , vol. 26, pp. 401-424, 1997.

Maccallum, Robert M. et al "Antibody-Antigen Interactions: Contact Analysis and Binding Site Topography", Journal of Molecular Biology, Vo. 262, pp. 732-745, 1996.

Martine, Andrew C.R. et al "Modeling Antibody Hypervariable Loops: A COmbined Algorithm", Proc. Natl. Academy of Science, vol. 86, pp. 9268-9272, 1989.

Martin, Andrew C.R. et al "Molecular Modeling of ANtibody Combining Sites", Methods in Enzymology, vol. 203, 1991.

Mather, Jennie P. "Establishment and Characterization of Two Distinct Mouse Testicular Epithelial Cell Lines", Biology of Reproduction, vol. 23, pp. 243-252, 1980.

Mather, Jennie P. et al "Culture of Testicular Cells in Hormone-Supplemented Sserum-Free Medium" NYAS, 1982.

Morrison, Sherie L. et al "Chimeric human antibody molecules: Mouse Antigen-binding domains with human constant region domains", Proc. Natl. Academy of Science, vol. 81, pp. 6851-6855, 1984.

Morrison, Sherie L. et al "Genetically Engineered Antibody Molecules", Advances in Immunology, vol. 44, 1989.

Nishimiya, Yoshiyuki et al "Thermodynamic Consequences of Grafting Enhanced Affinity toward the Mutated Antigen onto an Antibody", The Journal of Biological Chemistry, vol. 275, No. 17, 2000.

O'marcaigh, Aengus S. et al "Estimating the Predictive Value of a Diagnostic Test", Clinical Pediatrics, 1993.

Ouwehand, W.H. et al "Novel Disgnostic and Therapeutic Strategies with Genetically Engineered Human Antibodies", Vox Sanguinis, vol. 74, 1998.

Padlan, Eduardo A. A Possible Procedure for Reducing the Immunogenicity of Antibody variable Domains while preserving their Ligand-binding Properties, Molecular Immunology, vol. 28, No. 4, pp. 489-498, 1991.

Padlan, Eduardo A. "Anatomy of the ANtibody MOlecule", Molecular Immunology, vol. 31, No. 3, pp. 169-217, 1994.

Pepe, Margaret Sullivan et al "Limitations of the Odds Ratio in Gauging the Performance of a Diagnostic Prognostic, or Screening Marker", American Journal of Epidemiology vol. 159, No. 9, 2004.

Rader, Christoph et al "A Phage Display approach for rapid antibody humanization: Designed combinatorial V. gene Libraries", Proc. Natl. Academy of Science, vol. 95, p. 8910=8915, 1998.

Radioimmunoassay Methods EP Workshop, 1970.

Rajpal, Arvind et al "A General Method for Greatly improving the affinity of Antibodies by using combinatorial libraries", PNAS, vol. 102, No. 24, pp. 8466-8471, 2005.

Roth, David B. et al "VDJ Recombination: A Transposase goes to work", Cell, vol. 94, pp. 411-414, 1998.

Ruiz, Manuel et al Nucleic Acids Research, International Immunogene Tics Database, vol. 28, No. 1, pp. 219-221, 2000.

Sanger, F. et al "DNA Sequencing with Chain-Terminating Inhibitors", Proc. Natl. Academy of Science, vol. 74, No. 12, pp. 5463-5467, 1977.

Schoonjans, Reinhilde et al "Fab Chains as an Efficient Heterodimerization Scafold for the Production of Recombinant Bispecific and Trispecific Antibody Derivatives", The Journal of Immunology, vol. 165, pp. 7050-7057, 2000.

Studnicka, Gary M. et al "Human-Engineered Monoclonal Antibodies retain full Specific Binding Activity by Preserving non-CDR Complementarity-Modulating Residues", Protein Engineering, vol. 7, No. 6, pp. 805-814, 1994.

Urlaub, Gail et al "Isolation of CHinese Hamster Cell Mutants deficient in Dihydrofolate Reductase Activity", Proc. Natl. Academy of Science, Vo. 77, No. 7, pp. 4216-4220, 1980.

Verhoeyen, Martine et al "Reshaping Human Antibodies: Graftng an Antilysozyme Activity", Science, vol. 239, 1987.

Ward, E. Sally et al "Binding Activities of a Repertoire of Single Immunoglobulin Variable Domains secreted from *Escherichia coli*", Letters to Nature, 1989.

Willems, An et al "Optimizing Expression and Purification from Cell Culture medium of Trispecific Recombinant Antibody Derivatives" Journal of Chromatography B. vol. 786, pp. 161-176, 2003.

Zweig, Mark et al "RocCurve Analysis: An Example Showing the Relationships among Serum Lipid and Apolipoprotein Concentra-

(56) References Cited

OTHER PUBLICATIONS tions in Identifying Patients with Coronary Artery Disease", Clin. Chem. vol. 38, No. 8, pp. 1425-1428, 1992.

* cited by examiner

A)

B)

A)

B)

A)

B)

C)

D)

DIAGNOSTIC METHOD EMPLOYING HNL

CROSS-REFERENCE TO PRIOR APPLICATIONS

This application is the U.S. National Phase application under 35 U.S.C. § 371 of International Application No. PCT/EP2015/077045, filed on Nov. 19, 2015, which claims the benefit of European Patent Application No. 14193886.0, filed on Nov. 19, 2014. These applications are hereby incorporated by reference herein.

FIELD OF THE INVENTION

The present invention relates to the means and methods for the detection of bacterial infections, methods discriminating between viral and bacterial infections, methods of stratifying patients for subsequent treatment and further diagnostic purposes and methods to monitor antibiotherapy. The present invention is based on the detection of specific epitopes of human neutrophil lipocalin (HNL) using specific binding agents.

BACKGROUND OF THE INVENTION

New antibiotic resistance mechanisms emerge and spread globally threatening the ability to treat common infectious diseases, resulting in death and disability of individuals who until recently could continue a normal course of life. Without effective anti-infective treatment, many standard medical treatments will fail or turn into very high risk procedures (http://www.who.int/mediacentre/factsheets/fs194/en/; Antimicrobial resistance—Fact sheet No. 194, updated April 2014).

In 2012, there were about 450,000 new cases of multidrug-resistant tuberculosis (MDR-TB). Extensively drug-resistant tuberculosis (XDR-TB) has been identified in 92 countries. MDR-TB requires treatment courses that are much longer and less effective than those for non-resistant TB. There are high proportions of antibiotic resistance (ABR) in bacteria that cause common infections (e.g. urinary tract infections, pneumonia, bloodstream infections) in all regions of the world. A high percentage of hospital-acquired infections are caused by highly resistant bacteria such as Methicillin-Resistant *Staphylococcus aureus* (MRSA) or multidrug-resistant Gram-negative bacteria. Treatment failures due to resistance to treatments of last resort for gonorrhea (third-generation cephalosporins) have now been reported from 10 countries. Gonorrhea may soon become untreatable as no vaccines or new drugs are in development. Patients with infections caused by drug-resistant bacteria are generally at increased risk of worse clinical outcomes and death, and consume more healthcare resources than patients infected with the same bacteria that are not resistant.

As an example, the death rate for patients with serious infections caused by common resistant bacteria treated in hospitals can be about twice that of patients with infections caused by the same non-resistant bacteria. For example, people with MRSA, another common source of severe infections in the community and in hospitals, are estimated to be 64% more likely to die than people with a non-resistant form of the infection.

Various modes of behaviors favor the development of AMR. For example, antibiotics are extensively used for prophylaxis in animal breeding and livestock industry, e.g. to increase weight gain. This leads to development of resistant bacteria in these animals, their transmission to humans working with these animals or consumers buying and using products from affected animals or farms. Another problem is the contamination of the environment surrounding animal farm. Further, the development of AMR may also result from the careless prescription and distribution of antimicrobial drugs, e.g. antibiotics, to patients that do not need these medicaments, for example because the severity of the illness does not justify the use of antibiotics, or the illness is not due to bacterial infection. Additionally, antibiotics are freely available as OTC drugs in several countries. Patients frequently do not use these antibiotics for a sufficiently long period of time, they do not use the right antibiotics for their respective illnesses, or they do not properly discard remaining antibiotics, but release it to the environment, e.g. by flushing them down the toilet.

There is an increasing need in the field to discriminate between bacterial and viral infections and to administer antibiotics only to patients with confirmed bacterial infections. It is one objective of the present invention to provide means and methods for this purpose.

Human neutrophil lipocalin (HNL) (also named neutrophil gelatinase-associated lipocalin (NGAL)), is a ubiquitous glycoprotein originally isolated from human neutrophils and localized in their specific granules. HNL/NGAL exists as a 25-kD monomer, or as a 45-kD disulfide-linked homodimer, and it is covalently conjugated with gelatinase (matrix metalloproteinase 9) via an intermolecular disulfide bridge as a 135-kD heterodimeric form (Cai et al., Clin J Am Soc Nephrol. December 2010; 5(12): 2229-2235). The amino acid sequence of HNL is shown in SEQ ID NO: 1 corresponding to the protein sequence found in www.uniprot.org/uniprot/P80188, in particular referring to isoform 1.

The discriminatory power of HNL in the discrimination between acute viral and acute bacterial infections showed variations in sensitivities and specificities between 75-94%. The lower figures are obviously not satisfactory in a clinical setting and the goal of the development should be an HNL assay that reliably rules-out bacteria as the cause of the acute infections in order to reduce the need to treat the infection with antibiotics. A secondary goal should be a reliable identification of those acute infections in need of antibiotics treatment.

Measurement of HNL (human neutrophil lipocalin) in serum or plasma can be used to discriminate acute infections caused by virus from those caused by bacteria as disclosed in EP 0 756 708 B1.

It is an object of the invention to provide new binding agents specifically recognizing HNL and to provide methods and uses of such binding agents, e.g. in the detection of bacterial infections, the selection of the appropriate treatment of patients, and the like.

Another objective of the invention is the monitoring of septic patients undergoing antibiotherapy e.g. to help to determine efficacy of treatment and time of cessation of antibiotics through repeated testing of sample of patients at different timepoints

SUMMARY OF THE INVENTION

The present invention provides means for and methods of detecting HNL in a sample. These means are binding agents, e.g. antibodies or derivatives thereof that are characterized by their binding regions (e.g. the CDR regions) as well as their capacities to bind specifically to HNL. The binding agents of the present invention can be used in the specific detection of HNL, and permit distinguishing between bacterial and viral infections. In some embodiments, the amount of HNL as a parameter is suitable for the identification of bacterial infections and/or distinguishing bacterial from viral infections and can be used in diagnosis of disease, prognosis of clinical outcomes, or in the monitoring of the course of anti-bacterial treatments. The correct diagnosis of an acute bacterial infection permits prescribing antibiotics appropriately to a subject from whom a sample is subjected to analysis of the presence or absence or quantity of HNL, e.g. in blood samples or urine samples.

In embodiments of the invention, the biological sample can be pretreated with a neutrophil activator to improve the detection of HNL and further improve the herein disclosed methods. In preferred embodiments the neutrophil activator is an N-formyl peptide, more preferably the tri-peptide fMLP. In further embodiments, the neutrophil activator is Protein A, or may be a combination of fMLP and Protein A. The present invention further envisages that the neutrophil activator is Lipopolysaccharide (LPS), platelet-activating factor, an unmethylated CpG oligodinucleotide, or tumor necrosis factor (TNF). Thus, according to specific embodiments of the present invention, the neutrophil activator may be any combination of two or more of the elements selected from the group consisting of fMLP, Protein A, Lipopolysaccharide (LPS), platelet-activating factor, an unmethylated CpG oligodinucleotide, and tumor necrosis factor (TNF).

In one embodiment of the invention, a polypeptide, e.g. a recombinantly produced polypeptide, comprising an amino acid sequence corresponding to amino acid 83 through 154 of HNL, or monomeric or dimeric HNL purified from human plasma/serum may be used in the production of a binding agent specifically recognizing HNL. The polypeptide can be used to immunize an animal, obtain antibody producing cells, produce hybridoma cells, harvest antibodies, optionally elucidate their sequence and further optionally produce recombinant antibodies, characterize these antibodies for their capacity to specifically bind HNL, and use these antibodies in the diagnosis of bacterial infections by determination of the HNL level in a sample. The antibodies may be modified as described herein below.

In embodiments of the invention, methods for detecting or diagnosing a bacterial and/or viral infection, or permitting the discrimination between viral and bacterial infections are provided, characterized in that the HNL-level in a sample is measured using a binding agent specifically binding to amino acids of epitopes of HNL that are exposed on the inner and outer rim surface as depicted in FIG. 1, wherein these epitopes preferably comprise amino acids 83 to 88 (preferably amino acids 82 to 102) and/or 141 to 156 of HNL depicted in SEQ ID NO. 1. In additional embodiments, these epitopes further comprise amino acids 51 to 76 and/or 113 to 132 of HNL depicted in SEQ ID NO: 1.

Thus, in some embodiments the binding agents disclosed herein, and the methods wherein said binding agents are used, recognize specifically amino acids comprised by amino acids 51 to 76 and/or 82 to 102 and/or 113 to 132 and/or 141 to 156 of HNL (SEQ ID NO: 1). In a particularly preferred embodiment a binding agent is capable of specifically binding to a polypeptide epitope of HNL, wherein said polypeptide epitope comprises amino acids 141 to 156 of HNL as defined in SEQ ID NO: 1, or wherein said polypeptide epitope is a conformational epitope comprised by the peptide in SEQ ID No: 26.

In preferred embodiments of the present invention, the binding agent binds to HNL that is at least predominantly produced by neutrophils.

In some embodiments of the present invention, the binding agent disclosed and used herein binds to a region of HNL that is comprised by the sequence depicted in SEQ ID NO: 26.

In some embodiments of the present invention, the binding agent comprises a HNL epitope-specific binding region comprising at least one, two, three, four, five, or six amino acid sequences depicted in SEQ ID Nos: 8 to 13, 14 to 19, and 20 to 25, or a functional derivative thereof.

In another embodiment of the invention a method for diagnosing an infection, e.g. a bacterial infection, or re-testing a bacterial infection, e.g. in the course of treatment with antibiotics, is provided, or differentiating a bacterial infection from a viral infection characterized in that a sample, e.g. a sample obtained from a subject suspected to have a bacterial or viral infection is analyzed, is analyzed for the presence of the HNL-level using a binding agent specifically binding to the sequence depicted in SEQ ID NO: 26, or as defined herein above. Said method may comprise the steps:

a) Incubating a sample in the presence of said binding agent;
b) Optionally washing off unbound sample material;
c) Measuring the level of HNL in a sample from a subject suspected to have a bacterial or viral infection;
d) Comparing the level of HNL measured in step c) with one or more control samples, optionally obtained from
   (i) healthy subjects,
   (i) subjects known to have a bacterial infection, and
   (iii) subjects known to have a virus infection, and/or
   optionally comparing the level of HNL measured in step c) with one or more normalized control values indicative for healthy subjects, subjects with a virus infection, and/or subjects with a bacterial infection.

In a specific embodiment, the method comprises a further step of diagnosing a bacterial infection when the level of HNL in step c) is significantly higher than the level detected in control samples (i) of healthy subjects and (iii) of patients known to have a viral infection.

In another aspect the present invention relates to a method of ruling out a bacterial infection in a subject comprising:
a) measuring the polypeptide concentration of HNL in a sample obtained from a subject using a binding agent as defined above, or a diagnostic composition or kit as defined above; and
b) ruling out a bacterial infection for the subject if the polypeptide concentration of HNL determined in step (a) is lower than a pre-determined first threshold value.

In a further aspect, the present invention provides a method of ruling out a viral infection in a subject comprising:
a) measuring the polypeptide concentration of HNL in a sample obtained from a subject using a binding agent as defined above, or a diagnostic composition or kit as defined above; and
b) ruling out a viral infection for the subject if the polypeptide concentration of HNL determined in step (a) is higher than a pre-determined first threshold value.

In still another aspect the present invention relates to a method of ruling in a bacterial infection in a subject comprising:
a) measuring the polypeptide concentration of HNL in a sample obtained from a subject using a binding agent as defined above, or a diagnostic composition or kit as defined above; and
b) ruling in a bacterial infection for the subject if the polypeptide concentration of HNL determined in step (a) is higher than a pre-determined first threshold value.

In yet another aspect, the present invention provides a method of ruling in a viral infection in a subject comprising
a) measuring the polypeptide concentration of HNL in a sample obtained from a subject using a binding agent as defined above, or a diagnostic composition or kit as defined above; and
b) ruling in a viral infection for the subject if the polypeptide concentration of TRAIL determined in step (a) is lower than a pre-determined first threshold value.

In one embodiment, the above method of ruling out a bacterial infection or ruling in a viral infection further comprises
a) measuring the polypeptide concentration of TRAIL in a sample obtained from a subject; and
b) ruling out a bacterial infection or ruling in a viral infection for the subject if the polypeptide concentration of TRAIL determined in step (a) is higher than a pre-determined first threshold value.

In another embodiment, the above method of ruling out a viral infection or the method of ruling in a bacterial infection further comprises
a) measuring the polypeptide concentration of TRAIL in a sample obtained from a subject; and
b) ruling in a bacterial infection or ruling out a viral infection for the subject if the polypeptide concentration of TRAIL determined in step (a) is lower than a pre-determined first threshold value.

In a further aspect the present invention relates to a method of distinguishing between a bacterial infection and a viral infection in a subject comprising:
a) measuring the polypeptide concentration of HNL using a binding agent as defined above or a diagnostic composition or kit as defined above, and of CRP, optionally of TRAIL, in a sample obtained from a subject;
b) applying a pre-determined mathematical function on the concentrations of HNL and CRP and optionally of TRAIL, to compute a score;
c) comparing the score to a predetermined reference value.

In yet another aspect the present invention provides a method of distinguishing between a bacterial or mixed infection, and a viral infection in a subject comprising:
a) measuring the polypeptide concentration of HNL using a binding agent as defined above, or a diagnostic composition or kit as defined above, and of CRP, optionally of TRAIL, in a sample obtained from a subject;
b) applying a pre-determined mathematical function on the concentrations of HNL and CRP and optionally of TRAI, to compute a score;
c) comparing the score to a predetermined reference value.

According to a further aspect, the invention provides a method of providing a treatment recommendation for a subject comprising:
a) measuring the polypeptide concentration of HNL in a sample obtained from a subject using a binding agent as defined above, or a diagnostic composition or kit as defined above; and
b) recommending that the subject receives an antibiotic treatment if the polypeptide concentration of HNL determined in step (a) is higher than a pre-determined threshold value;
c) recommending that the patient does not receive an antibiotic treatment if the polypeptide concentration of HNL determined in step (a) is lower than a predetermined threshold value; or
d) recommending that the patient receive an anti-viral treatment if the polypeptide concentration of HNL determined in step (a) is lower than a pre-determined threshold value.

In one embodiment, the method of providing a treatment recommendation for a subject further comprises in step a) additionally measuring the polypeptide concentration of TRAIL in a sample obtained from a subject; and
b) recommending that the subject receives an antibiotic treatment if the polypeptide concentration of HNL determined in step (a) is higher than a pre-determined threshold value and if the concentration of TRAIL determined in step (a) is lower than a pre-determined threshold value;
c) recommending that the patient does not receive an antibiotic treatment if the polypeptide concentration of HNL determined in step (a) is lower than a predetermined threshold value and if the polypeptide concentration of TRAIL determined in step (a) is higher than a predetermined threshold value; or
d) recommending that the patient receive an anti-viral treatment if the polypeptide concentration of HNL determined in step (a) is lower than a pre-determined threshold value and if the polypeptide concentration of TRAIL determined in step (a) is higher than a predetermined threshold value.

According to another aspect, the present invention relates to a method of providing a diagnostic test recommendation for a subject comprising:
a) measuring the polypeptide concentration of HNL in a sample obtained from a subject using a binding agent as defined above, or a diagnostic composition or kit as defined above; and
b) recommending testing the sample for the presence of bacteria if the polypeptide concentration of HNL determined in step (a) is higher than a pre-determined threshold value; or
c) recommending testing the sample for the presence of a virus if the polypeptide concentration of HNL determined in step (a) is lower than a pre-determined threshold value.

According to one embodiment, the method of providing a diagnostic test recommendation for a subject, further comprises in step a) additionally measuring the polypeptide concentration of TRAIL in a sample obtained from a subject; and
b) recommending testing the sample for the presence of bacteria if the polypeptide concentration of HNL determined in step (a) is higher than a pre-determined threshold value and if the concentration of TRAIL determined in step (a) is lower than a pre-determined threshold value;
c) recommending testing the sample for the presence of a virus if the polypeptide concentration of HNL determined in step (a) is lower than a predetermined threshold value and if the polypeptide concentration of TRAIL determined in step (a) is higher than a predetermined threshold value.

The present invention further provides, in another aspect, a method of ruling out an infectious disease, preferably a bacterial or viral disease, in a subject comprising:
a) measuring the polypeptide concentration of HNL using a binding agent as defined above, or a diagnostic composition or kit as defined above, and the polypeptide concentration of one or more polypeptides selected from the group consisting of TRAIL, IP10, IL1Ra or Mac-2BP in a sample obtained from a subject;
b) applying a pre-determined mathematical function on the concentrations of the polypeptides measured to compute a score c) comparing the score to a predetermined reference value.

In yet another aspect, the present invention relates to a method of identifying the type of infection, preferably a bacterial or viral infection, in a subject is provided, comprising:
a) measuring the polypeptide concentration of HNL using a binding agent as defined above, or a diagnostic composition or kit as defined above and the levels of a first polypeptide determinant selected from the group consisting of TRAIL, IL1RA, IP 10, Mac-2BP, B2M, BCA-1, CHI3L1, Eotaxin, IL1a, MCP, CD62L, VEGFR2, CHP, CMPK2, CORO1C, EIF2AK2, ISG15, RPL22L1, RTN3, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, IgG non-specific bound molecules, IL1, I-TAC and TNFR1 in a sample obtained from a subject; and
b) measuring the levels of a second determinant selected from the group consisting of
  (i) the polypeptide determinants TRAIL, IL1RA, IP 10, Mac-2BP, B2M, BCA-1, CHI3L1, Eotaxin, IL1a, MCP, CD62L, VEGFR2, CHP, CMPK2, CORO1C, EIF2AK2, ISG15, RPL22L1, RTN3, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, IgG nonspecific bound molecules, IL1, I-TAC and TNFR1;
  (ii) the polypeptide determinants IFITM3, IFIT3, EIF4B, IFIT1, LOC26010, MBOAT2, MX1, OAS2, RSAD2, ADIPOR1, CD15, CD8A, IFITM1, and IL7;
  (iii) the polypeptide determinants CRP, SAA, TREM-1, PCT, IL-8, TREM-1 and IL6; or
  (iv) the non-polypeptide determinants Age, absolute neutrophil count (ANC), absolute lymphocyte count (ALC), neutrophil % (Neu (%)), lymphocyte % (Lym (%)), monocyte % (Mono (%)), Maximal temperature, Time from symptoms, Creatinine (Cr), Potassium (K), Pulse and Urea;
c) comparing the levels of HNL, first and second determinants to a reference value thereby identifying the type of infection in the subject wherein the measurement of the first and/or second determinant increases the accuracy of the identification of the type of infection over the measurement of HNL.

In a further aspect, the present invention relates to a method of identifying the type of infection, preferably a bacterial or viral infection, in a subject comprising:
a) measuring the polypeptide concentration of HNL using a binding agent as defined above, or a diagnostic composition or kit as defined above, and the levels of one or more polypeptide determinants selected from the group consisting of ABTB1, ADIPOR1, ARHGDIB, ARPC2, ATP6V0B, C1orf83, CD15, CES1, CORO1A, CSDA, EIF4B, EPSTI1, GAS 7, HERC5, IFI6, KIAA0082, IFIT1, IFIT3, IFITM1, IFITM3, LIPT1, IL7R, ISG20, LOC26010, LY6E, LRDD, LTA4H, MAN1C1, MBOAT2, NPM1, OAS2, PARP12, PARP9, QARS, RAB13, RAB31, RAC2, RPL34, PDIA6, PTEN, RSAD2, SART3, SDCBP, SMAD9, SOCS3, TRIM22, SART3, UBE2N, XAF1, ZBP1, CRP and MX1 in a sample obtained from a subject; and
b) comparing the levels of HNL and of the one or more polypeptide determinants to a reference value thereby identifying the type of infection in the subject.

In one embodiment, the method of identifying the type of infection further comprises measuring one or more non-polypeptide determinants, selected from the group consisting of Age, absolute neutrophil count (ANC), absolute lymphocyte count (ALC), neutrophil % (Neu (%)), lymphocyte % (Lym (%)), monocyte % (Mono (%)), Maximal temperature, Time from symptoms, Creatinine (Cr), Potassium (K), Pulse and Urea.

In another embodiment, the level of the determinants absolute neutrophil count (ANC) and neutrophil % (NEU (%)) are used to normalize the level of HNL.

In another embodiment of the invention methods of stratifying subjects into those having a having a bacterial disease and those not having a bacterial disease is provided comprising the above steps, and optionally comprising the step of therapeutically administering antibiotics to subjects identified as being infected by bacteria.

In some embodiments of the invention the sample is selected from the group consisting of blood (i.e. whole blood) or fractions thereof, e.g. serum, plasma, and/or urine, cerebrospinal fluid (CSF), bone marrow, saliva, and sputum.

Locations where the tests disclosed herein may be used and the methods described may be performed are intensive care units (ICU), hospitals, particularly emergency departments, neonatal departments, GP/physicians premises, pharmacies, community hospitals, and level 1 and level 2 settings.

In another embodiment the invention provides a device for the diagnosis of bacterial infections, said device comprising at least a compartment, e.g. a contact area, that comprises the herein described binding agents. The device may be a test strip with immobilized binding agents on at least (a part) of its surface, particles carrying immobilized binding agents on at least (a part) of its surface, etc. The surface may be three-dimensional, e.g. particles with a partially porous surface (layer) may carry the above binding agents. It is important that the device comprises a contact area that can be exposed to a sample that is analyzed, e.g. a sample that is suspected to contain HNL. In embodiments of the device of invention, the determination of the level of HNL is possible. In further embodiments, the device may be connected to other devices, e.g. those suitable to take a blood sample from a subject suspected to have a bacterial infection, or it may be connected to a computer or apparatus permitting to analyze and measure the interaction between the binding agents disclosed herein and HNL that is present in a sample. The interaction may be measured using a physical, chemical or biological signal that is specifically generated upon binding of HNL and the herein described binding agent(s). The interaction may produce a measurable signal, e.g. a chromogenic signal, a fluorogenic signal, a spectroscopically measurable signal, a change in ionization, a change in conductivity and the like when compared with controls, where no interaction has occurred.

In a specific embodiment, the device as mentioned above additionally comprises a binding agent for one or more of the additional polypeptide determinants mentioned above, wherein said reactions are indicative for an interaction of the polypeptide determinants, and which further optionally permits determining the level of said polypeptide determinants in said sample.

In a specific embodiment the present invention relates to method as defined herein above, which further comprise measuring the level of C-reactive protein, and/or of TRAIL, and/or of procalcitonin, and/or of CD64, and/or determining the number of white blood cells and/or determining the number of neutrophils.

In another embodiment the invention provides a method of producing an antibody comprising the step of culturing antibody-producing cells obtained from an animal previously exposed to an antigen comprising the sequence in SEQ ID NO: 26, and providing the antibodies, optionally further modifying the obtained antibodies. Preferably, the antibodies comprise a binding region comprising at least one, two, three, four, five, or six amino acid sequences depicted in SEQ ID Nos: 1 to 6, 7 to 12, and 13 to 18, or a functional derivative thereof.

The foregoing summary is not intended to define every aspect of the invention, and additional aspects are described in other sections, such as the Detailed Description. The entire document is intended to be related as a unified disclosure, and it should be understood that all combinations of features described herein may be contemplated, even if the combination of features are not found together in the same sentence, or paragraph, or section of this document.

In addition to the foregoing, the invention can include, as an additional aspect, all embodiments of the invention narrower in scope in any way than the variations defined by specific paragraphs herein. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus.

It should be understood that while various embodiments in the specification are presented using "comprising" language, under various circumstances, a related embodiment may also be described using "consisting of or "consisting essentially of language.

DETAILED DESCRIPTION OF EMBODIMENTS

Although the present invention will be described with respect to particular embodiments, this description is not to be construed in a limiting sense. Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably±15%, more preferably±10%, and even more preferably±5%.

It is to be understood that the term "comprising" is not limiting. For the purposes of the present invention the term "consisting of is considered to be a preferred embodiment of the term "comprising of. If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Figure 1:
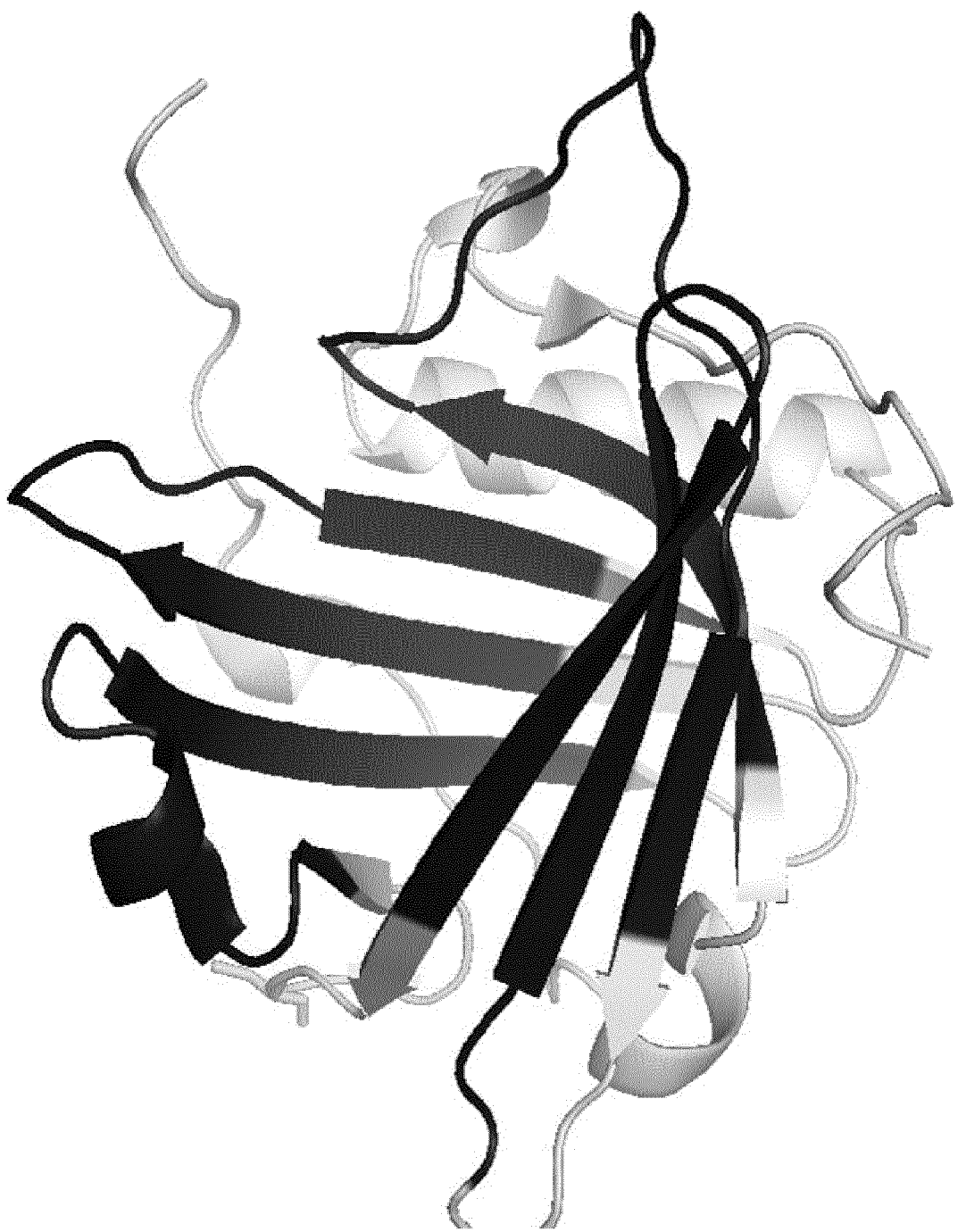
FIG. 1 is a graphical representation of the HNL-molecule.

In case the terms "first", "second", "third" or "(a)", "(b)", "(c)", "(d)" etc. relate to steps of a method or use there is no time or time interval coherence between the steps, i.e. the steps may be carried out simultaneously or there may be time intervals of seconds, minutes, hours, days, weeks, months or even years between such steps, unless otherwise indicated in the application as set forth herein above or below. It is to be understood that this invention is not limited to the particular methodology, protocols, proteins, bacteria, vectors, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art. In the context of the present invention, the term "binding agent" designates any molecule, e.g. peptides comprising natural and/or modified amino acids that permit them to specifically bind to the sequences of the herein described regions or epitopes of HNL, e.g. a binding agent that binds to the region of HNL that is exposed on the inner and/or outer rim surface of said molecule as depicted in FIG. 1 (dark parts of the 3D image). The binding agents recognize specifically amino acids comprised by amino acids 51 to 76 and/or 82 to 102 and/or 113 to 132 and/or 141 to 156 of HNL as depicted in SEQ ID NO: 1 and particularly to a discontinuous, preferably non-linear, conformational epitope comprised by the peptide in SEQ ID No: 26. Preferred binding agents are antibodies or functional fragments or derivatives thereof.

Within the context of the present application, the epitope may be slightly different, e.g. be about 80%, 81%, 82%, 83%, 84%, 85%, 86%, 87%, 88%, 89%, 90%, 91%, 92%, 93%, 94%, 95%, 96%, 97%, 98%, or 99% identical, provided the epitope is recognized by binding agents that specifically bind to HNL as defined above. Preferably, the binding agent recognized is HNL produced by neutrophils.

In the context of the present invention, the binding specificity of binding agents may be at least about e.g. 80%, 81%, 82%, 83%, 84%, 85%, 86%, 87%, 88%, 89%, 90%, 91%, 92%, 93%, 94%, 95%, 96%, 97%, 98%, or 99% as specific as the binding affinity of a binding agent that binds to HNL as described above, or even higher.

Within the meaning of the invention, "significantly" bound also means that, from among a pool of a plurality of equally accessible different antigens as potential binding partners, HNL is bound at least 10-fold, e.g., 50-fold, e.g., 100-fold or greater more frequently (in a kinetic sense) than any other antigen different from HNL. Such kinetic measurements can be performed on a Biacore apparatus.

The term "level" as used herein refers to the amount or concentration of HNL detected in a sample.

A "polynucleotide" is a polymeric form of nucleotides of any length, either ribonucleotides or deoxyribonucleotides. This term refers only to the primary structure of the molecule. Thus, this term includes double- and single-stranded DNA and RNA. It also includes known types of modifications including labels known in the art, methylation, "caps", substitution of one or more of the naturally occurring nucleotides with an analog, and internucleotide modifications such as uncharged linkages (e.g., phosphorothioates, phosphorodithioates, etc.), as well as unmodified forms of the polynucleotide.

In accordance with the present invention, the monoclonal antibody or functional fragment thereof may be derivatized, for example with a fluorescent moiety, a radioactive moiety, a chromogenic substrate, and the like.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains, respectively. The carboxy-terminal portion of each chain defines a constant region primarily responsible for effector function. Immunoglobulins can be assigned to different classes depending on the amino acid sequence of the constant domain of their heavy chains. Heavy chains are classified as mu (u), delta (δ), gamma (γ), alpha (α), and epsilon (ε), and define the antibody's isotype as IgM, IgD, IgG, IgA, and IgE, respectively. Several of these may be further divided into subclasses or isotypes, e.g. IgG1, IgG2, IgG3, IgG4, IgA1 and IgA2. Different isotypes have different effector functions; for example, IgG1 and IgG3 isotypes have antibody-dependent cellular cytotoxicity (ADCC) activity. Human light chains are classified as kappa (K) and lambda ([lambda]) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)).

Allotypes are variations in antibody sequence, often in the constant region, that can be immunogenic and are encoded by specific alleles in humans. Allotypes have been identified for five of the human IGHC genes, the IGHG1, IGHG2, IGHG3, IGHA2 and IGHE genes, and are designated as G1m, G2m, G3m, A2m, and Em allotypes, respectively. For a detailed description of the structure and generation of antibodies, see Roth, D. B., and Craig, N. L., Cell, 94:41 1-414 (1998), herein incorporated by reference in its entirety. Briefly, the process for generating DNA encoding the heavy and light chain immunoglobulin sequences occurs primarily in developing B-cells. Prior to the rearranging and joining of various immunoglobulin gene segments, the V, D, J and constant (C) gene segments are found generally in relatively close proximity on a single chromosome. During B-cell-differentiation, one of each of the appropriate family members of the V, D, J (or only V and J in the case of light chain genes) gene segments are recombined to form functionally rearranged variable regions of the heavy and light immunoglobulin genes. This gene segment rearrangement process appears to be sequential. First, heavy chain D-to-J joints are made, followed by heavy chain V-to-DJ joints and light chain V-to-J joints. In addition to the rearrangement of V, D and J segments, further diversity is generated in the primary repertoire of immunoglobulin heavy and light chains by way of variable recombination at the locations where the V and J segments in the light chain are joined and where the D and J segments of the heavy chain are joined. Such variation in the light chain typically occurs within the last codon of the V gene segment and the first codon of the J segment. Similar imprecision in joining occurs on the heavy chain chromosome between the D and JH segments and may extend over as many as 10 nucleotides. Furthermore, several nucleotides may be inserted between the D and JH and between the VH and D gene segments which are not encoded by genomic DNA. The addition of these nucleotides is known as N-region diversity. The net effect of such rearrangements in the variable region gene segments and the variable recombination which may occur during such joining is the production of a primary antibody repertoire.

The term "antibody" is used in the broadest sense and includes fully assembled antibodies, monoclonal antibodies, polyclonal antibodies, multispecific antibodies (including bispecific antibodies), antibody fragments that can bind an antigen (including, Fab', F'(ab)2, Fv, single chain antibodies, diabodies), and recombinant peptides comprising the foregoing as long as they exhibit the desired biological activity. Multimers or aggregates of intact molecules and/or fragments, including chemically derivatized antibodies, are contemplated. Antibodies of any isotype class or subclass, including IgG, IgM, IgD, IgA, and IgE, IgG1, IgG2, IgG3, IgG4, IgA1 and IgA2, or any allotype, are contemplated.

The term "hypervariable" region refers to amino acid residues from a complementarity determining region or CDR (i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed. Public Health Service, National Institutes of Health, Bethesda, Md. (1991)). Even a single CDR may recognize and bind antigen, although with a lower affinity than the entire antigen binding site containing all of the CDRs.

An alternative definition of residues from a hypervariable "loop" is described by Chothia et al., J. Mol. BioL, 196: 901-917 (1987) as residues 26-32 (L1), 50-52 (L2) and 91-96 (L3) in the light chain variable domain and 26-32 (H1), 53-55 (H2) and 96-101 (H3) in the heavy chain variable domain.

"Framework" or FR residues are those variable region residues other than the hypervariable region residues.

"Antibody fragments" comprise a portion of an intact immunoglobulin, e.g., an antigen binding or variable region of the intact antibody, and include multispecific (bispecific, trispecific, etc.) antibodies formed from antibody fragments. Fragments of immunoglobulins may be produced by recombinant DNA techniques or by enzymatic or chemical cleavage of intact antibodies. Nonlimiting examples of antibody fragments include Fab, Fab', F(ab')2, Fv (variable region), domain antibodies (dAb, containing a VH domain; Ward et al., Nature, 341, 544-546, 1989), complementarity determining region (CDR) fragments, single-chain antibodies (scFv, containing VH and VL domains on a single polypeptide chain) (Bird et al., Science, 242: 423-426, 1988, and Huston et al., Proc. Natl. Acad. Sci., USA 85: 5879-5883, 1988, optionally including a polypeptide linker; and optionally multispecific, Gruber et al., J. Immunol., 152: 5368 (1994)), single chain antibody fragments, diabodies (VH and VL domains on a single polypeptide chain that pair with complementary VL and VH domains of another chain) (EP 404,097; WO 93/1 1161; and Holliger et al., Proc. Natl. Acad. Sci., USA, 90: 6444-6448 (1993)), triabodies, tetrabodies, minibodies (scFv fused to CH3 via a peptide linker (hingeless) or via an IgG hinge), linear antibodies (tandem Fd segments (VH-CH1-VH-CHI) (Zapata et al., Protein Eng., 8(10): 1057-1062 (1995)); chelating recombinant antibodies (crAb, which can bind to two adjacent epitopes on the same antigen), bibodies (bispecific Fab-scFv) or tribodies (trispecific Fab-(scFv)(2)) (Schoonjans et al., J Immunol. 165: 7050-57, 2000; Willems et al., J. Chromatogr. B. Analyt. Technol. Biomed. Life Sci., 786: 161-76, 2003), nanobodies (approximately 15 kDa variable domain of the heavy chain) (Cortez-Retamozo et al., Cancer Research 64: 2853-57, 2004), an antigen-binding-domain immunoglobulin fusion protein, a camelized antibody (in which VH recombines with a constant region that contains hinge, CH1, CH2 and CH3 domains) (Desmyter et al., J. Biol. Chem., 276: 26285-90, 2001; Ewert et al., Biochemistry, 41:3628-36, 2002; U.S. Patent Application Publication Nos. 2005/0136049 and 2005/0037421), a VHH containing antibody, heavy chain antibodies (HCAbs, homodimers of two heavy chains having the structure H2L2), or variants or derivatives thereof, and polypeptides that contain at least a portion of an immunoglobulin that is sufficient to confer specific antigen binding to the polypeptide, such as a CDR sequence, as long as the antibody retains the desired biological activity.

The term "variant" refers to a polypeptide sequence of an antibody that contains at least one amino acid substitution, deletion, or insertion in the variable region or the portion equivalent to the variable region, provided that the variant retains the desired binding affinity or biological activity The term "modification" includes but is not limited to, one or more amino acid change (including substitutions, insertions or deletions); chemical modifications that do not interfere with HNL-binding activity; covalent modification by conjugation to diagnostic agents; labeling (e.g., with radionuclides or various enzymes); covalent polymer attachment such as pegylation (derivatization with polyethylene glycol) and insertion or substitution by chemical synthesis of non-natural amino acids. In some embodiments, modified polypeptides (including antibodies) will retain the binding properties of unmodified molecules.

The term "derivative" refers to antibodies or polypeptides that are covalently modified by conjugation to diagnostic agents, labeling (e.g., with radionuclides or various enzymes), covalent polymer attachment such as pegylation (derivatization with polyethylene glycol) and insertion or substitution by chemical synthesis of non-natural amino acids. In some embodiments, derivatives will retain the binding properties of underivatized molecules.

The term "monoclonal antibody" as used herein refers to an antibody, as that term is defined herein, obtained from a population of substantially homogeneous antibodies, i.e., the individual antibodies comprising the population are identical except for possible naturally occurring mutations or alternative post-translational modifications that may be present in minor amounts, whether produced from hybridomas or recombinant DNA techniques. Nonlimiting examples of monoclonal antibodies include murine, rabbit, rat, chicken, chimeric, humanized, or human antibodies, fully assembled antibodies, multispecific antibodies (including bispecific antibodies), antibody fragments that can bind an antigen (including, Fab', F'(ab)2, Fv, single chain antibodies, diabodies), maxibodies, nanobodies, and recombinant peptides comprising the foregoing as long as they exhibit the desired biological activity, or variants or derivatives thereof. Humanizing or modifying antibody sequence to be more human-like is described in, e.g., Jones et al., Nature 321:522 525 (1986); Morrison et al., Proc. Natl. Acad. ScL1 U.S.A., 81:6851 6855 (1984); Morrison and Oi, Adv. Immunol., 44:65 92 (1988); Verhoeyer et al., Science 239:1534 1536 (1988); Padlan, Molec. Immun., 28:489 498 (1991); Padlan, Molec. Immunol, 31(3): 169 217 (1994); and Kettleborough, Calif. et al., Protein Engineering., 4(7):773 83 (1991); Co, M. S., et al. (1994), J. Immunol 152, 2968-2976); Srudnicka et al., Protein Engineering 7: 805-814 (1994); each of which is incorporated herein by reference in its entirety. One method for isolating human monoclonal antibodies is the use of phage display technology. Phage display is described in e.g., Dower et al., WO 91/17271, McCafferty et al., WO 92/01047, and Caton and Koprowski, Proc. Natl. Acad. Sci. USA, 87: 6450-6454 (1990), each of which is incorporated herein by reference in its entirety. Another method for isolating human monoclonal antibodies uses transgenic animals that have no endogenous immunoglobulin production and are engineered to contain human immunoglobulin loci. See, e.g., Jakobovits et al., Proc. Natl. Acad. Sci. USA, 90:2551 (1993); Jakobovits et al., Nature, 362: 255-258 (1993); Bruggermann et al., Year in Immuno., 7:33 (1993); WO 91/10741, WO 96/34096, WO 98/24893, or U.S. Patent Application Publication Nos. 2003/0194404, 2003/0031667 or 2002/0199213; each incorporated herein by reference in its entirety.

Antibodies of the invention also include heavy chain dimers, such as antibodies from camelids. Since the VH region of a heavy chain dimer IgG in a camelid does not have to make hydrophobic interactions with a light chain, the region in the heavy chain that normally contacts a light chain is changed to hydrophilic amino acid residues in a camelid. VH domains of heavy-chain dimer IgGs are called VHH domains. Antibodies for use in the current invention include single domain antibodies (dAbs) and nanobodies (see, e.g., Cortez-Retamozo, et al., Cancer Res. 64: 2853-2857, 2004).

As used herein, "V-region" refers to an antibody variable region domain comprising the segments of Framework 1, CDR1, Framework 2, CDR2, and Framework 3, including CDR3 and Framework 4, which segments are added to the V-segment as a consequence of rearrangement of the heavy chain and light chain V-region genes during B-cell differentiation. A "V-segment" as used herein refers to the region of the V-region (heavy or light chain) that is encoded by a V gene.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, for example, a VH CDR3 is located in the variable domain of the heavy chain of the antibody in which it is found, whereas a VL CDR1 is the CDR1 from the variable domain of the light chain of the antibody in which it is found. The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. J. Mol. Biol. 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., J.Mol.Biol 1997, 273 (4)). Definitions of antigen combining sites are also described in the following: Ruiz et al., IMGT, the international ImMunoGeneTics database. Nucleic Acids Res., 28, 219-221 (2000); and Lefranc, M.-P. IMGT, the international ImMunoGeneTics database. Nucleic Acids Res. January 1; 29 (1): 207-9 (2001); MacCallum et al, Antibody antigen interactions: Contact analysis and binding site topography, J. Mol. Biol., 262 (5), 732-745 (1996); and Martin et al, Proc. Natl Acad. Sci. USA, 86, 9268-9272 (1989); Martin, et al, Methods Enzymol., 203, 121-153, (1991); Pedersen et al, Immunomethods, 1, 126, (1992); and Rees et al, In Sternberg M.J.E. (ed.), Protein Structure Prediction.Oxford University Press, Oxford, 141-172 1996).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding (also referred to as discontinuous epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

A variety of compositions comprising one, two, and/or three CDRs of a heavy chain variable region or a light chain variable region of an antibody may be generated by techniques known in the art.

Isolated nucleic acids encoding monoclonal antibodies described herein are also provided, optionally operably linked to control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium.

Relevant amino acid sequence from an immunoglobulin of interest may be determined by direct protein sequencing, and suitable encoding nucleotide sequences can be designed according to a universal codon table. Alternatively, genomic or cDNA encoding the monoclonal antibodies may be isolated and sequenced from cells producing such antibodies using conventional procedures (e.g., by using oligonucleotide probes that are capable of binding specifically to genes encoding the heavy and light chains of the monoclonal antibodies). Cloning is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+ mRNA, e.g., membrane-associated mRNA, and the library screened using probes specific for human immunoglobulin polypeptide gene sequences. In one embodiment, however, the polymerase chain reaction (PCR) is used to amplify cDNAs (or portions of full-length cDNAs) encoding an immunoglobulin gene segment of interest (e.g., a light or heavy chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest.

The phrase "specifically (or selectively) binds" to an antibody or "specifically (or selectively) immunoreactive with", when referring to a protein or peptide, refers to a binding reaction that is determinative of the presence of the protein, in a heterogeneous population of proteins and other biologics. Thus, under designated immunoassay conditions, the specified antibodies bind to a particular protein sequence at least two times the background and more typically more than 10 to 100 times background. The term refers also to the ability of the binding agent, the antibody or functional fragment or derivative thereof to bind to HNL, particularly to a discontinuous epitope comprised by the peptide in SEQ ID No: 26.

In some embodiments, an isolated antibody or derivative or fragment is provided that binds to HNL with an affinity KD of about $10^{-6}$ M to $10^{-8}$ M.

The term "binding affinity" or "affinity" as used herein refers to the equilibrium dissociation constant ($K_D$) associated with each antigen-antibody interaction. In some embodiments, the antibodies described herein exhibit desirable properties such as binding affinity as measured by $K_D$ for HNL in the range of $1\times10^{-6}$M or less, or ranging down to $10^{-16}$ M or lower, (e.g., about $10^{-6}$, $10^{-7}$, $10^{-8}$, $10^{-9}$, $10^{-10}$, $10^{-11}$, $10^{-12}$, $10^{-13}$, $10^{-14}$, $10^{-15}$, $10^{-16}$ or less) at about pH 7.4, where lower KD indicates better affinity. The equilibrium dissociation constant can be determined in solution equilibrium assay using, e.g., BIAcore.

The binding affinity is directly related to the ratio of the kinetic off-rate (generally reported in units of inverse time, e.g. seconds$^{-1}$) divided by the kinetic on-rate (generally reported in units of concentration per unit time, e.g. M/s). Off-rate analysis can estimate the interaction that occurs in vivo, since a slow off-rate would predict a greater degree of interaction over long period of time.

In other embodiments, the antibodies described herein exhibit specificity for or specifically bind to HNL. As used herein, an antibody is "specific for" or "specifically binds" HNL when it has a significantly higher binding affinity for, and consequently is capable of distinguishing, HNL compared to other unrelated proteins in different families. In some embodiments, such antibodies may also cross-react with HNL of other species, such as murine, rat, or primate HNL; while in other embodiments, the antibodies bind only to human HNL. Any of the foregoing antibodies may be a monoclonal antibody, or a chimeric, humanized, or human antibody. In some embodiments, the antibody is an IgG isotype, such as an IgG1, IgG2, IgG3 or IgG4 isotype.

In another aspect, embodiments of the invention include an isolated nucleic acid molecule comprising a nucleotide sequence that encodes any of the foregoing antibodies, an expression vector comprising any of the isolated nucleic acid molecules, operably linked to a regulatory control sequence, host cells comprising such isolated nucleic acid molecules or vectors, and methods of using such host cells to produce an antibody. Such production methods comprise culturing the host cell under suitable conditions such that the nucleic acid is expressed to produce the antibody, and optionally recovering the antibody from the host cell or culture medium. In a related embodiment, an isolated antibody or agent produced by the aforementioned method is provided.

Embodiments described herein include a composition, e.g. a diagnostic composition, that contains any of the foregoing binding agents, e.g. antibodies.

In some embodiments, the invention concerns:
1) a binding agent, e.g. an antibody that retains any one, two, three, four, five, or six of CDRH1, CDRH2, CDRH3, CDRL1, CDRL2 or CDRL3 as depicted in Nos: 8 to 13, 14 to 19, and 20 to 25, or derivatives thereof;
2) a binding agent, e.g. an antibody that retains all of CDRH1, CDRH2, CDRH3, optionally including one or two mutations in such CDR(s), wherein the antibody exhibits specific binding to the HNL epitope comprised in SEQ ID NO: 26;
3) a binding agent, e.g. an antibody that retains all of CDRL1, CDRL2, CDRL3, optionally including one or two mutations in such CDR(s), optionally including one or two mutations in such CDR(s), wherein the antibody exhibits specific binding to the HNL epitope comprised in SEQ ID NO: 26;
4) a binding agent, e.g. an antibody that binds to the same epitope of HNL as the herein described antibodies, e.g. as determined through X-ray crystallography, or a conformational epitope comprising an amino acid comprised in of SEQ ID NO: 26 for binding to (human) HNL by more than about 75%, more than about 80%, or more than about 81%, 82%, 83%, 84%, 85%, 86%, 87%, 88%, 89%, 90%, 91%, 92%, 93%, 94% or 95% (e.g., assessed by competitive ELISA or Biacore or by other methods known in the art).

In another aspect, methods are provided for mutating antibodies according to the invention, that retain specific binding affinity for HNL, particularly for the epitope comprised by SEQ ID NO: 26. The antibody can be an anti-HNL antibody produced by such methods. Candidate residues for mutation include residues that are directed contact sites with antigen or sites that contribute to the formation of charge-charge interactions along the antibody-antigen binding interface. Other candidate residues include residues within conserved regions of the antibody. Yet other candidate residues include framework residues that are at least 10% surface exposed and within 4.5 Å of a CDR residue. Additional candidate residues include those selected by visual inspection of a 3-dimensional structural model for amino acids in proximity to the CDRs or selected framework residues. Desired amino acids can be mutated at single or multiple positions within the amino acid sequence. For example, mutations which produce some differential binding effect as single mutations can be combined as double, triple or more multiple mutations. Antibodies that have been mutated in such a manner are then screened for differential, e.g. improved, binding and then can be further screened for other properties.

In one aspect, at least one, two, three, four, five, six or more residues in the heavy chain variable region of said antibody are deleted and replaced with another residue. In another aspect, at least one, two, three, four, five, six or more residues in the light chain variable region of said antibody are deleted and replaced with a different residue. In some aspects, at least one residue from the light chain variable region of said antibody and at least one residue from the heavy chain variable region of said antibody is replaced with a different residue, provided the specific binding activity of said antibody is maintained.

In one embodiment, the antibody comprises at least one, two, three, four, five or all of the amino acid sequences selected from the group consisting of Nos: 8 to 13, 14 to 19, and 20 to 25. In some embodiments, the antibody comprises all three light chain CDRs, all three heavy chain CDRs, or all six CDRs. In some embodiments, two light chain CDRs from an antibody may be combined with a third light chain CDR from a different antibody. Alternatively, a CDRL1 from one antibody can be combined with a CDRL2 from a different antibody and a CDRL3 from yet another antibody, particularly where the CDRs are highly homologous. Similarly, two heavy chain CDRs from an antibody may be combined with a third heavy chain CDR from a different antibody; or a CDRH1 from one antibody can be combined with a CDRH2 from a different antibody and a CDRH3 from yet another antibody, particularly where the CDRs are highly homologous.

One source for antibody nucleic acids is a hybridoma produced by obtaining a B cell from an animal immunized with the antigen of interest and fusing it to an immortal cell. Alternatively, nucleic acid can be isolated from B cells (or whole spleen) of the immunized animal. Yet another source of nucleic acids encoding antibodies is a library of such nucleic acids generated, for example, through phage display technology. Polynucleotides encoding peptides of interest, e.g., variable region peptides with desired binding characteristics, can be identified by standard techniques such as panning.

The sequence encoding an entire variable region of the immunoglobulin polypeptide may be determined; however, it will sometimes be adequate to sequence only a portion of a variable region, for example, the CDR-encoding portion. Sequencing is carried out using standard techniques (see, e.g., Sambrook et al. (1989) Molecular Cloning: A Laboratory Guide, Vols 1-3, Cold Spring Harbor Press, and Sanger, F. et al., (1977) Proc. Natl. Acad. Sci. USA, 74: 5463-5467, which is incorporated herein by reference). By comparing the sequence of the cloned nucleic acid with published sequences of immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

As used herein, an "isolated" nucleic acid molecule or "isolated" nucleic acid sequence is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined. An isolated nucleic acid molecule is other than in the form or setting in which it is found in nature. However, an isolated nucleic acid molecule includes a nucleic acid molecule contained in cells that ordinarily express the antibody where, for example, the nucleic acid molecule is in a chromosomal location different from that of natural cells.

Once isolated, the DNA may be operably linked to expression control sequences or placed into expression vectors, which are then transfected into host cells that do not otherwise produce immunoglobulin protein, to direct the synthesis of monoclonal antibodies in the recombinant host cells. Recombinant production of antibodies is well known in the art. Expression control sequences refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. A nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Many vectors are known in the art. Vector components may include one or more of the following: a signal sequence (that may, for example, direct secretion of the antibody), an origin of replication, one or more selective marker genes (that may, for example, confer antibiotic or other drug resistance, complement auxotrophic deficiencies, or supply critical nutrients not available in the media), an enhancer element, a promoter, and a transcription termination sequence, all of which are well known in the art.

Exemplary host cells to express the genetic information comprised in the vector upon transfection or transformation include prokaryote, yeast, or higher eukaryote cells (i.e., a multicellular organism). Prokaryotic host cells include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis, Pseudomonas*, and *Streptomyces*. Eukaryotic microbes such as filamentous fungi or yeast are suitable cloning or expression hosts for recombinant polypeptides or antibodies. *Saccharomyces cerevisiae*, or common baker's yeast, is the most commonly used among lower eukaryotic host microorganisms. However, a number of other genera, species, and strains are commonly available and useful herein, such as *Pichia*, e.g. *P. pastoris, Schizosaccharomyces pombe; Kluyveromyces, Yarrowia; Candida; Trichoderma reesia; Neurospora crassa; Schwan-* niomyces such as *Schwanniomyces occidentalis*; and filamentous fungi such as, e.g., *Neurospora, Penicillium, Tolypocladium*, and *Aspergillus* hosts such as *A. nidulans* and *A. niger*.

Host cells for the expression of glycosylated polypeptide or antibody can be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypy* (mosquito), *Aedes albopictus* (mosquito), *Drosophila melanogaster* (fruitfly), and *Bombyx mori* have been identified. A variety of viral strains for transfection of such cells are publicly available, e.g., the L-I variant of *Autographa californica* NPV and the Bm-5 strain of *Bombyx mori* NPV. Vertebrate host cells are also suitable hosts, and recombinant production of polypeptide or antibody from such cells has become routine procedure. Examples of useful mammalian host cell lines are Chinese hamster ovary cells, including CHOK1 cells (ATCC CCL61), DXB-1 1, DG-44, and Chinese hamster ovary cells/-DHFR (CHO, Urlaub et al., Proc. Natl. Acad. Sci. USA, 77: 4216 (1980)); monkey kidney CV1 line transformed by SV40 (COS-7, ATCC CRL 1651); human embryonic kidney line (293 or 293 cells subcloned for growth in suspension culture, [Graham et al., J. Gen Virol. 36: 59 (1977)]; baby hamster kidney cells (BHK, ATCC CCL 10); mouse Sertoli cells (TM4, Mather, Biol. Reprod., 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W 138, ATCC CCL 75); human hepatoma cells (Hep G2, HB 8065); mouse mammary tumor (MMT 060562, ATCC CCL51); TRI cells (Mather et al., Annals N. Y Acad. Sci, 383: 44-68 (1982)); MRC 5 cells or FS4 cells; or mammalian myeloma cells. Host cells are transformed or transfected with the above-described nucleic acids or vectors for antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful for the expression of antibodies.

The host cells used to produce an antibody described herein may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz., 58: 44 (1979), Barnes et al., Anal. Biochem., 102: 255 (1980), U.S. Pat. Nos. 4,767,704; 4,657,866; 4,927,762; 4,560,655; or 5,122,469; WO 90/03430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Upon culturing the host cells, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration.

The antibody can be purified using, for example, hydroxylapatite chromatography, cation or anion exchange chromatography, or affinity chromatography, using the antigen of interest or protein A or protein G as an affinity ligand. Protein A can be used to purify antibodies that are based on human γ1, γ 2, or γ4 heavy chains (Lindmark et al., J. Immunol. Meth. 62: 1-13 (1983)). Protein G is recommended for all mouse isotypes and for human γ 3 (Guss et al., EMBO J. 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH 3 domain, the Bakerbond ABX™ resin (J. T. Baker, Phillipsburg, N.J.) is useful for purification. Other techniques for protein purification such as ethanol precipitation, Reverse Phase HPLC, chromatofocusing, SDS-PAGE, and ammonium sulfate precipitation are also possible depending on the antibody to be recovered.

Other HNL-specific binding agents can be prepared, for example, based on CDRs from an antibody or by screening libraries of diverse peptides or organic chemical compounds for peptides or compounds that exhibit the desired binding properties for human HNL. HNL specific binding agent include peptides containing amino acid sequences that are at least 80%, 81%, 82%, 83%, 84%, 85%, 86%, 87%, 88%, 89%, 90%, 91%, 92%, 93%, 94%, 95%, 96%, 97%, 98%, 99% or more identical to one or more CDRs disclosed herein. HNL-specific binding agents also include peptibodies. The term "peptibody" refers to a molecule comprising an antibody Fc domain attached to at least one peptide. The production of peptibodies is generally described in PCT publication WO 00/24782, published May 4, 2000. Any of these peptides may be linked in tandem (i.e., sequentially), with or without linkers. Peptides containing a cysteinyl residue may be cross-linked with another Cys-containing peptide, either or both of which may be linked to a vehicle. Any peptide having more than one Cys residue may form an intrapeptide disulfide bond, as well. Any of these peptides may be derivatized, for example, the carboxyl terminus may be capped with an amino group, cysteines may be capped, or amino acid residues may substituted by moieties other than amino acid residues (see, e.g., Bhatnagar et al., J. Med. Chem., 39: 3814-9 (1996), and Cuthbertson et al., J. Med. Chem., 40: 2876-82 (1997), which are incorporated by reference herein in their entirety). The peptide sequences may be optimized, analogous to affinity maturation for antibodies, or otherwise altered by alanine scanning or random or directed mutagenesis followed by screening to identify the best binders. Lowman, Ann. Rev. Biophys. Biomol. Struct., 26: 401-24 (1997). Various molecules can be inserted into the specific binding agent structure, e.g., within the peptide portion itself or between the peptide and vehicle portions of the specific binding agents, while retaining the desired activity of specific binding agent. One can readily insert, for example, molecules such as an Fc domain or fragment thereof, polyethylene glycol or other related molecules such as dextran, a fatty acid, a lipid, a cholesterol group, a small carbohydrate, a peptide, a detectable moiety as described herein (including fluorescent agents, radiolabels such as radioisotopes), an oligosaccharide, oligonucleotide, a polynucleotide, interference (or other) RNA, enzymes, hormones, or the like. Other molecules suitable for insertion in this fashion will be appreciated by those skilled in the art, and are encompassed within the scope of the invention. This includes insertion of, for example, a desired molecule in between two consecutive amino acids, optionally joined by a suitable linker.

Methods of identifying antibodies or specific binding agents which bind HNL and/or which cross-block exemplary antibodies described herein, and/or which inhibit HNL activity are also provided. Antibodies or specific binding agents may be screened for binding affinity by methods known in the art. For example, gel-shift assays, Western blots, radiolabeled competition assay, co-fractionation by chromatography, co-precipitation, cross linking, ELISA, and the like may be used, which are described in, for example, Current Protocols in Molecular Biology (1999) John Wiley & Sons, NY, which is incorporated herein by reference in its entirety. In one embodiment, high throughput screening for antibody fragments or CDRs with 1, 2, 3 or more modifications to amino acids within the CDRs having suitable binding affinity to a target antigen polypeptide is employed. The anti-HNL antibodies disclosed herein can readily be modified by techniques well-known to one of ordinary skill in the art. Potential mutations include insertion, deletion or substitution of one or more residues. In some embodiment, insertions or deletions are in the range of about 1 to 5 amino acids, in the range of about 1 to 3 amino acids, or in the range of about 1 or 2 amino acids. Deletion variants are polypeptides wherein at least one amino acid residue of any amino acid sequence is removed. Deletions can be effected at one or both termini of the protein, or with removal of one or more residues within (i.e., internal to) the polypeptide. Methods for preparation of deletion variants are routine in the art. See, e.g., Sambrook et al. (1989) Molecular Cloning: A Laboratory Guide, Vols 1-3, Cold Spring Harbor Press, the disclosure of which is incorporated herein by reference in its entirety.

Amino acid sequence insertions include amino- and/or carboxyl-terminal fusions ranging in length from one residue to polypeptides containing hundreds or more residues, as well as internal sequence insertions of one or more amino acids. As with any of the different variant types described herein, insertional variants can be designed such that the resulting polypeptide retains the same biological properties or exhibits a new physical, chemical and/or biological property not associated with the parental polypeptide from which it was derived. Methods for preparation of insertion variants are also routine and well known in the art (Sambrook et al., supra).

Fusion proteins comprising a polypeptide comprising an anti-HNL antibody described herein, and a heterologous polypeptide, are a specific type of insertion variant contemplated herein. Nonlimiting examples of heterologous polypeptides which can be fused to polypeptides of interest include proteins with long circulating half-life, such as, but not limited to, immunoglobulin constant regions (e.g., Fc region); marker sequences that permit identification of the polypeptide of interest; sequences that facilitate purification of the polypeptide of interest; and sequences that promote formation of multimeric proteins. Methods of making antibody fusion proteins are well known in the art. See, e.g., U.S. Pat. No. 6,306,393, the disclosure of which is incorporated herein by reference in its entirety. In certain embodiments, fusion proteins are produced which may include a flexible linker, which connects the chimeric scFv antibody to the heterologous protein moiety. Appropriate linker sequences are those that do not affect the ability of the resulting fusion protein to be recognized and bind the epitope specifically bound by the V domain of the protein (see, e.g., WO 98/25965, the disclosure of which is incorporated herein by reference in its entirety).

Substitution variants are those in which at least one residue in the polypeptide amino acid sequence is removed and a different residue is inserted in its place. Modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. In certain embodiments, substitution variants are designed, i.e., one or more specific (as opposed to random) amino acid residues are substituted with a specific amino acid residue. Typical changes of these types include conservative substitutions and/or substitution of one residue for another based on similar properties of the native and substituting residues.

Conservative substitutions are shown below. The most conservative substitution is found under the heading of "preferred substitutions." If such substitutions result in no change in biological activity, then more substantial changes may be introduced and the products screened.

| Original | Exemplary | Preferred Substitutions |
| --- | --- | --- |
| Ala (A) | val; leu; ile; | val |
| Arg (R) | lys; gln; asn; | lys |
| Asn (N) | gln; his; asp, lys; | gln; arg |
| Asp (D) | glu; asn | glu |
| Cys (C) | ser; ala | ser |
| Gln (Q) | asn; glu | asn |
| Glu (E) | asp; gln | asp |
| Gly (G) | ala | |
| His (H) | asn; gln; lys; arg | |
| Ile (I) | leu; val; met; ala; leu; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | |
| Pro (P) | ala | |
| Ser (S) | thr | |
| Thr (T) | ser | |
| Trp (W) | tyr; phe | tyr |
| Tyr (Y) | trp; phe; thr; ser | phe |
| Val (V) | ile; leu; met; phe; ala; norleucine | leu |

Amino acid residues which share common side-chain properties are often grouped as follows:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

In certain instances, antibody variants are prepared with the intent to modify those amino acid residues which are directly involved in epitope binding. In other embodiments, modification of residues which are not directly involved in epitope binding or residues not involved in epitope binding in any way, is desirable, for purposes discussed herein. Mutagenesis within any of the CDR regions and/or framework regions is contemplated.

In order to determine which antibody amino acid residues are important for epitope recognition and binding, alanine scanning mutagenesis can be performed to produce substitution variants. See, for example, Cunningham et al., Science, 244: 1081-1085 (1989), the disclosure of which is incorporated herein by reference in its entirety. In this method, individual amino acid residues are replaced one-at-a-time with an alanine residue and the resulting anti-HNL antibody is screened for its ability to bind its specific epitope relative to the unmodified antibody. Modified antibodies with reduced binding capacity are sequenced to determine which residue was changed, indicating its significance in binding or biological properties.

Substitution variants of antibodies can be prepared by affinity maturation wherein random amino acid changes are introduced into the parent antibody sequence. See, for example, Ouwehand et al., Vox Sang 74 (Suppl 2):223-232, 1998; Rader et al., Proc. Natl. Acad. Sci. USA 95: 8910-8915, 1998; Dall'Acqua et al., Curr. Opin. Struct. Biol, 8: 443-450, 1998, the disclosures of which are incorporated herein by reference in their entireties. Affinity maturation involves preparing and screening the anti-HNL antibodies, or variants thereof and selecting from the resulting variants those that have modified biological properties, such as increased binding affinity relative to the parent anti-HNL antibody. A convenient way for generating substitutional variants is affinity maturation using phage display. Briefly, several hypervariable region sites are mutated to generate all possible amino substitutions at each site. The variants thus generated are expressed in a monovalent fashion on the surface of filamentous phage particles as fusions to the gene III product of Ml 3 packaged within each particle. The phage-displayed variants are then screened for their biological activity (e.g., binding affinity). See e.g., WO 92/01047, WO 93/112366, WO 95/15388 and WO 93/19172.

Current antibody affinity maturation methods belong to two mutagenesis categories: stochastic and nonstochastic. Error prone PCR, mutator bacterial strains (Low et al., J. Mol. Biol. 260, 359-68, 1996), and saturation mutagenesis (Nishimiya et al., J. Biol. Chem. 275: 12813-20, 2000; Chowdhury, P. S. Methods Mol. Biol. 178, 269-85, 2002) are typical examples of stochastic mutagenesis methods (Rajpal et al., Proc Natl Acad Sci USA. 102: 8466-71, 2005). Nonstochastic techniques often use alanine-scanning or site-directed mutagenesis to generate limited collections of specific muteins. Some methods are described in further detail below. Affinity maturation of recombinant antibodies is commonly performed through several rounds of panning of candidate antibodies in the presence of decreasing amounts of antigen. Decreasing the amount of antigen per round selects the antibodies with the highest affinity to the antigen thereby yielding antibodies of high affinity from a large pool of starting material. Affinity maturation via panning is well known in the art and is described, for example, in Huls et al. (Cancer Immunol Immunother. 50: 163-71, 2001). Methods of affinity maturation using phage display technologies are described elsewhere herein and known in the art (see e.g., Daugherty et al., Proc Natl Acad Sci USA, 91: 2029-34, 2000).

Look-through mutagenesis (LTM) (Rajpal et al., Proc Natl Acad Sci USA. 102: 8466-71, 2005) provides a method for rapidly mapping the antibody-binding site. For LTM, nine amino acids, representative of the major side-chain chemistries provided by the 20 natural amino acids, are selected to dissect the functional side-chain contributions to binding at every position in all six CDRs of an antibody. LTM generates a positional series of single mutations within a CDR where each "wild type" residue is systematically substituted by one of nine selected amino acids. Mutated CDRs are combined to generate combinatorial single-chain variable fragment (scFv) libraries of increasing complexity and size without becoming prohibitive to the quantitative display of all muteins. After positive selection, clones with improved binding are sequenced, and beneficial mutations are mapped.

Error-prone PCR involves the randomization of nucleic acids between different selection rounds. The randomization occurs at a low rate by the intrinsic error rate of the polymerase used but can be enhanced by error-prone PCR (Zaccolo et al., J. Mol. Biol. 285: 775-783, 1999) using a polymerase having a high intrinsic error rate during transcription (Hawkins et al., J Mol Biol. 226: 889-96, 1992). After the mutation cycles, clones with improved affinity for the antigen are selected using routine methods in the art.

Techniques utilizing gene shuffling and directed evolution may also be used to prepare and screen anti-HNL antibodies, or variants thereof, for desired activity. For example, Jermutus et al., Proc Natl Acad Sci USA., 98(1):75-80 (2001) showed that tailored in vitro selection strategies based on ribosome display were combined with in vitro diversification by DNA shuffling to evolve either the off-rate or thermodynamic stability of scFvs; Fermer et al., Tumour Biol. 2004 January-April; 25(1-2):7-13 reported that use of phage display in combination with DNA shuffling raised affinity by almost three orders of magnitude. Dougherty et al., Proc Natl Acad Sci USA. 2000 Feb. 29; 97(5):2029-2034 reported that (i) functional clones occur at an unexpectedly high frequency in hypermutated libraries, (ii) gain-of-function mutants are well represented in such libraries, and (iii) the majority of the scFv mutations leading to higher affinity correspond to residues distant from the binding site.

Alternatively, or in addition, it may be beneficial to analyze a crystal structure of the antigen-antibody complex to identify contact points between the antibody and antigen, or to use computer software to model such contact points. Such contact residues and neighboring residues are candidates for substitution according to the techniques elaborated herein. Once such variants are generated, they are subjected to screening as described herein and antibodies with superior properties in one or more relevant assays may be selected for further development.

In another aspect, a method is provided of detecting human HNL in a sample, comprising contacting a sample from a human with any of the aforementioned antibodies under conditions that allow binding of the antibody to human HNL, and detecting the bound antibody. In one embodiment, a first antibody to HNL is immobilized on a solid support, as a capture reagent, and a second antibody to HNL is used as a detection reagent. In a related aspect, the amount of HNL in the sample is quantitated by measuring the amount of the bound antibody. The detection methods can be used in a variety of diagnostic, prognostic and monitoring methods, including methods of diagnosing a HNL-related disorder, methods of differentiating an inflammatory disease from a noninflammatory disease and methods of monitoring therapy with an anti-HNL antibody. In such methods, a level of HNL above a certain threshold is correlated with the presence of HNL-related disorder, while a level below said threshold indicates that the patient is unlikely to have HNL-related disorder. Similarly, a level of HNL above a certain threshold is correlated with the presence of a bacterial infection, while a level below said threshold indicates that the patient is unlikely to have a bacterial infection. To determine the presence or absence of a bacterial infection, a biological sample from a patient is contacted with one or more of the anti-HNL antibodies disclosed herein under conditions and for a time sufficient to allow immunocomplexes to form.

Immunocomplexes formed between an anti-HNL antibody and HNL in the biological sample are then detected. The amount of HNL in the sample is quantitated by measuring the amount of the immunocomplex formed between the antibody and HNL. Within certain methods, a biological sample is isolated from a patient and is incubated with one or more of the anti-HNL antibodies disclosed herein, and the level of the antibody-HNL complex above a certain threshold is correlated with the presence of bacterial infection, and a level below said threshold indicates that the patient is unlikely to have bacterial infection.

For monitoring of therapy comprising re-testing a patient for the presence of HNL after initiation, during or after the therepy, aimed at fighting the bacterial infection, a level of HNL below a certain threshold indicates that the therapy (drug and/or dose) is effective, and a level above said threshold indicates that the therapy is not effective. Embodiments of the invention thus provide a method of (re-)testing subjects suspected to suffer from a bacterial infection (i.e. measuring HNL at different timepoints) comprising the steps:

Incubating a sample in the presence of said binding agent;
Optionally washing off unbound sample material;
Measuring the level of HNL in a sample from a subject suspected to have a bacterial infection, or having a confirmed bacterial infection and subject to antibiotic therapy;
Optionally comparing the level of HNL measured in step c) with one or more control samples, optionally obtained from
(i) healthy subjects,
(ii) subjects known to have a bacterial infection, and
further optionally comparing the level of HNL measured in step c) with one or more normalized control HNL values indicative for healthy subjects, and/or subjects with a bacterial infection, and/or the level of HNL in a sample from the patient before treatment, and wherein the level of HNL in sample from a subject diagnosed with bacterial disease is determined at least at one further point in time after starting an antibacterial treatment, optionally comprising repeating the said analysis, and further optionally comparing the HNL-level before, during and/or after antibacterial therapy.

In another embodiment the invention provides a method of monitoring the efficiency or non-efficiency of anti-bacterial treatment, e.g. with specific antibiotics, wherein said subject has been identified as a carrier of bacteria causing sepsis, and/or antibiotic resistant bacteria.

In any of the methods disclosed herein a pre-activator substance may be used to increase the sensitivity of the test methods, which is preferably an N-formyl peptide, more preferably the tri-peptide fMLP. Also preferably envisaged is the use of Protein A. The present invention further envisages the use of additional alternative neutrophil activators such as Lipopolysaccharide (LPS), platelet-activating factor, an unmethylated CpG oligodinucleotide, or tumor necrosis factor (TNF). These activators may be used alone or in any combination, for instance in the form of fMLP and/or Protein A and/or Lipopolysaccharide (LPS) and/or platelet-activating factor and/or an unmethylated CpG oligodinucleotide and/or tumor necrosis factor (TNF), such as e.g. fMLP in combination with Protein A, fMLP in combination with LPS, fMLP in combination with platelet-activating factor, fMLP in combination with unmethylated CpG oligodinucleotide, or in combination with TNF etc. Also envisaged are further combinations of activators such as Protein A in combination with LPS, Protein A in combination with platelet-activating factor, Protein A in combination with unmethylated CpG oligodinucleotide, or in combination with TNF; or LPS in combination with any of the other activators mentioned above; or unmethylated CpG oligodinucleotide in combination with any of the other activators mentioned above; or TNF in combination with any of the other activators mentioned above. In a preferred embodiment, the activator is fMLP, or a combination of fMLP with one or more of the other activators mentioned above.

Also provided are methods for differentiating a bacterial infection from a non-bacterial infection. Various immunoassays known in the art can be used, including but are not limited to: competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), Western blots, precipitation reactions, agglutination assays (e.g., gel agglutination assays, hemagglutination assays), immunofluorescence assays, protein A assays, and immunoelectrophoresis assays, etc., as well as, e.g. devices for detection of analytes that involve magnetic based separation of the analytes of interest (for example the device disclosed in WO2008/072156, WO2008/102218, WO2010/035204, and WO2011/036638, incorporated herein in their entireties). In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. Antibodies: A Laboratory Manual (1988) by Harlow & Lane or more recent editions; Immunoassays: A Practical Approach, Oxford University Press, Gosling, J. P. (ed.) (2001) or more recent editions; and/or Current Protocols in Molecular Biology (Ausubel et al.), which is regularly updated. Examples of such assays usually involve the antibody attached to a surface or matrix, patient serum added and time allowed for a complex to form; suitable washing procedures to remove unbound complex, followed by either the addition of a second antibody to allow detection of the complex (a sandwich ELISA) or a detectable version of HNL to detect free HNL binding sites on the antibody surface (a competition ELISA). The level of HNL, as detected by the foregoing methods, above a certain threshold is correlated with the presence of an inflammatory disease, and a level below said threshold indicates that the patient is unlikely to have an inflammatory disease. A patient is unlikely to have an bacterial infection disease when the HNL level is within the normal range. A patient is likely to have an bacterial disease when the HNL level exceeds the normal range.

In some embodiments, a biological sample obtained from a patient is tested for the level of HNL. The biological sample is incubated with one or more of the anti-HNL antibodies disclosed herein under conditions and for a time sufficient to allow immunocomplexes to form. Immunocomplexes formed between the HNL and antibodies in the biological sample that specifically bind to the HNL are then detected. A biological sample for use within such methods may be any sample obtained from a patient that is expected to contain HNL. Suitable biological samples include blood, serum plasma, urine, cerebrospinal fluid (CSF) and bone marrow. Suitable antibodies include antibodies from human cells, rodent, rabbit, goat, camel, or any other species.

The biological sample is incubated with antibodies in a reaction mixture under conditions and for a time sufficient to permit immunocomplexes to form between HNL and antibodies that are immunospecific for HNL. Following the incubation, the reaction mixture is tested for the presence of immunocomplexes. Detection of immunocomplexes formed between an anti-HNL antibody and HNL present in the biological sample may be accomplished by a variety of known techniques, such as radioimmunoassays (RIA) and enzyme linked immunosorbent assays (ELISA). Suitable assays are well known in the art and are amply described in the scientific and patent literature (Harlow and Lane, 1988). Assays that may be used include, but are not limited to, the double monoclonal antibody sandwich immunoassay technique (U.S. Pat. No. 4,376,110); monoclonal-polyclonal antibody sandwich assays (Wide L., "Solid Phase Antigen-Antibody Systems," Radioimmunoassay Methods: European Workshop Sep. 15-17 1970 Edinburgh, Kirkham and Hunter, eds., (Churchill Livingston, Edenburgh, (1971)) pp. 405-412; the "western blot" method (U.S. Pat. No. 4,452,901); immunoprecipitation of labeled ligand (Brown et al., J. Biol. Chem. 4980-4983 m 1980); enzyme-linked immunosorbent assays; immunocytochemical techniques, including the use of fluorochromes (Brooks et al., CHn. Exp. Immunol., 39: 477, 1980); and neutralization of activity (Bowen-Pope et al., Science, 226: 701-703,1984). Other immunoassays include, but are not limited to, those described in U.S. Pat. Nos. 3,850,752; 3,901,654; 3,935,074; 3,984,533; 3,996,345; 4,034,074; and 4,098,876. For detection purposes, an anti-HNL antibody may either be labeled or unlabeled. Unlabeled antibodies may be used in agglutination assays or in combination with labeled detection reagents that bind to the immunocomplexes (e.g., anti-immunoglobulin, protein G, Protein A or a lectin and secondary antibodies, or antigen-binding fragments thereof, capable of binding to the antibodies that specifically bind to the HNL). If the anti-HNL antibody is labeled, the reporter group may be any suitable reporter group known in the art, including radioisotopes, fluorescent groups (e.g. fluorescein or rhodamine), luminescent groups, enzymes, biotin and dye particles. Labels that are themselves directly detectable include fluorescent or luminescent dyes, metals or metal chelates, electrochemical labels, radionuclides (e.g., 32P, 14C, 1251, 3H, or 1311), magnetic labels or beads (e.g., DYNABEADS), paramagnetic labels, or colorimetric labels (e.g., colloidal gold, colored glass or plastic beads). Such detectable labels may be directly conjugated to the anti-HNL antibody or detection reagent or may be associated with a bead or particle that is attached to the anti-HNL antibody or detection reagent. Labels that are detectable through binding of a labeled specific binding partner include biotin, digoxigenin, maltose, oligohistidine, 2,4-dinitrobenzene, phenyl arsenate, ssDNA, or dsDNA). Indirect labels that can be indirectly detected by their production of a detectable reaction product include various enzymes well known in the art, such as alkaline phosphatase, horseradish peroxidase, β-galactosidase, xanthine oxidase, glucose oxidase or other saccharide oxidases, or luciferases, which cleave appropriate substrate to form a colored or fluorescent reaction product.

Within certain assays, an unlabeled anti-HNL antibody is immobilized on a solid support, for use as a "capture agent" (or reagent) that captures the HNL within a biological sample. The solid support may be any material known to those of ordinary skill in the art to which the antibody may be attached. For example, the solid support may be a test well in a microtiter plate or a nitrocellulose or other suitable membrane. Alternatively, the support may be a tube, bead, particle or disc, such as glass, fiberglass, latex or a plastic material such as polyethylene, polypropylene, polystyrene or polyvinylchloride or a porous matrix. Other materials include agarose, dextran, polyacrylamide, nylon, Sephadex, cellulose or polysaccharides. The support may also be a magnetic particle or a fiber optic sensor, such as those disclosed, for example, in U.S. Pat. No. 5,359,681. The immobilized anti-HNL antibody may be a polyclonal antibody, or one or more monoclonal antibodies such as those described herein, or a combination of polyclonal and one or more monoclonal antibodies. The antibody may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is contemplated. In such cases, adsorption may be achieved by contacting the anti-HNL antibody, in a suitable buffer, with the solid support for a suitable amount of time. The contact time varies with temperature, but is typically between about 1 hour and about 1 day. In general, contacting a well of a plastic microtiter plate (including polystyrene or polyvinylchloride) with an amount of peptide ranging from about 10 ng to about 10 µg, about 100 ng to about 1 µg, is sufficient to immobilize an adequate amount of peptide. Following immobilization, the remaining protein binding sites on the support are typically blocked. Any suitable blocking agent known to those of ordinary skill in the art, including bovine serum albumin, Tween™ 20 (Sigma Chemical Co., St. Louis, Mo.), heat-inactivated normal goat serum (NGS), or BLOTTO (buffered solution of nonfat dry milk which also contains a preservative, salts, and an antifoaming agent) can be used. The support is then incubated with a biological sample suspected of containing HNL. The sample can be applied neat, or, more often, it can be diluted, usually in a buffered solution which contains a small amount (0.1%-5.0%) by weight) of protein, such as BSA, NGS, or BLOTTO. In general, an appropriate contact time (i.e., incubation time) is a period of time that is sufficient to detect the presence of antibody or an antigen binding fragment that is immunospecific for the HNL within a sample containing HNL. In some embodiments, the contact time is sufficient to achieve a level of binding that is at least about 95% of that achieved at equilibrium between bound and unbound antibody or antibody fragment. Those of ordinary skill in the art will recognize that the time necessary to achieve equilibrium may be readily determined by assaying the level of binding that occurs over a period of time. At room temperature, an incubation time of about 10 to 30 minutes is generally sufficient.

Unbound sample may then be removed by washing the solid support with an appropriate buffer, such as PBS containing 0.1% Tween™ 20. A detection reagent that binds to the HNL in the immunocomplexes (formed by binding of the capture agent and the HNL from the sample) may then be added. Such detection reagent may be a polyclonal antibody, or one or more monoclonal antibodies such as those described herein, or a combination of polyclonal and one or more monoclonal antibodies such as those described herein or a Fab fraction of any antibody. The detection reagent may be directly labeled, i.e., comprises at least a first detectable label or "reporter" molecule. Alternatively, the detection reagent may be an unlabeled anti-HNL antibody. This unlabeled anti-HNL (primary) antibody is then detected by the binding of a labeled secondary antibody or reagent to the primary antibody. For example, if the primary antibody is a murine immunoglobulin, the secondary antibody may be a labeled anti-murine immunoglobulin antibody. Similarly, if the primary antibody is a rabbit immunoglobulin, the secondary antibody may be a labeled anti-rabbit immunoglobulin antibody.

The detection reagent is incubated with the immunocomplex for an amount of time sufficient to detect the bound antibody or antigen binding fragment thereof. An appropriate amount of time may generally be determined by assaying the level of binding that occurs over a period of time. Unbound label or detection reagent is then removed and bound label or detection reagent is detected using a suitable assay or analytical instrument. The method employed for detecting the reporter group depends upon the nature of the reporter group. For radioactive labels, scintillation counting or autoradiographic methods are generally appropriate. Spectroscopic methods may be used to detect dyes, luminescent or chemiluminescent moieties and various chromogens, fluorescent labels and such like. Biotin may be detected using avid in, coupled to a different reporter group (commonly a radioactive or fluorescent group or an enzyme). Enzyme reporter groups (including horseradish peroxidase, [beta]-galactosidase, alkaline phosphatase and glucose oxidase) may generally be detected by the addition of substrate (generally for a specific period of time), followed by spectroscopic or other analysis of the reaction products. Regardless of the specific method employed, a level of bound detection reagent that is at least two fold greater than background (i.e., the level observed for a biological sample obtained from an individual with a normal level of HNL) indicates the presence of a disorder associated with expression of HNL.

In alternative embodiments, the sample and detection reagent may be contacted simultaneously with the capture agent, rather than sequentially added. In yet another alternative, the sample and detection reagent may be pre-incubated together, then added to the capture agent. Other variations are readily apparent to one of ordinary skill in the art.

In another embodiment, the amount of HNL present in a sample is determined by a competitive binding assay. Competitive binding assays rely on the ability of a labeled standard (e.g., a HNL polypeptide, or an immunologically reactive portion thereof) to compete with the test sample analyte (a HNL polypeptide) for binding with a limited amount of an anti-HNL antibody. Following separation of free and bound HNL, the HNL is quantitated by relating ratio of bound/unbound HNL to known standards. The amount of a HNL polypeptide in the test sample is inversely proportional to the amount of Standard that becomes bound to the antibodies. To facilitate determining the amount of Standard that becomes bound, the antibodies typically are immobilized on a solid support so that the Standard and analyte that are bound to the antibodies may conveniently be separated from the standard and analyte which remain unbound. Thus, in such embodiments, also contemplated is contacting a biological sample with labeled mature HNL (or a labeled fragment thereof that retains the antigenicity of HNL) and an antibody that binds to mature HNL, and detecting the amount of antibody-labeled HNL complex formed.

Preparation of conjugates to solid supports or detectable labels often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, whereas pyridyl disulfides react with sulfhydryls to produce mixed disulfides. The pyridyl disulfide product is cleavable.

Heterobifunctional cross-linkers possess two or more different reactive groups that allow for sequential conjugations with specific groups of proteins, minimizing undesirable polymerization or self-conjugation. Heterobifunctional reagents are also used when modification of amines is problematic. Amines may sometimes be found at the active sites of macromolecules, and the modification of these may lead to the loss of activity. Other moieties such as sulfhydryls, carboxyls, phenols and carbohydrates may be more appropriate targets. A two-step strategy allows for the coupling of a protein that can tolerate the modification of its amines to a protein with other accessible groups. A variety of heterobifunctional cross-linkers, each combining different attributes for successful conjugation, are commercially available. Cross-linkers that are amine-reactive at one end and sulfhydryl-reactive at the other end are quite common. If using heterobifunctional reagents, the most labile group is typically reacted first to ensure effective cross-linking and avoid unwanted polymerization.

In some embodiments, methods for monitoring the effectiveness of therapy with an antibiotic include monitoring changes in the level of HNL in a sample, or in an animal, e.g. a mammal, for example a human patient. Methods in which HNL levels are monitored may comprise (a) incubating a first biological sample, obtained from a patient prior to a therapy with one or more of the anti-HNL antibodies disclosed herein, wherein the incubation is performed under conditions and for a time sufficient to allow immunocomplexes to form; (b) detecting immunocomplexes formed between the HNL in the biological sample and antibodies or antigen binding fragments that specifically bind HNL; and (c) repeating steps (a) and (b) using a second biological sample taken from the patient at later time, such as for example, following therapy with one or more antibiotics; and (d) comparing the number of immunocomplexes detected in the first and second biological samples. A biological sample for use within such methods may be any sample obtained from a patient that would be expected to contain HNL. Exemplary biological samples include blood, plasma, serum, urine, CSF, bone marrow, saliva, and sputum. A first biological sample may be obtained prior to initiation of therapy or part way through a therapy regime. The second biological sample should be obtained in a similar manner, but at a time following additional therapy. The second biological sample may be obtained at the completion of, or part way through, therapy, provided that at least a portion of therapy takes place between the isolation of the first and second biological samples. Incubation and detection procedures for both samples may generally be performed as described above. A decrease in the number of immunocomplexes in the second sample relative to the first sample indicates a decrease in HNL levels and reflects successful therapy.

Methods of setting an appropriate threshold for diagnosis of the disease states described herein and therapy monitoring as described herein are well known in the art. By way of example, levels of HNL in a sample from a sufficient representative number of normal subjects (e.g. healthy population without the condition to be detected) are analyzed relative to the HNL level from a sufficient representative number of diseased subjects (e.g. population confirmed to have the disease or condition) using the same protocols. A threshold cutoff can be determined that differentiates most of the normal population from most of the diseased population. Alternatively, useful end point values for negative, uncertain and positive results can be determined from the data. For example, a normal range (indicative of a negative result) can be determined, which includes HNL of most of the normal population but which exclude almost all of the diseased population. Correspondingly, a range indicative of a positive result can be determined, which includes HNL of most of the diseased population but which exclude almost all of the normal population. Appropriate endpoint values for the threshold may be determined to optimize the desired specificity or sensitivity, and may also take account of overall medical and epidemiological factors. Factors to be considered include the clinical objective of the IVD test and whether it is necessary to have a high positive predictive value, or a high negative predictive value, as well as prevalence of the disease in the tested population.

The present invention further relates to methods of ruling out a bacterial infection, methods of ruling out a viral infection, methods of ruling in a bacterial infection and methods of ruling in a viral infection in a subject. In general, HNL polypeptide concentration in a sample of a patient having a bacterial infection is higher than in a healthy patient sample, or in a sample of a patient having a viral infection. By "ruling in" an infection is accordingly meant that the subject has that type of infection. By "ruling out" an infection it is meant that the subject does not have that type of infection.

For example, HNL polypeptide concentration in a sample of a patient having a bacterial infection is considered higher than in a healthy patient sample when it exceeds a threshold of one and one-half standard deviations above the mean of the concentration as compared to the healthy patient population. Preferably, HNL polypeptide concentration in a patient sample is higher when the HNL concentration exceeds a threshold of two standard deviations above the mean of the concentration as compared to the healthy patient population. More preferably, HNL polypeptide concentration in a patient sample is higher when the HNL concentration exceeds a threshold of three standard deviations above the mean of the concentration as compared to the healthy patient population.

The present invention, in certain embodiments, is thus directed to the diagnosis of bacterial infection (i.e., ruling in a bacterial infection) by comparing the total concentration of HNL polypeptide in the patient biological sample to a statistically validated threshold for total HNL polypeptide and by comparing the determinant concentration in the patient biological sample to a statistically validated threshold for each specific determinant(s). The statistically validated threshold for total HNL polypeptide is based upon the total concentration of HNL polypeptide in comparable samples obtained from a control population, e.g., from healthy patients, or patients having a disease other than bacterial infection, e.g. a viral infection. The statistically validated threshold for the determinant concentration in the specific determinant(s) is based upon the determinant concentration in each specific determinant(s) in comparable control biological samples from a control population, e.g., from healthy patients, or patients having a disease other than bacterial infection. Various control populations are otherwise described herein.

The present invention, in certain embodiments, is further directed to the ruling out a bacterial infection by comparing the total concentration of HNL polypeptide in the patient biological sample to a statistically validated threshold for total HNL polypeptide and by comparing the determinant concentration in the patient biological sample to a statistically validated threshold for each specific determinant(s). The statistically validated threshold for total HNL polypeptide is based upon the total concentration of HNL polypeptide in comparable samples obtained from a control population, e.g., from patients having a bacterial infection. The statistically validated threshold for the determinant concentration in the specific determinant(s) is based upon the determinant concentration in each specific determinant(s) in comparable control biological samples from a control population, e.g., from patients having a bacterial infection. Various control populations are otherwise described herein.

Methods for of ruling out a bacterial infection, methods of ruling out a viral infection, methods of ruling in a bacterial infection and methods of ruling in a viral infection in a subject may essentially comprise the following steps:
    a) measuring the polypeptide concentration of HNL in a sample obtained from a subject using a binding agent as defined herein above, or a diagnostic composition or kit as defined herein above; and
    b) (i) ruling out a bacterial infection for the subject if the polypeptide concentration of HNL determined in step (a) is lower than a pre-determined first threshold value; or
    b) (ii) ruling out a viral infection for the subject if the polypeptide concentration of HNL determined in step (a) is higher than a pre-determined first threshold value; or
    b) (iii) ruling in a bacterial infection for the subject if the polypeptide concentration of HNL determined in step (a) is higher than a pre-determined first threshold value; or
    b) (iv) ruling in a viral infection for the subject if the polypeptide concentration of HNL determined in step (a) is lower than a pre-determined first threshold value.

In the context of ruling out a bacterial infection, the pre-determined first threshold may be a statistically validated threshold for total HNL polypeptide, which is based on a total concentration of HNL polypeptide in comparable control biological samples from patients having a bacterial infection.

In the context of ruling out a viral infection, the pre-determined first threshold may be a statistically validated threshold for total HNL polypeptide, which is based on a total concentration of HNL polypeptide in comparable control biological samples from patients having a having a viral infection.

In the context of ruling in a bacterial infection, the pre-determined first threshold may be a statistically validated threshold for total HNL polypeptide, which is based on a total concentration of HNL polypeptide in comparable control biological samples from healthy patients or patients having a viral infection.

In the context of ruling in a viral infection, the predetermined first threshold may be a statistically validated threshold for total HNL polypeptide, which is based on a total concentration of HNL polypeptide in comparable control biological samples from healthy patients or patients having a bacterial infection.

According to a further aspect, the invention relates to a method of providing a treatment recommendation for a subject comprising: a) measuring the polypeptide concentration of HNL in a sample obtained from a subject using a binding agent as defined above, or a diagnostic composition or kit as defined above; and
b) recommending that the subject receives an antibiotic treatment if the polypeptide concentration of HNL determined in step (a) is higher than a pre-determined threshold value;
c) recommending that the patient does not receive an antibiotic treatment if the polypeptide concentration of HNL determined in step (a) is lower than a predetermined threshold value; or
d) recommending that the patient receive an anti-viral treatment if the polypeptide concentration of HNL determined in step (a) is lower than a pre-determined threshold value as defined herein above.

Furthermore, the present invention relates to a method of providing a diagnostic test recommendation for a subject comprising:
a) measuring the polypeptide concentration of HNL in a sample obtained from a subject using a binding agent as defined above, or a diagnostic composition or kit as defined above; and
b) recommending testing the sample for the presence of bacteria if the polypeptide concentration of HNL determined in step (a) is higher than a pre-determined threshold value; or
c) recommending testing the sample for the presence of a virus if the polypeptide concentration of HNL determined in step (a) is lower than a pre-determined threshold value.

The statistically validated thresholds are related to the values used to characterize both the total HNL concentration and the concentration of one or more specific other determinant(s) in the biological sample obtained from the subject or patient. Thus, if the total HNL concentration or the determinant concentration is an absolute value, then the control value is also based upon an absolute value. Other determinants can be any markers, e.g. polypeptide markers or secondary markers, which have a predicte value on the determination of an infection as defined herein. For these other determinants the above provided definitions concerning the pre-determined threshold values apply accordingly. "Determinants" in the context of the present invention encompass, without limitation, polypeptides, peptide, proteins, protein isoforms (e.g. decoy receptor isoforms). Determinants can also include mutated proteins.

"Determinant" or "determinants" may accordingly encompass one or more of all polypeptides whose levels are changed in subjects who have an infection. Exemplary individual determinants may include TRAIL, IL1RA, IP 10, Mac-2BP, B2M, BCA-1, CHI3L1, Eotaxin, IL1a, MCP, CD62L, VEGFR2, CHP, CMPK2, CORO1C, EIF2AK2, ISG15, RPL22L1, RTN3, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, IgG non-specific bound molecules, IL1,1-TAC, TNFR1, ABTB1, ADIPOR1, ARHGDIB, ARPC2, ATP6V0B, C1orf83, CD15, CES1, COROIA, CRP, CSDA, EIF4B, EPSTI1, GAS 7, HERC5, IFI6, KIAA0082, IFIT1, IFIT3, IFITM1, IFITM3, LIPT1, IL7R, ISG20, LOC26010, LY6E, LRDD, LTA4H, MAN1C1, MBOAT2, MX1, NPM1, OAS2, PARP12, PARP9, QARS, RAB13, RAB31, RAC2, RPL34, PDIA6, PTEN, RSAD2, SART3, SDCBP, TRIM 22, SMAD9, SOCS3, UBE2N, XAF1 or ZBP1; as well as any combination thereof, e.g. more than 1, such as 2, 3, 4, 5, 6, 7, 8, 9, 10, 11, 12, 13, 14, 15, 16, 17, 18, 19, 20 or more or all of these determinants. The present invention further envisages the provision and/or use of binding agents against any of the above mentioned determinants, in particular if present as polypeptides, but in certain embodiments also including nucleic acid binding molecules. Such a binding agent, preferably an antibody, would be obtainable according to procedures known to the skilled person or outlined herein in the context of HNL, or would be available from commercial sources. Further information may be derived, for example, from Kjeldsen et al., J Biol Chem., 1993 May 15; 268(14): 10425-32, "Isolation and primary structure of NGAL, a novel protein associated with human neutrophil gelatinase".

Determinants may also encompass non-polypeptide factors, non-blood borne factors or non-analyte physiological markers of health status, such as "clinical parameters" defined herein, as well as "traditional laboratory risk factors", also defined herein.

For example, as used herein, determinants may include non-polypeptide features (i.e. non-polypeptide determinants) such as neutrophil % (abbreviated Neu (%)), lymphocyte % (abbreviated Lym (%)), monocyte % (abbreviated Mon(%)), absolute neutrophil count (abbreviated ANC) and absolute lymphocyte count (abbreviated ALC), white blood count (abbreviated WBC), age, gender, and maximal temperature (i.e. maximal core body temperature since initial appearance of symptoms).

Determinants may also include any calculated indices created mathematically or combinations of any one or more of the foregoing measurements, including temporal trends and differences. Where available, and unless otherwise described herein, determinants which are gene products are identified based on the official letter abbreviation or gene symbol assigned by the international Human Genome Organization Naming Committee (HGNC) and listed at the date of this filing at the US National Center for Biotechnology Information (NCBI) web site, also known as Entrez Gene. In preferred embodiments, determinants include polypeptide and non-polypeptide features.

Examples of such determinants as mentioned above and envisaged by the present invention are provided in the following:

ABTB1: This gene encodes a protein with an ankyrin repeat region and two BTB/POZ domains, which are thought to be involved in protein-protein interactions. Expression of this gene is activated by the phosphatase and tensin homolog, a tumor suppressor. Alternate splicing results in three transcript variants. It may act as a mediator of the PTEN growth-suppressive signaling pathway. It may play a role in developmental processes. The amino acid and/or nucleotide sequence of this determinant would be know to the skilled person or can be derived from suitable database entries, e.g. at Genbank or Uniprot with date of Nov. 11, 2015.

ADIPOR1: ADIPOR1 is a receptor for globular and full-length adiponectin (APM1), an essential hormone secreted by adipocytes that acts as an antidiabetic. It is probably involved in metabolic pathways that regulate lipid metabolism such as fatty acid oxidation. It mediates increased AMPK, PPARA ligand activity, fatty acid oxidation and glucose uptake by adiponectin. ADIPOR1 has some high-affinity receptors for globular adiponectin and low-affinity receptors for full-length adiponectin. The amino acid and/or nucleotide sequence of this determinant would be know to the skilled person or can be derived from suitable database entries, e.g. at Genbank or Uniprot with date of Nov. 11, 2015.

ARHGDIB: Regulates the GDP/GTP exchange reaction of the Rho proteins by inhibiting the dissociation of GDP from them, and the subsequent binding of GTP to them. The amino acid and/or nucleotide sequence of this determinant would be know to the skilled person or can be derived from suitable database entries, e.g. at Genbank or Uniprot with date of Nov. 11, 2015.

ARPC2: Functions as actin-binding component of the Arp2/3 complex which is involved in regulation of actin polymerization and together with an activating nucleation-promoting factor (NPF) mediates the formation of branched actin networks. Seems to contact the mother actin filament. The amino acid and/or nucleotide sequence of this determinant would be know to the skilled person or can be derived from suitable database entries, e.g. at Genbank or Uniprot with date of Nov. 11, 2015.

ATP6V0B: H<+>—ATPase (vacuolar ATPase, V-ATPase) is an enzyme transporter that functions to acidify intracellular compartments in eukaryotic cells. It is ubiquitously expressed and is present in endomembrane organelles such as vacuoles, lysosomes, endosomes, the Golgi apparatus, chromaffin granules and coated vesicles, as well as in the plasma membrane. H<+>-ATPase is a multi-subunit complex composed of two domains. The VI domain is responsible for ATP hydrolysis and the V0 domain is responsible for protein translocation. There are two main mechanisms of regulating H<+>-ATPase activity; recycling of H<+>-ATPase-containing vesicles to and from the plasma membrane and glucose-sensitive assembly/disassembly of the holoenzyme complex. These transporters play an important role in processes such as receptor-mediated endocytosis, protein degradation and coupled transport. They have a function in bone reabsorption and mutations in the A3 gene cause recessive osteopetrosis. Furthermore, H<+>-ATPases have been implicated in tumor metastasis and regulation of sperm motility and maturation. The amino acid and/or nucleotide sequence of this determinant would be know to the skilled person or can be derived from suitable database entries, e.g. at Genbank or Uniprot with date of Nov. 11, 2015.

B2M: additional alias of B2M include without limitation beta-2-microglobulin and CDABP0092. B2M is a component of MHC class I molecules, which are present on all nucleated cells. The protein encoded by this gene also encodes an isoform present in the serum. The protein has a predominantly beta-pleated sheet structure that can form amyloid fibrils in some pathological conditions. The amino acid and/or nucleotide sequence of this determinant would be know to the skilled person or can be derived from suitable database entries, e.g. at Genbank or Uniprot with date of Nov. 11, 2015.

BCA1: BCA1 is a B lymphocyte chemoattractant, independently cloned and named Angie, is a CXC chemokine strongly expressed in the follicles of the spleen, lymph nodes, and Peyer's patches. It preferentially promotes the migration of B lymphocytes (compared to T cells and macrophages), apparently by stimulating calcium influx into, and chemotaxis of, cells expressing Burkitt's lymphoma receptor 1 (BLR-1). It may therefore function in the homing of B lymphocytes to follicles (provided by RefSeq). The amino acid and/or nucleotide sequence of this determinant would be know to the skilled person or can be derived from suitable database entries, e.g. at Genbank or Uniprot with date of Nov. 11, 2015.

C1orf83: Function not fully characterized. The amino acid and/or nucleotide sequence of this determinant would be know to the skilled person or can be derived from suitable database entries, e.g. at Genbank or Uniprot with date of Nov. 11, 2015.

CD112: This gene encodes a single-pass type I membrane glycoprotein with two Ig-like C2-type domains and an Ig-like V-type domain. This protein is one of the plasma membrane components of adherens junctions. It also serves as an entry for certain mutant strains of herpes simplex virus and pseudorabies virus, and it is involved in cell to cell spreading of these viruses. Variations in this gene have been associated with differences in the severity of multiple sclerosis. Alternate transcriptional splice variants, encoding different isoforms, have been characterized. The amino acid and/or nucleotide sequence of this determinant would be know to the skilled person or can be derived from suitable database entries, e.g. at Genbank or Uniprot with date of Nov. 11, 2015.

CD 134: The protein encoded by this gene is a member of the TNF-receptor superfamily. This receptor has been shown to activate NF-kappaB through its interaction with adaptor proteins TRAF2 and TRAF5. Knockout studies in mice suggested that this receptor promotes the expression of apoptosis inhibitors BCL2 and BCL21L1/BCL2-XL, and thus suppresses apoptosis. The knockout studies also suggested the roles of this receptor in CD4+ T cell response, as well as in T cell-dependent B cell proliferation and differentiation. The amino acid and/or nucleotide sequence of this determinant would be know to the skilled person or can be derived from suitable database entries, e.g. at Genbank or Uniprot with date of Nov. 11, 2015.

CD 15 (FUT4): The product of this gene transfers fucose to N-acetyllactosamine polysaccharides to generate fucosylated carbohydrate structures. It catalyzes the synthesis of the non-sialylated antigen, Lewis x (CD 15). The amino acid and/or nucleotide sequence of this determinant would be know to the skilled person or can be derived from suitable database entries, e.g. at Genbank or Uniprot with date of Nov. 11, 2015.

CD 182: The protein encoded by this gene is a member of the G-protein-coupled receptor family. This protein is a receptor for interleukin 8 (IL8). It binds to IL8 with high affinity, and transduces the signal through a G-protein activated second messenger system. This receptor also binds to chemokine (C-X-C motif) ligand 1 (CXCL1/MGSA), a protein with melanoma growth stimulating activity, and has been shown to be a major component required for serum-dependent melanoma cell growth. This receptor mediates neutrophil migration to sites of inflammation. The angiogenic effects of IL8 in intestinal microvascular endothelial cells are found to be mediated by this receptor. Knockout studies in mice suggested that this receptor controls the positioning of oligodendrocyte precursors in developing spinal cord by arresting their migration. This gene, IL8RA, a gene encoding another high affinity IL8 receptor, as well as IL8RBP, a pseudogene of IL8RB, form a gene cluster in a region mapped to chromosome 2q33-q36. Alternatively spliced variants, encoding the same protein, have been identified. The amino acid and/or nucleotide sequence of this determinant would be know to the skilled person or can be derived from suitable database entries, e.g. at Genbank or Uniprot with date of Nov. 11, 2015.

CD231: The protein encoded by this gene is a member of the transmembrane 4 superfamily, also known as the tetraspanin family. Most of these members are cell-surface proteins that are characterized by the presence of four hydrophobic domains. The proteins mediate signal transduction events that play a role in the regulation of cell development, activation, growth and motility. This encoded protein is a cell surface glycoprotein and may have a role in the control of neurite outgrowth. It is known to complex with integrins. This gene is associated with X-linked mental retardation and neuropsychiatric diseases such as Huntington's chorea, fragile X syndrome and myotonic dystrophy (provided by RefSeq). [000121] CD235a: CD235a is the major intrinsic membrane protein of the erythrocyte. The N-terminal glycosylated segment, which lies outside the erythrocyte membrane, has M blood group receptors. Appears to be important for the function of SLC4A1 and is required for high activity of SLC4A1. May be involved in translocation of SLC4A1 to the plasma membrane. Is a receptor for influenza virus. Is a receptor for Plasmodium falciparum erythrocyte-binding antigen 175 (EBA-175); binding of EB A-175 is dependent on sialic acid residues of the O-linked glycans. Appears to be a receptor for Hepatitis A virus (HAV). The amino acid and/or nucleotide sequence of this determinant would be know to the skilled person or can be derived from suitable database entries, e.g. at Genbank or Uniprot with date of Nov. 11, 2015.

CD335: Cytotoxicity-activating receptor that may contribute to the increased efficiency of activated natural killer (K) cells to mediate tumor cell lysis. The amino acid and/or nucleotide sequence of this determinant would be know to the skilled person or can be derived from suitable database entries, e.g. at Genbank or Uniprot with date of Nov. 11, 2015.

CD337: The protein encoded by this gene is a natural cytotoxicity receptor (NCR) that may aid NK cells in the lysis of tumor cells. The encoded protein interacts with CD3-zeta (CD247), a T-cell receptor. A single nucleotide polymorphism in the 5' untranslated region of this gene has been associated with mild malaria susceptibility. Three transcript variants encoding different isoforms have been found for this gene. The amino acid and/or nucleotide sequence of this determinant would be know to the skilled person or can be derived from suitable database entries, e.g. at Genbank or Uniprot with date of Nov. 11, 2015.

CD45: The protein encoded by this gene is a member of the protein tyrosine phosphatase (PTP) family. PTPs are known to be signaling molecules that regulate a variety of cellular processes including cell growth, differentiation, mitotic cycle, and oncogenic transformation. This PTP contains an extracellular domain, a single transmembrane segment and two tandem intracytoplasmic catalytic domains, and thus belongs to receptor type PTP. This gene is specifically expressed in hematopoietic cells. This PTP has been shown to be an essential regulator of T- and B-cell antigen receptor signaling. It functions through either direct interaction with components of the antigen receptor complexes, or by activating various Src family kinases required for the antigen receptor signaling. This PTP also suppresses JAK kinases, and thus functions as a regulator of cytokine receptor signaling. Several alternatively spliced transcripts variants of this gene, which encode distinct isoforms, have been reported. The amino acid and/or nucleotide sequence of this determinant would be know to the skilled person or can be derived from suitable database entries, e.g. at Genbank or Uniprot with date of Nov. 11, 2015.

CD49d: The product of this gene belongs to the integrin alpha chain family of proteins. Integrins are heterodimeric integral membrane proteins composed of an alpha chain and a beta chain. This gene encodes an alpha 4 chain. Unlike other integrin alpha chains, alpha 4 neither contains an I-domain, nor undergoes disulfide-linked cleavage. Alpha 4 chain associates with either beta 1 chain or beta 7 chain. The amino acid and/or nucleotide sequence of this determinant would be know to the skilled person or can be derived from suitable database entries, e.g. at Genbank or Uniprot with date of Nov. 11, 2015.

CD62L: This gene encodes a cell surface adhesion molecule that belongs to a family of adhesion/homing receptors. The encoded protein contains a C-type lectin-like domain, a calcium-binding epidermal growth factor-like domain, and two short complement-like repeats. The gene product is required for binding and subsequent rolling of leucocytes on endothelial cells, facilitating their migration into secondary lymphoid organs and inflammation sites. Single-nucleotide polymorphisms in this gene have been associated with various diseases including immunoglobulin A nephropathy. Alternatively spliced transcript variants have been found for this gene (provided by RefSeq). The protein encoded by this gene has a soluble form denoted sCD62L. The amino acid and/or nucleotide sequence of this determinant would be know to the skilled person or can be derived from suitable database entries, e.g. at Genbank or Uniprot with date of Nov. 11, 2015.

CD64: This gene encodes an integral membrane glycoprotein known as an Fc receptor that binds monomeric IgG-type antibodies with high affinity. Structurally CD64 is composed of a signal peptide that allows its transport to the surface of a cell, three extracellular immunoglobulin domains of the C2-type that it uses to bind antibody, a hydrophobic transmembrane domain, and a short cytoplasmic tail. CD64 is constitutively found on only macrophages and monocytes. Treatment of polymorphonuclear leukocytes with cytokines like IFNγ and G-CSF can induce CD64 expression on these cells. The amino acid and/or nucleotide sequence of this determinant would be know to the skilled person or can be derived from suitable database entries, e.g. at Genbank or Uniprot with date of Nov. 11, 2015

CD66a: This gene encodes a member of the carcinoembryonic antigen (CEA) gene family, which belongs to the immunoglobulin superfamily. Two subgroups of the CEA family, the CEA cell adhesion molecules and the pregnancy-specific glycoproteins, are located within a 1.2 Mb cluster on the long arm of chromosome 19. Eleven pseudogenes of the CEA cell adhesion molecule subgroup are also found in the cluster. The encoded protein was originally described in bile ducts of liver as biliary glycoprotein. Subsequently, it was found to be a cell-cell adhesion molecule detected on leukocytes, epithelia, and endothelia. The encoded protein mediates cell adhesion via homophilic as well as heterophilic binding to other proteins of the subgroup. Multiple cellular activities have been attributed to the encoded protein, including roles in the differentiation and arrangement of tissue three-dimensional structure, angiogenesis, apoptosis, tumor suppression, metastasis, and the modulation of innate and adaptive immune responses. Multiple transcript variants encoding different isoforms have been reported. The amino acid and/or nucleotide sequence of this determinant would be know to the skilled person or can be derived from suitable database entries, e.g. at Genbank or Uniprot with date of Nov. 11, 2015.

CD66c: Carcinoembryonic antigen (CEA; MIM 1 14890) is one of the most widely used tumor markers in serum immunoassay determinations of carcinoma. An apparent lack of absolute cancer specificity for CEA probably results in part from the presence in normal and neoplastic tissues of antigens that share antigenic determinants with the 180-kD form of CEA (Barnett et al, 1988 (PubMed 3220478)). For background information on the CEA family of genes, see CEACAM1 (MIM 109770). The amino acid and/or nucleotide sequence of this determinant would be know to the skilled person or can be derived from suitable database entries, e.g. at Genbank or Uniprot with date of Nov. 11, 2015.

CD66d: This gene encodes a member of the family of carcinoembryonic antigen-related cell adhesion molecules (CEACAMs), which are used by several bacterial pathogens to bind and invade host cells. The encoded transmembrane protein directs phagocytosis of several bacterial species that is dependent on the small GTPase Rac. It is thought to serve an important role in controlling human-specific pathogens by the innate immune system. Alternatively spliced transcript variants have been described, but their biological validity has not been determined. The amino acid and/or nucleotide sequence of this determinant would be know to the skilled person or can be derived from suitable database entries, e.g. at Genbank or Uniprot with date of Nov. 11, 2015.

CD66e: CD66e, a member of the CEACAM subfamily, serves as a surface glycoprotein that plays a role in cell adhesion and in intracellular signaling. CD66e also serves a receptor for *E. coli* Dr adhesins. The amino acid and/or nucleotide sequence of this determinant would be know to the skilled person or can be derived from suitable database entries, e.g. at Genbank or Uniprot with date of Nov. 11, 2015.

CD73: The protein encoded by this gene is a plasma membrane protein that catalyzes the conversion of extracellular nucleotides to membrane-permeable nucleosides. The encoded protein is used as a determinant of lymphocyte differentiation. Defects in this gene can lead to the calcification of joints and arteries. Two transcript variants encoding different isoforms have been found for this gene. The amino acid and/or nucleotide sequence of this determinant would be know to the skilled person or can be derived from suitable database entries, e.g. at Genbank or Uniprot with date of Nov. 11, 2015.

CD84: CD84 plays a role as adhesion receptor functioning by homophilic interactions and by clustering. Recruits SH2 domain-containing proteins SH2D1 A SAP. Increases proliferative responses of activated T-cells and SH2D1A SAP does not seen be required for this process. Homophilic interactions enhance interferon gamma/IFNG secretion in lymphocytes and induce platelet stimulation via a SH2D1 A/SAP-dependent pathway. CD84 may also serve as a marker for hematopoietic progenitor cells. The amino acid and/or nucleotide sequence of this determinant would be know to the skilled person or can be derived from suitable database entries, e.g. at Genbank or Uniprot with date of Nov. 11, 2015.

CD8A: The CD8 antigen is a cell surface glycoprotein found on most cytotoxic T lymphocytes that mediates efficient cell-cell interactions within the immune system. The CD8 antigen acts as a corepressor with the T-cell receptor on the T lymphocyte to recognize antigens displayed by an antigen presenting cell (APC) in the context of class I MHC molecules. The coreceptor functions as either a homodimer composed of two alpha chains, or as a heterodimer composed of one alpha and one beta chain. Both alpha and beta chains share significant homology to immunoglobulin variable light chains. This gene encodes the CD8 alpha chain isoforms. Multiple transcript variants encoding different isoforms have been found for this gene. The amino acid and/or nucleotide sequence of this determinant would be know to the skilled person or can be derived from suitable database entries, e.g. at Genbank or Uniprot with date of Nov. 11, 2015.

CES1: Involved in the detoxification of xenobiotics and in the activation of ester and amide prodrugs. Hydrolyzes aromatic and aliphatic esters, but has no catalytic activity toward amides or a fatty acyl-CoA ester. Hydrolyzes the methyl ester group of cocaine to form benzoylecgonine. Catalyzes the transesterification of cocaine to form cocaethylene. Displays fatty acid ethyl ester synthase activity, catalyzing the ethyl esterification of oleic acid to ethyloleate. The amino acid and/or nucleotide sequence of this determinant would be know to the skilled person or can be derived from suitable database entries, e.g. at Genbank or Uniprot with date of Nov. 11, 2015.

CHI3L1: chitinase 3-like 1 (cartilage glycoprotein-39); additional aliases of CHI3L1 include without limitation ASRT7, CGP-39, GP-39, GP39, HC-gp39, HCGP-3P, YKL-40, YKL40, YYL-40 and hCGP-39. Chitinases catalyze the hydrolysis of chitin, which is an abundant glycopolymer found in insect exoskeletons and fungal cell walls. The glycoside hydrolase 18 family of chitinases includes eight human family members. This gene encodes a glycoprotein member of the glycosyl hydrolase 18 family that lacks chitinase activity can be secreted by activated macrophages, chondrocytes, neutrophils and synovial cells. CHI3L1 inhibits oxidant-induced lung injury, augments adaptive Th2 immunity, regulates apoptosis, stimulates alternative macrophage activation, and contributes to fibrosis and wound healing. The amino acid and/or nucleotide sequence of this determinant would be know to the skilled person or can be derived from suitable database entries, e.g. at Genbank or Uniprot with date of Nov. 11, 2015.

CHP: This gene encodes a phosphoprotein that binds to the Na+/H+ exchanger NHE1. This protein serves as an essential cofactor which supports the physiological activity of NHE family members and may play a role in the mitogenic regulation of NHE1. The protein shares similarity with calcineurin B and calmodulin and it is also known to be an endogenous inhibitor of calcineurin activity (provided by RefSeq). The amino acid and/or nucleotide sequence of this determinant would be know to the skilled person or can be derived from suitable database entries, e.g. at Genbank or Uniprot with date of Nov. 11, 2015.

CMPK2: This gene encodes a protein that may participate in dUTP and dCTP synthesis in mitochondria. Is able to phosphorylate dUMP, dCMP, CMP, UMP and monophosphates of the pyrimidine nucleoside analogs ddC, dFdC, araC, BVDU and FdUrd with ATP as phosphate donor. Efficacy is highest for dUMP followed by dCMP; CMP and UMP are poor substrates. May be involved in mtDNA depletion caused by long term treatment with ddC or other pyrimidine analogs. The amino acid and/or nucleotide sequence of this determinant would be know to the skilled person or can be derived from suitable database entries, e.g. at Genbank or Uniprot with date of Nov. 11, 2015.

CORO1A: May be a crucial component of the cytoskeleton of highly motile cells, functioning both in the invagination of large pieces of plasma membrane, as well as in forming protrusions of the plasma membrane involved in cell locomotion. In mycobacteria-infected cells, its retention on the phagosomal membrane prevents fusion between phagosomes and lysosomes. The amino acid and/or nucleotide sequence of this determinant would be know to the skilled person or can be derived from suitable database entries, e.g. at Genbank or Uniprot with date of Nov. 11, 2015.

CRP: C-reactive protein. The protein encoded by this gene belongs to the pentaxin family. It is involved in several host defense related functions based on its ability to recognize foreign pathogens and damaged cells of the host and to initiate their elimination by interacting with humoral and cellular effector systems in the blood. The amino acid and/or nucleotide sequence of this determinant would be know to the skilled person or can be derived from suitable database entries, e.g. at Genbank or Uniprot with date of Nov. 11, 2015.

CSDA: Binds to the GM-CSF promoter and seems to act as a repressor. Binds also to full length mRNA and to short RNA sequences containing the consensus site 5'-UC-CAUCA-3'. May have a role in translation repression. The amino acid and/or nucleotide sequence of this determinant would be know to the skilled person or can be derived from suitable database entries, e.g. at Genbank or Uniprot with date of Nov. 11, 2015.

EGFR: The protein encoded by this gene is a transmembrane glycoprotein that is a member of the protein kinase superfamily. This protein is a receptor for members of the epidermal growth factor family. EGFR is a cell surface protein that binds to epidermal growth factor. Binding of the protein to a ligand induces receptor dimerization and tyrosine autophosphorylation and leads to cell proliferation. Mutations in this gene are associated with lung cancer. Multiple alternatively spliced transcript variants that encode different protein isoforms have been found for this gene GPR162: This gene was identified upon genomic analysis of a gene-dense region at human chromosome 12p 13. It appears to be mainly expressed in the brain; however, its function is not known. Alternatively spliced transcript variants encoding different isoforms have been identified. The amino acid and/or nucleotide sequence of this determinant would be know to the skilled person or can be derived from suitable database entries, e.g. at Genbank or Uniprot with date of Nov. 11, 2015.

EIF2AK2: EIF2AK2 is a protein serine/threonine kinase that acquires enzymatic activity following autophosphorylation, a process mediated by double-stranded RNA (dsR A). Additional aliases include without limitation: PKR, PRKR, EIF2AK1, protein kinase, interferon-inducible double stranded RNA dependent, p68 kinase, etc. Activation of EIF2AK2 allows the kinase to phosphorylate its natural substrate, the alpha subunit of eukaryotic protein synthesis initiation factor-2 (EIF2-alpha; MIM 603907), leading to the inhibition of protein synthesis. The amino acid and/or nucleotide sequence of this determinant would be know to the skilled person or can be derived from suitable database entries, e.g. at Genbank or Uniprot with date of Nov. 11, 2015.

EIF4B: Required for the binding of mRNA to ribosomes. Functions in close association with EIF4-F and EIF4-A. It binds near the 5'-terminal cap of mRNA in the presence of EIF-4F and ATP. It promotes the ATPase activity and the ATP-dependent RNA unwinding activity of both EIF4-A and EIF4-F. The amino acid and/or nucleotide sequence of this determinant would be know to the skilled person or can be derived from suitable database entries, e.g. at Genbank or Uniprot with date of Nov. 11, 2015.

Eotaxin: This gene is one of several Cys-Cys (CC) cytokine genes clustered on the q-arm of chromosome 17. Cytokines are a family of secreted proteins involved in immunoregulatory and inflammatory processes. The CC cytokines are proteins characterized by two adjacent cysteines. The cytokine encoded by this gene displays chemotactic activity for eosinophils, but not mononuclear cells or neutrophils. This eosinophil specific chemokine assumed to be involved in eosinophilic inflammatory diseases such as atopic dermatitis, allergic rhinitis, asthma and parasitic infections. In response to the presence of allergens, this protein directly promotes the accumulation of eosinophils, a prominent feature of allergic inflammatory reactions. The amino acid and/or nucleotide sequence of this determinant would be know to the skilled person or can be derived from suitable database entries, e.g. at Genbank or Uniprot with date of Nov. 11, 2015.

EPSTI1: Function was not fully characterized yet. The amino acid and/or nucleotide sequence of this determinant would be know to the skilled person or can be derived from suitable database entries, e.g. at Genbank or Uniprot with date of Nov. 11, 2015.

GAS7: Growth arrest-specific 7 is expressed primarily in terminally differentiated brain cells and predominantly in mature cerebellar Purkinje neurons. GAS7 plays a putative role in neuronal development. Several transcript variants encoding proteins which vary in the N-terminus have been described. It might play a role in promoting maturation and morphological differentiation of cerebellar neurons. The amino acid and/or nucleotide sequence of this determinant would be know to the skilled person or can be derived from suitable database entries, e.g. at Genbank or Uniprot with date of Nov. 11, 2015.

HERC5: Major E3 ligase for ISG15 conjugation. Acts as a positive regulator of innate antiviral response in cells induced by interferon. Makes part of the ISGylation machinery that recognizes target proteins in a broad and relatively non-specific manner. Catalyzes ISGylation of IRF3 which results in sustained activation. It attenuates IRF3-PIN1 interaction, which antagonizes IRF3 ubiquitination and degradation, and boosts the antiviral response. Catalyzes ISGylation of influenza A viral NS1 which attenuates virulence; ISGylated NS1 fails to form homodimers and thus to interact with its RNA targets. It catalyzes ISGylation of papillomavirus type 16 LI protein which results in dominant-negative effect on virus infectivity. Physically associated with polyribosomes, broadly modifies newly synthesized proteins in a co-translational manner. In an interferon-stimulated cell, newly translated viral proteins are primary targets of ISG15. The amino acid and/or nucleotide sequence of this determinant would be know to the skilled person or can be derived from suitable database entries, e.g. at Genbank or Uniprot with date of Nov. 11, 2015.

HLA-A: HLA-A belongs to the HLA class I heavy chain paralogues. This class I molecule is a heterodimer consisting of a heavy chain and a light chain (beta-2 microglobulin). The heavy chain is anchored in the membrane. Class I molecules play a central role in the immune system by presenting peptides derived from the endoplasmic reticulum lumen. They are expressed in nearly all cells. The heavy chain is approximately 45 kDa and its gene contains 8 exons. Exon 1 encodes the leader peptide, exons 2 and 3 encode the alpha1 and alpha2 domains, which both bind the peptide, exon 4 encodes the alpha3 domain, exon 5 encodes the transmembrane region, and exons 6 and 7 encode the cytoplasmic tail. Polymorphisms within exon 2 and exon 3 are responsible for the peptide binding specificity of each class one molecule. Typing for these polymorphisms is routinely done for bone marrow and kidney transplantation. Hundreds of HLA-A alleles have been described. The amino acid and/or nucleotide sequence of this determinant would be know to the skilled person or can be derived from suitable database entries, e.g. at Genbank or Uniprot with date of Nov. 11, 2015.

HLA-B: HLA-B belongs to the HLA class I heavy chain paralogues. This class I molecule is a heterodimer consisting of a heavy chain and a light chain (beta-2 microglobulin). The heavy chain is anchored in the membrane. Class I molecules play a central role in the immune system by presenting peptides derived from the endoplasmic reticulum lumen. They are expressed in nearly all cells. The heavy chain is approximately 45 kDa and its gene contains 8 exons. Exon 1 encodes the leader peptide, exon 2 and 3 encode the alpha1 and alpha2 domains, which both bind the peptide, exon 4 encodes the alpha3 domain, exon 5 encodes the transmembrane region and exons 6 and 7 encode the cytoplasmic tail. Polymorphisms within exon 2 and exon 3 are responsible for the peptide binding specificity of each class one molecule. Typing for these polymorphisms is routinely done for bone marrow and kidney transplantation. Hundreds of HLA-B alleles have been described. The amino acid and/or nucleotide sequence of this determinant would be know to the skilled person or can be derived from suitable database entries, e.g. at Genbank or Uniprot with date of Nov. 11, 2015.

HLA-C: HLA-C belongs to the HLA class I heavy chain paralogues. This class I molecule is a heterodimer consisting of a heavy chain and a light chain (beta-2 microglobulin). The heavy chain is anchored in the membrane. Class I molecules play a central role in the immune system by presenting peptides derived from endoplasmic reticulum lumen. They are expressed in nearly all cells. The heavy chain is approximately 45 kDa and its gene contains 8 exons. Exon one encodes the leader peptide, exons 2 and 3 encode the alpha1 and alpha2 domain, which both bind the peptide, exon 4 encodes the alpha3 domain, exon 5 encodes the transmembrane region, and exons 6 and 7 encode the cytoplasmic tail. Polymorphisms within exon 2 and exon 3 are responsible for the peptide binding specificity of each class one molecule. Typing for these polymorphisms is routinely done for bone marrow and kidney transplantation. Over one hundred HLA-C alleles have been described. The amino acid and/or nucleotide sequence of this determinant would be know to the skilled person or can be derived from suitable database entries, e.g. at Genbank or Uniprot with date of Nov. 11, 2015.

IFI6: This gene was first identified as one of the many genes induced by interferon. The encoded protein may play a critical role in the regulation of apoptosis. A mini satellite that consists of 26 repeats of a 12 nucleotide repeating element resembling the mammalian splice donor consensus sequence begins near the end of the second exon. Alternatively spliced transcript variants that encode different isoforms by using the two downstream repeat units as splice donor sites have been described. The amino acid and/or nucleotide sequence of this determinant would be know to the skilled person or can be derived from suitable database entries, e.g. at Genbank or Uniprot with date of Nov. 11, 2015.

IFIT1: Interferon-induced protein with tetratricopeptide repeats. The amino acid and/or nucleotide sequence of this determinant would be know to the skilled person or can be derived from suitable database entries, e.g. at Genbank or Uniprot with date of Nov. 11, 2015.

IFIT3: Function was not fully characterized yet. The amino acid and/or nucleotide sequence of this determinant would be know to the skilled person or can be derived from suitable database entries, e.g. at Genbank or Uniprot with date of Nov. 11, 2015.

IFITM1: IFN-induced antiviral protein that mediate cellular innate immunity to at least three major human pathogens, namely influenza A H1N1 virus, West Nile virus, and dengue virus by inhibiting the early step(s) of replication. Plays a key role in the antiproliferative action of IFN-gamma either by inhibiting the ERK activation or by arresting cell growth in G1 phase in a p53-dependent manner. Implicated in the control of cell growth. Component of a multimeric complex involved in the transduction of antiproliferative and homotypic adhesion signals. The amino acid and/or nucleotide sequence of this determinant would be know to the skilled person or can be derived from suitable database entries, e.g. at Genbank or Uniprot with date of Nov. 11, 2015.

IFITM3 IFITM2: IFN-induced antiviral protein that mediates cellular innate immunity to at least three major human pathogens, namely influenza A H1N1 virus, West Nile virus (WNV), and dengue virus (WNV), by inhibiting the early step(s) of replication. The amino acid and/or nucleotide sequence of this determinant would be know to the skilled person or can be derived from suitable database entries, e.g. at Genbank or Uniprot with date of Nov. 11, 2015.

IL1a: The protein encoded by this gene is a member of the interleukin 1 cytokine family. This cytokine is a pleiotropic cytokine involved in various immune responses, inflammatory processes, and hematopoiesis. This cytokine can be produced by monocytes and macrophages as a proprotein, which is proteolytically processed and released in response to cell injury, and thus induces apoptosis. This gene and eight other interleukin 1 family genes form a cytokine gene cluster on chromosome 2. IL-1 proteins are involved in the inflammatory response, being identified as endogenous pyrogens, and are reported to stimulate the release of prostaglandin and collagenase from synovial cells. The amino acid and/or nucleotide sequence of this determinant would be know to the skilled person or can be derived from suitable database entries, e.g. at Genbank or Uniprot with date of Nov. 11, 2015.

IL1RA: The protein encoded by this gene is a cytokine receptor that belongs to the interleukin 1 receptor family. This protein is a receptor for interleukin alpha (ILIA), interleukin beta (IL1B), and interleukin 1 receptor, type I (ILIRI/ILIRA). It is an important mediator involved in many cytokine induced immune and inflammatory responses. Additional names of the gene include without limitations: CD121A, IL-1RT1, p80, CD121a antigen, CD121A, IL1R and IL1ra. The amino acid and/or nucleotide sequence of this determinant would be know to the skilled person or can be derived from suitable database entries, e.g. at Genbank or Uniprot with date of Nov. 11, 2015.

IL6: This gene encodes a cytokine that functions in inflammation and the maturation of B cells. In addition, the encoded protein has been shown to be an endogenous pyrogen capable of inducing fever in people with autoimmune diseases or infections. The protein is primarily produced at sites of acute and chronic inflammation, where it is secreted into the serum and induces a transcriptional inflammatory response through interleukin 6 receptor, alpha. The functioning of this gene is implicated in a wide variety of inflammation-associated disease states, including susceptibility to diabetes mellitus and systemic juvenile rheumatoid arthritis. The amino acid and/or nucleotide sequence of this determinant would be know to the skilled person or can be derived from suitable database entries, e.g. at Genbank or Uniprot with date of Nov. 11, 2015.

IL7R: The protein encoded by this gene is a receptor for interleukine 7 (IL7). The function of this receptor requires the interleukin 2 receptor, gamma chain (IL2RG), which is a common gamma chain shared by the receptors of various cytokines, including interleukin 2, 4, 7, 9, and 15. This protein has been shown to play a critical role in the V(D)J recombination during lymphocyte development. This protein is also found to control the accessibility of the TCR gamma locus by STAT5 and histone acetylation. Knockout studies in mice suggested that blocking apoptosis is an essential function of this protein during differentiation and activation of T lymphocytes. The functional defects in this protein may be associated with the pathogenesis of the severe combined immunodeficiency (SCID). The amino acid and/or nucleotide sequence of this determinant would be know to the skilled person or can be derived from suitable database entries, e.g. at Genbank or Uniprot with date of Nov. 11, 2015.

IL-8: The protein encoded by this gene is a member of the CXC chemokine family. Additional aliases of IL-8 include without limitation: Interleukin 8, K60, CXCL8, SCYB8, GCP-1, TSG-1, MDNCF, b-ENAP, MONAP, alveolar macrophage chemotactic factor I, NAP-1, beta endothelial cell-derived neutrophil activating peptide, GCP1, beta-thromboglobulin-like protein, LECT, chemokine (C-X-C motif) ligand 8, LUCT, emoctakin, LYNAP, interleukin-8, NAF, lung giant cell carcinoma-derived chemotactic protein, NAP1, lymphocyte derived neutrophil activating peptide, IL-8, neutrophil-activating peptide 1, Granulocyte chemotactic protein 1, small inducible cytokine subfamily B, member 8, Monocyte-derived neutrophil chemotactic factor, tumor necrosis factor-induced gene 1, Monocyte-derived neutrophil-activating peptide, Emoctakin, T-cell chemotactic factor,C-X-C motif chemokine 8, 3-10C,Neutrophil-activating protein 1, AMCF-I and Protein 3-1OC. This chemokine is one of the major mediators of the inflammatory response. This chemokine is secreted by several cell types. It functions as a chemoattractant, and is also a potent angiogenic factor. This gene is believed to play a role in the pathogenesis of bronchiolitis, a common respiratory tract disease caused by viral infection. This gene and other ten members of the CXC chemokine gene family form a chemokine gene cluster in a region mapped to chromosome 4q. IL-8 is a chemotactic factor that attracts neutrophils, basophils, and T-cells, but not monocytes. It is also involved in neutrophil activation. IL-8(6-77) has a 5-10-fold higher activity on neutrophil activation, IL-8(5-77) has increased activity on neutrophil activation and IL-8(7-77) has a higher affinity to receptors CXCR1 and CXCR2 as compared to IL-8(l-77), respectively. The amino acid and/or nucleotide sequence of this determinant would be know to the skilled person or can be derived from suitable database entries, e.g. at Genbank or Uniprot with date of Nov. 11, 2015.

IP10: This gene encodes a chemokine of the CXC subfamily and ligand for the receptor CXCR3. Binding of this protein to CXCR3 results in pleiotropic effects, including stimulation of monocytes, natural killer and T-cell migration, and modulation of adhesion molecule expression. Additional names of the gene include without limitations: CXCL10, Gamma-IP 10, INP10 and chemokine (C-X-C motif) ligand 10. The amino acid and/or nucleotide sequence of this determinant would be know to the skilled person or can be derived from suitable database entries, e.g. at Genbank or Uniprot with date of Nov. 11, 2015.

ISG15: ISG15 ubiquitin-like modifier; additional aliases of ISG15 include without limitation G1P2, IFI15, IP17, UCRP and hUCRP. This ubiquitin-like protein is conjugated to intracellular target proteins after IFN-alpha or IFN-beta stimulation. Its enzymatic pathway is partially distinct from that of ubiquitin, differing in substrate specificity and interaction with ligating enzymes. ISG15 conjugation pathway uses a dedicated E1 enzyme, but seems to converge with the Ub conjugation pathway at the level of a specific E2 enzyme. Targets include STAT1, SERPINA3G/SPI2A, JAK1, MAPK3/ERK1, PLCG1, EIF2AK2/PKR, MX1/MxA, and RIG-1. Shows specific chemotactic activity towards neutrophils and activates them to induce release of eosinophil chemotactic factors. May serve as a trans-acting binding factor directing the association of ligated target proteins to intermediate filaments. May also be involved in autocrine, paracrine and endocrine mechanisms, as in cell-to-cell signaling, possibly partly by inducing IFN-gamma secretion by monocytes and macrophages. The amino acid and/or nucleotide sequence of this determinant would be know to the skilled person or can be derived from suitable database entries, e.g. at Genbank or Uniprot with date of Nov. 11, 2015.

ITGAM: This gene encodes the integrin alpha M chain. Integrins are heterodimeric integral membrane proteins composed of an alpha chain and a beta chain. This I-domain containing alpha integrin combines with the beta 2 chain (ITGB2) to form a leukocyte-specific integrin referred to as macrophage receptor 1 ('Mac-1'), or inactivated-C3b (iC3b) receptor 3 ('CR3'). The alpha M beta 2 integrin is important in the adherence of neutrophils and monocytes to stimulated endothelium, and also in the phagocytosis of complement coated particles. Multiple transcript variants encoding different isoforms have been found for this gene.

Mac-2-BP: Additional aliases of MAC-2-BP include without limitation LGALS3BP, 90K, serum protein 90K, BTBD17B, M2BP and lectin, galactoside-binding, soluble, 3 binding protein. The galectins are a family of beta-galactoside-binding proteins implicated in modulating cell-cell and cell-matrix interactions. The levels of MAC-2-BP were found to be elevated in the serum of cancer patients. It appears to be implicated in immune response associated with natural killer (NK) and lymphokine-activated killer (LAK) cell cytotoxicity. The native protein can bind specifically to a human macrophage-associated lectin known as Mac-2 as well as galectin 1. The amino acid and/or nucleotide sequence of this determinant would be know to the skilled person or can be derived from suitable database entries, e.g. at Genbank or Uniprot with date of Nov. 11, 2015.

MCP: The protein encoded by this gene is a type I membrane protein and is a regulatory part of the complement system. The encoded protein has cofactor activity for inactivation of complement components C3b and C4b by serum factor I, which protects the host cell from damage by complement. In addition, the encoded protein can act as a receptor for the Edmonston strain of measles virus, human herpesvirus-6, and type IV pili of pathogenic Neisseria. The protein encoded by this gene may be involved in the fusion of the spermatozoa with the oocyte during fertilization. Mutations at this locus have been associated with susceptibility to hemolytic uremic syndrome. Alternatively spliced transcript variants encoding different isoforms have been described. The amino acid and/or nucleotide sequence of this determinant would be know to the skilled person or can be derived from suitable database entries, e.g. at Genbank or Uniprot with date of Nov. 11, 2015.

ISG20: Exonuclease with specificity for single-stranded RNA and, to a lesser extent for DNA. Degrades RNA at a rate that is approximately 35-fold higher than its rate for single-stranded DNA. Involved in the antiviral function of IFN against RNA viruses.

KIAA0082 (FTSJD2): S-adenosyl-L-methionine-dependent methyltransferase that mediates mRNA cap1 2'-O-ribose methylation to the 5'-cap structure of mRNAs. Methylates the ribose of the first nucleotide of a m(7)GpppG-capped mRNA to produce m(7)GpppNmp (cap1). Cap1 modification is linked to higher levels of translation. May be involved in the interferon response pathway. The amino acid and/or nucleotide sequence of this determinant would be know to the skilled person or can be derived from suitable database entries, e.g. at Genbank or Uniprot with date of Nov. 11, 2015.

LIPT1: The process of transferring lipoic acid to proteins is a two-step process. The first step is the activation of lipoic acid by lipoate-activating enzyme to form lipoyl-AMP. For the second step, the protein encoded by this gene transfers the lipoyl moiety to apoproteins. Alternative splicing in the 5' UTR of this gene results in five transcript variants that encode the same protein. The amino acid and/or nucleotide sequence of this determinant would be know to the skilled person or can be derived from suitable database entries, e.g. at Genbank or Uniprot with date of Nov. 11, 2015.

LOC26010(SPATS2): Function was not fully characterized yet. The amino acid and/or nucleotide sequence of this determinant would be know to the skilled person or can be derived from suitable database entries, e.g. at Genbank or Uniprot with date of Nov. 11, 2015.

LRDD: The protein encoded by this gene contains a leucine-rich repeat and a death domain. This protein has been shown to interact with other death domain proteins, such as Fas (TNFRSF6)-associated via death domain (FADD) and MAP-kinase activating death domain-containing protein (MADD), and thus may function as an adaptor protein in cell death-related signaling processes. The expression of the mouse counterpart of this gene has been found to be positively regulated by the tumor suppressor p53 and to induce cell apoptosis in response to DNA damage, which suggests a role for this gene as an effector of p53-dependent apoptosis. Alternative splicing results in multiple transcript variants. The amino acid and/or nucleotide sequence of this determinant would be know to the skilled person or can be derived from suitable database entries, e.g. at Genbank or Uniprot with date of Nov. 11, 2015.

LTA4H: Hydrolyzes an epoxide moiety of leukotriene A4 (LTA-4) to form leukotriene B4 (LTB-4). The enzyme also has some peptidase activity. The amino acid and/or nucleotide sequence of this determinant would be know to the skilled person or can be derived from suitable database entries, e.g. at Genbank or Uniprot with date of Nov. 11, 2015.

LY6E: Function was not fully characterized yet. The amino acid and/or nucleotide sequence of this determinant would be know to the skilled person or can be derived from suitable database entries, e.g. at Genbank or Uniprot with date of Nov. 11, 2015.

MAN1C1: Mannosidases are divided into two subtypes; I and II, (EC numbers 3.2.1.113 and 3.2.1.114 respectively) which display a wide expression pattern. Mannosidase I hydrolyzes (1,2)-linked alpha-D-mannose residues in the oligo-mannose oligosaccharide Man9(GlcNAc)2 and mannosidase II hydrolyzes (1,3)- and (1,6)-linked alpha-D-mannose residues in Man5(GlcNAc)3. Both subtypes require a divalent cation cofactor. Mutations in mannosidases can cause mannosidosis (mannosidase I deficiency). The amino acid and/or nucleotide sequence of this determinant would be know to the skilled person or can be derived from suitable database entries, e.g. at Genbank or Uniprot with date of Nov. 11, 2015.

MBOAT2: Acyltransferase which mediates the conversion of lysophosphatidyl-ethanolamine (1-acyl-sn-glycero-3-phosphoethanolamine or LPE) into phosphatidyl-ethanolamine (1,2-diacyl-sn-glycero-3-phosphoethanolamine or PE) (LPEAT activity). Catalyzes also the acylation of lysophosphatidic acid (LPA) into phosphatidic acid (PA) (LPAAT activity). Has also a very weak lysophosphatidyl-choline acyltransferase (LPCAT activity). Prefers oleoyl-CoA as the acyl donor. Lysophospholipid acyltransferases (LPLATs) catalyze the reacylation step of the phospholipid remodeling pathway also known as the Lands cycle. The amino acid and/or nucleotide sequence of this determinant would be know to the skilled person or can be derived from suitable database entries, e.g. at Genbank or Uniprot with date of Nov. 11, 2015.

MX1/MXA: In mouse, the interferon-inducible Mx protein is responsible for a specific antiviral state against influenza virus infection. The protein encoded by this gene is similar to the mouse protein as determined by its antigenic relatedness, induction conditions, physicochemical properties, and amino acid analysis. This cytoplasmic protein is a member of both the dynamin family and the family of large GTPases. Two transcript variants encoding the same protein have been found for this gene. The amino acid and/or nucleotide sequence of this determinant would be know to the skilled person or can be derived from suitable database entries, e.g. at Genbank or Uniprot with date of Nov. 11, 2015.

NPM1: It is involved in diverse cellular processes such as ribosome biogenesis, centrosome duplication, protein chaperoning, histone assembly, cell proliferation, and regulation of tumor suppressors TP53/p53 and ARF. It binds ribosome presumably to drive ribosome nuclear export. It is associated with nucleolar ribonucleoprotein structures and binds single stranded nucleic acids. Acts as a chaperonin for the core histones H3, H2B and H4. The amino acid and/or nucleotide sequence of this determinant would be know to the skilled person or can be derived from suitable database entries, e.g. at Genbank or Uniprot with date of Nov. 11, 2015.

NRG1: The protein encoded by this gene was originally identified as a 44-kD glycoprotein that interacts with the NEU/ERBB2 receptor tyrosine kinase to increase its phosphorylation on tyrosine residues. This protein is a signaling protein that mediates cell-cell interactions and plays critical roles in the growth and development of multiple organ systems. It is known that an extraordinary variety of different isoforms are produced from this gene through alternative promoter usage and splicing. These isoforms are tissue-specifically expressed and differ significantly in their structure, and thereby these isoforms are classified into types I, II, III, IV, V and VI. The gene dysregulation has been linked to diseases such as cancer, schizophrenia and bipolar disorder (BPD). The amino acid and/or nucleotide sequence of this determinant would be know to the skilled person or can be derived from suitable database entries, e.g. at Genbank or Uniprot with date of Nov. 11, 2015.

OAS2: This gene encodes a member of the 2-5 A synthetase family, essential proteins involved in the innate immune response to viral infection. The encoded protein is induced by interferons and uses adenosine triphosphate in 2'-specific nucleotidyl transfer reactions to synthesize 2',5'-oligoadenylates (2-5 As). These molecules activate latent RNase L, which results in viral RNA degradation and the inhibition of viral replication. The three known members of this gene family are located in a cluster on chromosome 12. Alternatively spliced transcript variants encoding different isoforms have been described. The amino acid and/or nucleotide sequence of this determinant would be know to the skilled person or can be derived from suitable database entries, e.g. at Genbank or Uniprot with date of Nov. 11, 2015.

PARP9: Poly (ADP-ribose) polymerase (PARP) catalyzes the post-translational modification of proteins by the addition of multiple ADP-ribose moieties. PARP transfers ADP-ribose from nicotinamide dinucleotide (NAD) to glu/asp residues on the substrate protein, and also polymerizes ADP-ribose to form long/branched chain polymers. PARP inhibitors are being developed for use in a number of pathologies including cancer, diabetes, stroke and cardiovascular diseases. The amino acid and/or nucleotide sequence of this determinant would be know to the skilled person or can be derived from suitable database entries, e.g. at Genbank or Uniprot with date of Nov. 11, 2015.

PARP 12: Poly (ADP-ribose) polymerase (PARP) catalyzes the post-translational modification of proteins by the addition of multiple ADP-ribose moieties. PARP transfers ADP-ribose from nicotinamide dinucleotide (NAD) to glu/asp residues on the substrate protein, and also polymerizes ADP-ribose to form long/branched chain polymers. PARP inhibitors are being developed for use in a number of pathologies including cancer, diabetes, stroke and cardiovascular diseases. The amino acid and/or nucleotide sequence of this determinant would be know to the skilled person or can be derived from suitable database entries, e.g. at Genbank or Uniprot with date of Nov. 11, 2015.

PCT: Procalcitonin (PCT) is a peptide precursor of the hormone calcitonin, the latter being involved with calcium homeostasis. The levels of procalcitonin rise in a response to a proinflammatory stimulus. The amino acid and/or nucleotide sequence of this determinant would be know to the skilled person or can be derived from suitable database entries, e.g. at Genbank or Uniprot with date of Nov. 11, 2015.

PDIA6: Protein disulfide isomerases (EC 5.3.4.1), such as PDIA6, are endoplasmic reticulum (ER) resident proteins that catalyze formation, reduction, and isomerization of disulfide bonds in proteins and are thought to play a role in folding of disulfide-bonded proteins. It might function as a chaperone that inhibits aggregation of mis-folded proteins. Plays a role in platelet aggregation and activation by agonists such as convulxin, collagen and thrombin. The amino acid and/or nucleotide sequence of this determinant would be know to the skilled person or can be derived from suitable database entries, e.g. at Genbank or Uniprot with date of Nov. 11, 2015.

Procalcitonin: Is a peptide precursor of the hormone calcitonin, which is involved with calcium homeostasis. The level of procalcitonin rises in a response to a proinflammatory stimulus, especially of bacterial origin. In this case, it is produced mainly by the cells of the lung and the intestine. It does not rise significantly with viral or non-infectious inflammations. The amino acid and/or nucleotide sequence of this determinant would be know to the skilled person or can be derived from suitable database entries, e.g. at Genbank or Uniprot with date of Nov. 11, 2015

PTEN: Tumor suppressor. Acts as a dual-specificity protein phosphatase, ephosphorylating tyrosine-, serine- and threonine-phosphorylated proteins. Also acts as a lipid phosphatase, removing the phosphate in the D3 position of the inositol ring from phosphatidylinositol (PI) 3,4,5-trisphosphate, PI 3,4-diphosphate, PI 3-phosphate and inositol 1,3, 4,5-tetrakisphosphate with order of substrate preference in vitro PtdIns(3,4,5)P3>PtdIns(3,4)P2>PtdIns3P>Ins(1,3,4,5) P4. The lipid phosphatase activity is critical for its tumor suppressor function. Antagonizes the PI3K-AKT/PKB signaling pathway by dephosphorylating phosphoinositides and thereby modulating cell cycle progression and cell survival. The un-phosphorylated form cooperates with AIP1 to suppress AKT1 activation. Dephosphorylates tyrosine-phosphorylated focal adhesion kinase and inhibits cell migration and integrin-mediated cell spreading and focal adhesion formation. Plays a role as a key modulator of the AKT-mTOR signaling pathway controlling the tempo of the process of newborn neurons integration during adult neurogenesis, including correct neuron positioning, dendritic development and synapse formation. May be a negative regulator of insulin signaling and glucose metabolism in adipose tissue. The nuclear monoubiquitinated form possesses greater apoptotic potential, whereas the cytoplasmic nonubiquitinated form induces less tumor suppressive ability. The amino acid and/or nucleotide sequence of this determinant would be know to the skilled person or can be derived from suitable database entries, e.g. at Genbank or Uniprot with date of Nov. 11, 2015.

RAB13: could participate in polarized transport, in the assembly and/or the activity of tight junctions. The amino acid and/or nucleotide sequence of this determinant would be know to the skilled person or can be derived from suitable database entries, e.g. at Genbank or Uniprot with date of Nov. 11, 2015.

RAP1B: GTP-binding protein that possesses intrinsic GTPase activity. Contributes to the polarizing activity of KRIT1 and CDH5 in the establishment and maintenance of correct endothelial cell polarity and vascular lumen. Required for the localization of phosphorylated PRKCZ, PARD3 and TIAM1 to the cell junction. The amino acid and/or nucleotide sequence of this determinant would be know to the skilled person or can be derived from suitable database entries, e.g. at Genbank or Uniprot with date of Nov. 11, 2015.

RTN3: May be involved in membrane trafficking in the early secretory pathway. Inhibits BACE1 activity and amyloid precursor protein processing. May induce caspase-8 cascade and apoptosis. May favor BCL2 translocation to the mitochondria upon endoplasmic reticulum stress. In case of enteroviruses infection, RTN3 may be involved in the viral replication or pathogenesis. The amino acid and/or nucleotide sequence of this determinant would be know to the skilled person or can be derived from suitable database entries, e.g. at Genbank or Uniprot with date of Nov. 11, 2015.

SAA: encodes a member of the serum amyloid A family of apo lipoproteins. The encoded protein is a major acute phase protein that is highly expressed in response to inflammation and tissue injury. This protein also plays an important role in HDL metabolism and cholesterol homeostasis. High levels of this protein are associated with chronic inflammatory diseases including atherosclerosis, rheumatoid arthritis, Alzheimer's disease and Crohn s disease. This protein may also be a potential biomarker for certain tumors. Alternate splicing results in multiple transcript variants that encode the same protein. The amino acid and/or nucleotide sequence of this determinant would be know to the skilled person or can be derived from suitable database entries, e.g. at Genbank or Uniprot with date of Nov. 11, 2015.

QARS: Aminoacyl-tRNA synthetases catalyze the aminoacylation of tRNA by their cognate amino acid. Because of their central role in linking amino acids with nucleotide triplets contained in tRNAs, aminoacyl-tRNA synthetases are thought to be among the first proteins that appeared in evolution. In metazoans, 9 aminoacyl-tRNA synthetases specific for glutamine (gin), glutamic acid (glu), and 7 other amino acids are associated within a multienzyme complex. Although present in eukaryotes, glutaminyl-tRNA synthetase (QARS) is absent from many prokaryotes, mitochondria, and chloroplasts, in which Gln-tRNA(Gln) is formed by transamidation of the misacylated Glu-tRNA(Gln). Glutaminyl-tRNA synthetase belongs to the class-I aminoacyl-tRNA synthetase family. The amino acid and/or nucleotide sequence of this determinant would be know to the skilled person or can be derived from suitable database entries, e.g. at Genbank or Uniprot with date of Nov. 11, 2015.

RAB13: could participate in polarized transport, in the assembly and/or the activity of tight junctions. The amino acid and/or nucleotide sequence of this determinant would be know to the skilled person or can be derived from suitable database entries, e.g. at Genbank or Uniprot with date of Nov. 11, 2015.

RAB31: Small GTP-binding proteins of the RAB family, such as RAB31, play essential roles in vesicle and granule targeting. The amino acid and/or nucleotide sequence of this determinant would be know to the skilled person or can be derived from suitable database entries, e.g. at Genbank or Uniprot with date of Nov. 11, 2015.

RAC2: Small G proteins (small GTPases) are homologous to Galpha proteins and are often referred to as the Ras proto-oncogene superfamily. The Ras superfamily contains over 100 small GTPases grouped into eight families; Ras, Rho, Rab, Rap, Arf, Ran, Rheb and Rad. Small GTPases regulate a wide variety of processes in the cell, including growth, differentiation, movement and lipid vesicle transport. Like Galpha proteins, small GTPases alternate between an On' state (bound to GTP) and an Off state (bound to GDP). This cyclic process requires guanine nucleotide exchange factor (GEF) and GTPase-activating protein (GAP). Small GTPases are the downstream effectors of most receptor tyrosine kinases (RTKs) and are linked via two proteins, GRB2 and SOS. They are coupled to intracellular signaling cascades including the MAPK pathway, through interactions with Raf kinase. Normally, activation of small GTPases is induced by ligand binding to a RTK. In many transformed cells activating mutations of GTPases, often Ras, produce a cellular response in the absence of a ligand, thus promoting malignant progression. The amino acid and/or nucleotide sequence of this determinant would be know to the skilled person or can be derived from suitable database entries, e.g. at Genbank or Uniprot with date of Nov. 11, 2015.

RPL34: Ribosomes, the organelles that catalyze protein synthesis, consist of a small 40S subunit and a large 60S subunit. Together these subunits are composed of 4 RNA species and approximately 80 structurally distinct proteins. This gene encodes a ribosomal protein that is a component of the 60S subunit. The protein belongs to the L34E family of ribosomal proteins. It is located in the cytoplasm. This gene originally was thought to be located at 17q21, but it has been mapped to 4q. Transcript variants derived from alternative splicing, alternative transcription initiation sites, and/or alternative polyadenylation exist; these variants encode the same protein. As is typical for genes encoding ribosomal proteins, there are multiple processed pseudogenes of this gene dispersed through the genome. The amino acid and/or nucleotide sequence of this determinant would be know to the skilled person or can be derived from suitable database entries, e.g. at Genbank or Uniprot with date of Nov. 11, 2015.

RSAD2: Involved in antiviral defense. May impair virus budding by disrupting lipid rafts at the plasma membrane, a feature which is essential for the budding process of many viruses. Acts through binding with and inactivating FPPS, an enzyme involved in synthesis of cholesterol, farnesylated and geranylated proteins, ubiquinone dolichol and heme. Plays a role in the cell antiviral state induced by type I and type II interferon. Displays antiviral effect against HIV-1 virus, hepatitis C virus, human cytomegalovirus, and aphaviruses, but not vesiculovirus. The amino acid and/or nucleotide sequence of this determinant would be know to the skilled person or can be derived from suitable database entries, e.g. at Genbank or Uniprot with date of Nov. 11, 2015.

SART3: The protein encoded by this gene is an RNA-binding nuclear protein that is a tumor-rejection antigen. This antigen possesses tumor epitopes capable of inducing HLA-A24-restricted and tumor-specific cytotoxic T lymphocytes in cancer patients and may be useful for specific immunotherapy. This gene product is found to be an important cellular factor for HIV-1 gene expression and viral replication. It also associates transiently with U6 and U4/U6 snRNPs during the recycling phase of the spliceosome cycle. This encoded protein is thought to be involved in the regulation of mRNA splicing. The amino acid and/or nucleotide sequence of this determinant would be know to the skilled person or can be derived from suitable database entries, e.g. at Genbank or Uniprot with date of Nov. 11, 2015.

SDCBP: The protein encoded by this gene was initially identified as a molecule linking syndecan-mediated signaling to the cytoskeleton. The syntenin protein contains tandemly repeated PDZ domains that bind the cytoplasmic, C-terminal domains of a variety of transmembrane proteins. This protein may also affect cytoskeletal-membrane organization, cell adhesion, protein trafficking, and the activation of transcription factors. The protein is primarily localized to membrane-associated adherens junctions and focal adhesions but is also found at the endoplasmic reticulum and nucleus. Alternative splicing results in multiple transcript variants encoding different isoforms. It seems to couple transcription factor SOX4 to the IL-5 receptor (IL5RA). May play a role in vesicular trafficking and seems to be required for the targeting of TGFA to the cell surface in the early secretory pathway. The amino acid and/or nucleotide sequence of this determinant would be know to the skilled person or can be derived from suitable database entries, e.g. at Genbank or Uniprot with date of Nov. 11, 2015.

SELI: This gene encodes a selenoprotein, which contains a selenocysteine (Sec) residue at its active site. The selenocysteine is encoded by the UGA codon that normally signals translation termination. The 3' UTR of selenoprotein genes have a common stem-loop structure, the sec insertion sequence (SECIS), that is necessary for the recognition of UGA as a Sec codon rather than as a stop signal. The amino acid and/or nucleotide sequence of this determinant would be know to the skilled person or can be derived from suitable database entries, e.g. at Genbank or Uniprot with date of Nov. 11, 2015.

SPINT2: This gene encodes a transmembrane protein with two extracellular Kunitz domains that inhibits a variety of serine proteases. The protein inhibits HGF activator which prevents the formation of active hepatocyte growth factor. This gene is a putative tumor suppressor, and mutations in this gene result in congenital sodium diarrhea. Multiple transcript variants encoding different isoforms have been found for this gene. The amino acid and/or nucleotide sequence of this determinant would be know to the skilled person or can be derived from suitable database entries, e.g. at Genbank or Uniprot with date of Nov. 11, 2015.

SMAD9: The protein encoded by this gene is a member of the SMAD family, which transduces signals from TGF-beta family members. The encoded protein is activated by bone morphogenetic proteins and interacts with SMAD4. Two transcript variants encoding different isoforms have been found for this gene. Transcriptional modulator activated by BMP (bone morphogenetic proteins) type 1 receptor kinase. SMAD9 is a receptor-regulated SMAD (R-SMAD). The amino acid and/or nucleotide sequence of this determinant would be know to the skilled person or can be derived from suitable database entries, e.g. at Genbank or Uniprot with date of Nov. 11, 2015.

SOCS3: SOCS family proteins form part of a classical negative feedback system that regulates cytokine signal transduction. SOCS3 is involved in negative regulation of cytokines that signal through the JAK/STAT pathway. Inhibits cytokine signal transduction by binding to tyrosine kinase receptors including gp130, LIF, erythropoietin, insulin, IL12, GCSF and leptin receptors. Binding to JAK2 inhibits its kinase activity. Suppresses fetal liver erythropoiesis. Regulates onset and maintenance of allergic responses mediated by T-helper type 2 cells. Regulates IL-6 signaling in vivo (By similarity). Probable substrate recognition component of a SCF-like ECS (Elongin BC-CUL2/5-SOCS-box protein) E3 ubiquitin-protein ligase complex which mediates the ubiquitination and subsequent proteasomal degradation of target proteins. Seems to recognize IL6ST (By similarity). The amino acid and/or nucleotide sequence of this determinant would be know to the skilled person or can be derived from suitable database entries, e.g. at Genbank or Uniprot with date of Nov. 11, 2015.

TRAIL: The protein encoded by this gene is a cytokine that belongs to the tumor necrosis factor (TNF) ligand family. Additional names of the gene include without limitations AP02L, TNF-related apoptosis-inducing ligand, TNFSF10 and CD253. TRAIL exists in a membrane bound form and a soluble form, both of which can induce apoptosis in different cells, such as transformed tumor cells. This protein binds to several members of the TNF receptor superfamily such as TNFRSF1 OA/TRAILR1, NFRSF1 0B/TRAILR2, NFRSF10C/TRAILR3, TNFRSF 10D/TRAILR4, and possibly also to NFRSF1 IB/OPG. The activity of this protein may be modulated by binding to the decoy receptors such as NFRSF10C/TRAILR3, TNFRSF 10D/TRAILR4, and NFRSF1 IB/OPG that cannot induce apoptosis. The binding of this protein to its receptors has been shown to trigger the activation of MAPK8/JNK, caspase 8, and caspase 3. Alternatively spliced transcript variants encoding different isoforms have been found for this gene. TRAIL can be proteolytically cleaved from the cell surface to produce a soluble form that has a homotrimeric structure. The amino acid and/or nucleotide sequence of this determinant would be know to the skilled person or can be derived from suitable database entries, e.g. at Genbank or Uniprot with date of Nov. 11, 2015.

TREM1: Triggering receptor expressed on myeloid cells 1; additional aliases of TREM1 are CD354 and TREM-1. This gene encodes a receptor belonging to the Ig superfamily that is expressed on myeloid cells. This protein amplifies neutrophil and monocyte-mediated inflammatory responses triggered by bacterial and fungal infections by stimulating release of pro-inflammatory chemokines and cytokines, as well as increased surface expression of cell activation markers. Alternatively spliced transcript variants encoding different isoforms have been noted for this gene. The protein encoded by this gene has a soluble form which is denoted by sTREM1. The amino acid and/or nucleotide sequence of this determinant would be know to the skilled person or can be derived from suitable database entries, e.g. at Genbank or Uniprot with date of Nov. 11, 2015.

TRIM22: Interferon-induced antiviral protein involved in cell innate immunity. The antiviral activity could in part be mediated by TRIM22-dependent ubiquitination of viral proteins. Plays a role in restricting the replication of HIV-1, encephalomyocarditis virus (EMCV) and hepatitis B virus (HBV). Acts as a transcriptional repressor of HBV core promoter. May have E3 ubiquitin-protein ligase activity. The amino acid and/or nucleotide sequence of this determinant would be know to the skilled person or can be derived from suitable database entries, e.g. at Genbank or Uniprot with date of Nov. 11, 2015.

UBE2N: The UBE2V1-UBE2N and UBE2V2-UBE2N heterodimers catalyze the synthesis of non-canonical 'Lys-63'-linked polyubiquitin chains. This type of polyubiquitination does not lead to protein degradation by the proteasome. It mediates transcriptional activation of target genes. It plays a role in the control of progress through the cell cycle and differentiation. Plays a role in the error-free DNA repair pathway and contributes to the survival of cells after DNA damage. Acts together with the E3 ligases, HLTF and SHPRH, in the 'Lys-63'-linked poly ubiquitination of PCNA upon genotoxic stress, which is required for DNA repair. It appears to act together with E3 ligase RNF5 in the 'Lys-63'-linked polyubiquitination of JKAMP thereby regulating JKAMP function by decreasing its association with components of the proteasome and ERAD. The amino acid and/or nucleotide sequence of this determinant would be know to the skilled person or can be derived from suitable database entries, e.g. at Genbank or Uniprot with date of Nov. 11, 2015.

VEGFR2: Vascular endothelial growth factor (VEGF) is a major growth factor for endothelial cells. This gene encodes one of the two receptors of the VEGF. This receptor, known as kinase insert domain receptor, is a type III receptor tyrosine kinase. It functions as the main mediator of VEGF-induced endothelial proliferation, survival, migration, tubular morphogenesis and sprouting. The signaling and trafficking of this receptor are regulated by multiple factors, including Rab GTPase, P2Y purine nucleotide receptor, integrin alphaVbeta3, T-cell protein tyrosine phosphatase, etc. Mutations of this gene are implicated in infantile capillary hemangiomas (provided by RefSeq). The protein encoded by this gene has a soluble form denoted sVEGFR2. The amino acid and/or nucleotide sequence of this determinant would be know to the skilled person or can be derived from suitable database entries, e.g. at Genbank or Uniprot with date of Nov. 11, 2015.

XAF1: Seems to function as a negative regulator of members of the IAP (inhibitor of apoptosis protein) family. Inhibits anti-caspase activity of BIRC4. Induces cleavage and inactivation of BIRC4 independent of caspase activation. Mediates TNF-alpha-induced apoptosis and is involved in apoptosis in trophoblast cells. May inhibit BIRC4 indirectly by activating the mitochondrial apoptosis pathway. After translocation to mitochondra, promotes translocation of BAX to mitochondria and cytochrome c release from mitochondria. Seems to promote the redistribution of BIRC4 from the cytoplasm to the nucleus, probably independent of BIRC4 inactivation which seems to occur in the cytoplasm. The BIRC4-XAF1 complex mediates down-regulation of BIRC5/survivin; the process requires the E3 ligase activity of BIRC4. Seems to be involved in cellular sensitivity to the proapoptotic actions of TRAIL. May be a tumor suppressor by mediating apoptosis resistance of cancer cells. The amino acid and/or nucleotide sequence of this determinant would be know to the skilled person or can be derived from suitable database entries, e.g. at Genbank or Uniprot with date of Nov. 11, 2015.

ZBP1: DLM1 encodes a Z-DNA binding protein. Z-DNA formation is a dynamic process, largely controlled by the amount of supercoiling. May play a role in host defense against tumors and pathogens. Binds Z-DNA (By similarity). The amino acid and/or nucleotide sequence of this determinant would be know to the skilled person or can be derived from suitable database entries, e.g. at Genbank or Uniprot with date of Nov. 11, 2015.

The present inventin also envisages the use of other determinants in the form of non-polypeptide determinants, such as age, absolute neutrophil count (ANC), absolute lymphocyte count (ALC), neutrophil % (Neu (%)), lymphocyte % (Lym (%)), monocyte % (Mono (%)), Maximal temperature, Time from symptoms, Creatinine (Cr), Potassium (K), Pulse and Urea. The term "neutrophil % (Neu (%))" refers to the fraction of white blood cells that are lymphocytes. The term "lymphocyte % (Lym (%))" refers to the fraction of white blood cells that are lymphocytes. The term "monocyte % (Mono (%))" refers to the fraction of white blood cells that are monocytes.

Particularly preferred other determinants are TRAIL and CRP. Also preferred are determinants such as procalcitonin, CD64, IP 10, ILIRa or Mac-2BP. The present invention thus envisages the measuring of HNL in combination with TRAIL, the measuring of HNL in combination with CRP, as well as the measuring of HNL with procalcitonin, the measuring of HNL with CD64, the measuring of HNL in combination with IP 10, the measuring of HNL in combination with ILIRa, the measuring of HNL in combination with Mac-2BP, or the measuring of HNL in combination with one or more of TRAIL, IP 10, ILIRa and Mac-2BP. Also preferred are the non-polypeptide determinants absolute neutrophil count (ANC) and neutrophil % (Neu (%)).

In another embodiment, the level of the determinants absolute neutrophil count (ANC) and neutrophil % (NEU (%)) are used to normalize the level of HNL. Such a normalization may be performed by correlating the neutrophils (ANC) or the Neu % to the measured HNL.

Accordingly, in one embodiment of the above described method of ruling out a bacterial infection or ruling in a viral infection said method further comprises
a) measuring the polypeptide concentration of TRAIL in a sample obtained from a subject; and
b) ruling out a bacterial infection or ruling in a viral infection for the subject if the polypeptide concentration of TRAIL determined in step (a) is higher than a pre-determined first threshold value.

In another embodiment of the above described method of ruling out a viral infection or the method of ruling in a bacterial infection said method further comprises
a) measuring the polypeptide concentration of TRAIL in a sample obtained from a subject; and
b) ruling in a bacterial infection or ruling out a viral infection for the subject if the polypeptide concentration of TRAIL determined in step (a) is lower than a pre-determined first threshold value.

Moreover, in a further embodiment, the method of providing a treatment recommendation for a subject further comprises in step a) additionally measuring the polypeptide concentration of TRAIL in a sample obtained from a subject; and
b) recommending that the subject receives an antibiotic treatment if the polypeptide concentration of HNL determined in step (a) is higher than a pre-determined threshold value and if the concentration of TRAIL determined in step (a) is lower than a pre-determined threshold value;
c) recommending that the patient does not receive an antibiotic treatment if the polypeptide concentration of HNL determined in step (a) is lower than a predetermined threshold value and if the polypeptide concentration of TRAIL determined in step (a) is higher than a predetermined threshold value; or
d) recommending that the patient receive an anti-viral treatment if the polypeptide concentration of HNL determined in step (a) is lower than a pre-determined threshold value and if the polypeptide concentration of TRAIL determined in step (a) is higher than a predetermined threshold value, as defined herein above.

According to another embodiment, the method of providing a diagnostic test recommendation for a subject, further comprises in step a) additionally measuring the polypeptide concentration of TRAIL in a sample obtained from a subject; and
b) recommending testing the sample for the presence of bacteria if the polypeptide concentration of HNL determined in step (a) is higher than a pre-determined threshold value and if the concentration of TRAIL determined in step (a) is lower than a pre-determined threshold value;
c) recommending testing the sample for the presence of a virus if the polypeptide concentration of HNL determined in step (a) is lower than a predetermined threshold value and if the polypeptide concentration of TRAIL determined in step (a) is higher than a predetermined threshold value.

Also envisaged is a method of ruling out an infectious disease, preferably a bacterial or viral disease, in a subject comprising:
a) measuring the polypeptide concentration of HNL using a binding agent as defined above, or a diagnostic composition or kit as defined above, and the polypeptide concentration of one or more polypeptides selected from the group consisting of TRAIL, IP10, ILIRa or Mac-2BP in a sample obtained from a subject;
b) applying a pre-determined mathematical function on the concentrations of the polypeptides measured to compute a score
c) comparing the score to a predetermined reference value.

A "reference value" as used herein can be relative to a number or value derived from population studies, including without limitation, such subjects having the same infection, subject having the same or similar age range, subjects in the same or similar ethnic group, or relative to the starting sample of a subject undergoing treatment for an infection. Such reference values can be derived from statistical analyses and/or risk prediction data of populations obtained from mathematical algorithms and computed indices of infection. Reference determinant indices can also be constructed and used using algorithms and other methods of statistical and structural classification.

In one embodiment of the present invention, the reference value is the amount (i.e. level) of determinants in a control sample derived from one or more subjects who do not have an infection (i.e., healthy, and or non-infectious individuals). In a further embodiment, such subjects are monitored and/or periodically retested for a diagnostically relevant period of time ("longitudinal studies") following such test to verify continued absence of infection. Such period of time may be one day, two days, two to five days, five days, five to ten days, ten days, or ten or more days from the initial testing date for determination of the reference value.

Furthermore, retrospective measurement of determinants in properly banked historical subject samples may be used in establishing these reference values, thus shortening the study time required.

A reference value can also comprise the amounts of determinants derived from subjects who show an improvement as a result of treatments and/or therapies for the infection. A reference value can also comprise the amounts of determinants derived from subjects who have confirmed infection by known techniques.

In another embodiment, the reference value is an index value or a baseline value. An index value or baseline value is a composite sample of an effective amount of determinants from one or more subjects who do not have an infection. A baseline value can also comprise the amounts of determinants in a sample derived from a subject who has shown an improvement in treatments or therapies for the infection. In this embodiment, to make comparisons to the subject-derived sample, the amounts of determinants are similarly calculated and compared to the index value. Optionally, subjects identified as having an infection, are chosen to receive a therapeutic regimen to slow the progression or eliminate the infection.

Additionally, the amount of the determinant can be measured in a test sample and compared to the "normal control level," utilizing techniques such as reference limits, discrimination limits, or risk defining thresholds to define cutoff points and abnormal values. The "normal control level" means the level of one or more determinants or combined determinant indices typically found in a subject not suffering from an infection. Such normal control level and cutoff points may vary based on whether a determinant is used alone or in a formula combining with other determinants into an index. Alternatively, the normal control level can be a database of determinant patterns from previously tested subjects.

The effectiveness of a treatment regimen can be monitored by detecting a determinant in an effective amount (which may be one or more) of samples obtained from a subject over time and comparing the amount of determinants detected. For example, a first sample can be obtained prior to the subject receiving treatment and one or more subsequent samples are taken after or during treatment of the subject.

For example, the methods of the invention can be used to discriminate between bacterial, viral and mixed infections (i.e. bacterial and viral co-infections.) This will allow patients to be stratified and treated accordingly.

Any formula may be used to combine determinant results into indices useful in the practice of the invention. As indicated above, and without limitation, such indices may indicate, among the various other indications, the probability, likelihood, absolute or relative risk, time to or rate of conversion from one to another disease states, or make predictions of future biomarker measurements of infection. This may be for a specific time period or horizon, or for remaining lifetime risk, or simply be provided as an index relative to another reference subject population.

Although various preferred formula are described here, several other model and formula types beyond those mentioned herein and in the definitions above are well known to one skilled in the art. The actual model type or formula used may itself be selected from the field of potential models based on the performance and diagnostic accuracy characteristics of its results in a training population. The specifics of the formula itself may commonly be derived from determinant results in the relevant training population. Amongst other uses, such formula may be intended to map the feature space derived from one or more determinant inputs to a set of subject classes (e.g. useful in predicting class membership of subjects as normal, having an infection), to derive an estimation of a probability function of risk using a Bayesian approach, or to estimate the class-conditional probabilities, then use Bayes' rule to produce the class probability function as in the previous case.

Preferred formulas include the broad class of statistical classification algorithms, and in particular the use of discriminant analysis. The goal of discriminant analysis is to predict class membership from a previously identified set of features. In the case of linear discriminant analysis (LDA), the linear combination of features is identified that maximizes the separation among groups by some criteria. Features can be identified for LDA using an eigengene based approach with different thresholds (ELD A) or a stepping algorithm based on a multivariate analysis of variance (MANOVA). Forward, backward, and stepwise algorithms can be performed that minimize the probability of no separation based on the Hotelling-Lawley statistic.

Eigengene-based Linear Discriminant Analysis (ELD A) is a feature selection technique developed by Shen et al. (2006). The formula selects features (e.g. biomarkers) in a multivariate framework using a modified eigen analysis to identify features associated with the most important eigenvectors. "Important" is defined as those eigenvectors that explain the most variance in the differences among samples that are trying to be classified relative to some threshold.

A support vector machine (SVM) is a classification formula that attempts to find a hyperplane that separates two classes. This hyperplane contains support vectors, data points that are exactly the margin distance away from the hyperplane. In the likely event that no separating hyperplane exists in the current dimensions of the data, the dimensionality is expanded greatly by projecting the data into larger dimensions by taking non-linear functions of the original variables (Venables and Ripley, 2002). Although not required, filtering of features for SVM often improves prediction. Features (e.g., biomarkers) can be identified for a support vector machine using a non-parametric Kruskal-Wallis (KW) test to select the best univariate features. A random forest (RF, Breiman, 2001) or recursive partitioning (RPART, Breiman et al., 1984) can also be used separately or in combination to identify biomarker combinations that are most important. Both KW and RF require that a number of features be selected from the total. RPART creates a single classification tree using a subset of available biomarkers. Other formula may be used in order to pre-process the results of individual determinant measurement into more valuable forms of information, prior to their presentation to the predictive formula. Most notably, normalization of biomarker results, using either common mathematical transformations such as logarithmic or logistic functions, as normal or other distribution positions, in reference to a population's mean values, etc. are all well known to those skilled in the art. Of particular interest are a set of normalizations based on clinical-determinants such as age, time from symptoms, gender, race, or sex, where specific formula are used solely on subjects within a class or continuously combining a clinical-determinants as an input. In other cases, analyte-based biomarkers can be combined into calculated variables which are subsequently presented to a formula.

In addition to the individual parameter values of one subject potentially being normalized, an overall predictive formula for all subjects, or any known class of subjects, may itself be recalibrated or otherwise adjusted based on adjustment for a population's expected prevalence and mean biomarker parameter values, according to the technique outlined in D'Agostino et al, (2001) JAMA 286:180-187, or other similar normalization and recalibration techniques. Such epidemiological adjustment statistics may be captured, confirmed, improved and updated continuously through a registry of past data presented to the model, which may be machine readable or otherwise, or occasionally through the retrospective query of stored samples or reference to historical studies of such parameters and statistics. Additional examples that may be the subject of formula recalibration or other adjustments include statistics used in studies by Pepe, M.S. et al, 2004 on the limitations of odds ratios; Cook, N. R., 2007 relating to ROC curves. Finally, the numeric result of a classifier formula itself may be transformed postprocessing by its reference to an actual clinical population and study results and observed endpoints, in order to calibrate to absolute risk and provide confidence intervals for varying numeric results of the classifier or risk formula.

Some determinants may exhibit trends that depends on the patient age (e.g. the population baseline may rise or fall as a function of age), which may be used as non-polypeptide determinant as described herein above. An Age dependent normalization or stratification' scheme may thus be used to adjust for age related differences. Performing age dependent normalization or stratification can be used to improve the accuracy of determinants for differentiating between different types of infections. For example, one skilled in the art can generate a function that fits the population mean levels of each determinant as function of age and use it to normalize the determinant of individual subjects levels across different ages. Another example is to stratify subjects according to their age and determine age specific thresholds or index values for each age group independently.

The performance and thus absolute and relative clinical usefulness of the invention may be assessed in multiple ways as noted above. Amongst the various assessments of performance, the invention is intended to provide accuracy in clinical diagnosis and prognosis. The accuracy of a diagnostic or prognostic test, assay, or method concerns the ability of the test, assay, or method to distinguish between subjects having an infection is based on whether the subjects have, a "significant alteration" (e.g., clinically significant "diagnostically significant) in the levels of a determinant. By "effective amount" it is meant that the measurement of an appropriate number of determinants (which may be one or more) to produce a "significant alteration" (e.g. level of expression or activity of a determinant) that is different than the predetermined cut-off point (or threshold value) for that determinant(s) and therefore indicates that the subject has an infection for which the determinant(s) is a determinant. The difference in the level of determinant is preferably statistically significant. As noted below, and without any limitation of the invention, achieving statistical significance, and thus the preferred analytical, diagnostic, and clinical accuracy, generally but not always requires that combinations of several determinants to be used together in panels and combined with mathematical algorithms in order to achieve a statistically significant determinant index.

In the categorical diagnosis of a disease state, changing the cut point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points. One way to achieve this is by using the MCC metric, which depends upon both sensitivity and specificity. Use of statistics such as AUC, encompassing all potential cut point values, is preferred for most categorical risk measures using the invention, while for continuous risk measures, statistics of goodness-of-fit and calibration to observed results or other gold standards, are preferred.

Ther term "MCC" means Mathwes Correlation coefficient and is calculated as follows: MCC=(TP*TN−FP*FN)/{(TP+FN)*(TP+FP)*(TN+FP)*(TN+FN)}<A>0.5 where TP, FP, TN, FN are true-positives, false-positives, true-negatives, and false-negatives, respectively. Note that MCC values range between −1 to +1, indicating completely wrong and perfect classification, respectively. An MCC of 0 indicates random classification. MCC has been shown to be a useful for combining sensitivity and specificity into a signle metric (Baldi, Brunak et al. 2000). It is also useful for measuring and optimizing classification accuracy in cases of unbalanced class sizes (Baldi, Brunak et al. 2000).

The MCC values may range between −1 to +1, indicating completely wrong and perfect classification, respectively. An MCC of 0 indicates random classification. It has been shown that the MCC is especially useful for measuring and optimizing classification accuracy in cases of unbalanced class sizes (Baldi, Brunak et al. 2000). The differential diagnosis of determinants may be evaluated using a linear classification scheme, in which the cutoff that maximizes the MCC on the train set is computed and then used to classify the patients in the test set.

The term "TP" means "true positive", i.e. a positive test result that accurately reflects the tested-for activity. For example in the context of the present invention a TP, is for example but not limited to, truly classifying a bacterial infection as such.

"TN" is true negative and means negative test result that accurately reflects the tested-for activity. For example in the context of the present invention a TN, is for example but not limited to, truly classifying a viral infection as such.

"FN" is false negative and means a result that appears negative but fails to reveal a situation. For example in the context of the present invention a FN, is for example but not limited to, falsely classifying a bacterial infection as a viral infection.

"FP" is false positive and means test result that is erroneously classified in a positive category. For example in the context of the present invention a FP, is for example but not limited to, falsely classifying a viral infection as a bacterial infection "Sensitivity" is calculated by TP/(TP+FN) or the true positive fraction of disease subjects. "Specificity" is calculated by TN/(TN+FP) or the true negative fraction of non-disease or normal subjects. "Total accuracy" is calculated by (TN+TP)/(TN+FP+TP+FN). "Positive predictive value" or "PPV" is calculated by TP/(TP+FP) or the true positive fraction of all positive test results. It is inherently impacted by the prevalence of the disease and pre-test probability of the population intended to be tested. "Negative predictive value" or "NPV" is calculated by TN/(TN+FN) or the true negative fraction of all negative test results. It also is inherently impacted by the prevalence of the disease and pre-test probability of the population intended to be tested. See, e.g., O'Marcaigh AS, Jacobson RM, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test.

The term "accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), Matheus correlation coefficient (MCC), or as a likelihood, odds ratio, Receiver Operating Charachteristic (ROC) curve, Area Under the Curve (AUC) among other measures.

Often, for binary disease state classification approaches using a continuous diagnostic test measurement, the sensitivity and specificity is summarized by a Receiver Operating Characteristics (ROC) curve according to Pepe et al, "Limitations of the Odds Ratio in Gauging the Performance of a Diagnostic, Prognostic, or Screening Marker," Am. J. Epidemiol 2004, 159 (9): 882-890, and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), 4th edition 1996, W. B. Saunders Company, pages 192-199; and Zweig et al., "ROC Curve Analysis: An Example Showing The Relationships Among Serum Lipid And Apolipoprotein Concentrations In Identifying Subjects With Coronory Artery Disease," Clin. Chem., 1992, 38(8): 1425-1428. An alternative approach using likelihood functions, odds ratios, information theory, predictive values, calibration (including goodness-of-fit), and reclassification measurements is summarized according to Cook, "Use and Misuse of the Receiver Operating Characteristic Curve in Risk Prediction," Circulation 2007, 115:928-935.

A "formula," "algorithm," or "model" as used herein is any mathematical equation, algorithmic, analytical or programmed process, or statistical technique that takes one or more continuous or categorical inputs (herein called "parameters") and calculates an output value, sometimes referred to as an "index" or "index value". Non-limiting examples of "formulas" include sums, ratios, and regression operators, such as coefficients or exponents, biomarker value transformations and normalizations (including, without limitation, those normalization schemes based on clinical-determinants, such as gender, age, or ethnicity), rules and guidelines, statistical classification models, and neural networks trained on historical populations. Of particular use in combining determinants are linear and non-linear equations and statistical classification analyses to determine the relationship between levels of determinants detected in a subject sample and the subject's probability of having an infection or a certain type of infection. In panel and combination construction, of particular interest are structural and syntactic statistical classification algorithms, and methods of index construction, utilizing pattern recognition features, including established techniques such as cross-correlation, Principal Components Analysis (PCA), factor rotation, Logistic Regression (LogReg), Linear Discriminant Analysis (LDA), Eigengene Linear Discriminant Analysis (ELD A), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, and Hidden Markov Models, among others. Other techniques may be used in survival and time to event hazard analysis, including Cox, Weibull, Kaplan-Meier and Greenwood models well known to those of skill in the art. Many of these techniques are useful either combined with a determinant selection technique, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art. A "health economic utility function" is a formula that is derived from a combination of the expected probability of a range of clinical outcomes in an idealized applicable patient population, both before and after the introduction of a diagnostic or therapeutic intervention into the standard of care. It encompasses estimates of the accuracy, effectiveness and performance characteristics of such intervention, and a cost and/or value measurement (a utility) associated with each outcome, which may be derived from actual health system costs of care (services, supplies, devices and drugs, etc.) and/or as an estimated acceptable value per quality adjusted life year (QALY) resulting in each outcome. The sum, across all predicted outcomes, of the product of the predicted population size for an outcome multiplied by the respective outcome's expected utility is the total health economic utility of a given standard of care. The difference between (i) the total health economic utility calculated for the standard of care with the intervention versus (ii) the total health economic utility for the standard of care without the intervention results in an overall measure of the health economic cost or value of the intervention. This may itself be divided amongst the entire patient group being analyzed (or solely amongst the intervention group) to arrive at a cost per unit intervention, and to guide such decisions as market positioning, pricing, and assumptions of health system acceptance. Such health economic utility functions are commonly used to compare the cost-effectiveness of the intervention, but may also be transformed to estimate the acceptable value per QALY the health care system is willing to pay, or the acceptable cost-effective clinical performance characteristics required of a new intervention.

For diagnostic (or prognostic) interventions of the invention, as each outcome (which in a disease classifying diagnostic test may be a TP, FP, TN, or FN) bears a different cost, a health economic utility function may preferentially favor sensitivity over specificity, or PPV over NPV based on the clinical situation and individual outcome costs and value, and thus provides another measure of health economic performance and value which may be different from more direct clinical or analytical performance measures. These different measurements and relative trade-offs generally will converge only in the case of a perfect test, with zero error rate (a.k.a., zero predicted subject outcome misclassifications or FP and FN), which all performance measures will favor over imperfection, but to differing degrees.

In a further aspect the present invention accordingly relates to a method of distinguishing between a bacterial infection and a viral infection in a subject comprising:
a) measuring the polypeptide concentration of HNL using a binding agent as defined above or a diagnostic composition or kit as defined above, and of CRP, optionally of TRAIL, in a sample obtained from a subject;
b) applying a pre-determined mathematical function on the concentrations of HNL and CRP and optionally of TRAIL, to compute a score;
c) comparing the score, as defined herein above, to a predetermined reference value, as defined herein above.

In a further aspect the present invention accordingly provides a method of distinguishing between a bacterial or mixed infection, and a viral infection in a subject comprising:
a) measuring the polypeptide concentration of HNL using a binding agent as defined above, or a diagnostic composition or kit as defined above, and of CRP, optionally of TRAIL, in a sample obtained from a subject;
b) applying a pre-determined mathematical function on the concentrations of HNL and CRP and optionally of TRAI, to compute a score;
c) comparing the score, as defined herein above, to a predetermined reference value, as defined herein above.

In yet another aspect, a method of identifying the type of infection, preferably a bacterial or viral infection, in a subject is provided, comprising:
a) measuring the polypeptide concentration of HNL using a binding agent as defined in any one of claims 1 to 5, or a diagnostic composition or kit according to claims 6 or 7 and the levels of a first polypeptide determinant, as defined herein above, selected from the group consisting of TRAIL, IL1RA, IP 10, Mac-2BP, B2M, BCA-1, CHI3L1, Eotaxin, IL1a, MCP, CD62L, VEGFR2, CHP, CMPK2, CORO1C, EIF2AK2, ISG15, RPL22L1, RTN3, CD112, CD134, CD182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, IgG non-specific bound molecules, IL1, I-TAC and TNFR1 in a sample obtained from a subject; and
b) measuring the levels of a second determinant selected from the group consisting of
  (i) the polypeptide determinants, as defined herein above, TRAIL, IL1RA, IP10, Mac-2BP, B2M, BCA-1, CHI3L1, Eotaxin, IL1a, MCP, CD62L, VEGFR2, CHP, CMPK2, CORO1C, EIF2AK2, ISG15, RPL22L1, RTN3, CD 112, CD 134, CD 182, CD231, CD235A, CD335, CD337, CD45, CD49D, CD66A/C/D/E, CD73, CD84, EGFR, GPR162, HLA-A/B/C, ITGAM, NRG1, RAP1B, SELI, SPINT2, SSEA1, IgG nonspecific bound molecules, IL1, I-TAC and TNFR1;
  (ii) the polypeptide determinants, as defined herein above, IFITM3, IFIT3, EIF4B, IFIT1, LOC26010, MBOAT2, MX1, OAS2, RSAD2, ADIPOR1, CD15, CD8A, IFITM1, and IL7;
  (iii) the polypeptide determinants, as defined herein above CRP, SAA, TREM-1, PCT, IL-8, TREM-1 and IL6; or
  (iv) the non-polypeptide determinants, as defined herein above, Age, absolute neutrophil count (ANC), absolute lymphocyte count (ALC), neutrophil % (Neu (%)), lymphocyte % (Lym (%)), monocyte % (Mono (%)), Maximal temperature, Time from symptoms, Creatinine (Cr), Potassium (K), Pulse and Urea;
c) comparing the levels of HNL, first and second determinants to a reference value thereby identifying the type of infection in the subject wherein the measurement of the first and/or second determinant increases the accuracy of the identification of the type of infection over the measurement of HNL.

"Type of infection" as used herein means to include bacterial infections, viral infections, mixed infections, no infection (i.e., non-infectious). More specifically, some methods of the invention are used to distinguish subjects having a bacterial infection, a viral infection, a mixed infection (i.e., bacterial and viral co-infection), patients with a non-infectious disease and healthy individuals.

As a matter of convenience, an antibody disclosed herein can be provided in a kit, i.e., a packaged combination of reagents in predetermined amounts with instructions for performing the diagnostic assay. Where the antibody is labeled with an enzyme, the kit will include substrates and co factors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Also provided are diagnostic reagents and kits comprising one or more such reagents for use in a variety of diagnostic assays, including for example, immunoassays such as ELISA (sandwich-type or competitive format). In some embodiments, such kits may include at least a first peptide (optionally a properly folded mature HNL standard as described herein), or a first antibody or antigen binding fragment described herein, a functional fragment thereof, or a cocktail thereof, and means for signal generation. The kit's components may be pre-attached to a solid support, or may be applied to the surface of a solid support when the kit is used. In some embodiment, the signal generating means may come pre-associated with an antibody described herein or may require combination with one or more components, e.g., buffers, antibody-enzyme conjugates, enzyme substrates, or the like, prior to use. Kits may also include additional reagents, e.g., blocking reagents for reducing nonspecific binding to the solid phase surface, washing reagents, enzyme substrates, and the like. The solid phase surface may be in the form of a tube, a bead, a microtiter plate, a microsphere, or other materials suitable for immobilizing proteins, peptides, or polypeptides. In some embodiments, an enzyme that catalyzes the formation of a chemiluminescent or chromogenic product or the reduction of a chemiluminescent or chromogenic substrate is a component of the signal generating means. Such enzymes are well known in the art. Kits may comprise any of the capture agents and detection reagents described herein. Optionally the kit may also comprise instructions for carrying out the methods described herein. The kits may further comprise agents for detection and measuring of other biological parameters, e.g. agents for measuring the expression and amount of procalcitonin, C-reactive protein, CD64, or of any of the polypeptide determinants mentioned herein above, and for the determination of numbers of white blood cells, e.g. neutrophils, T-cells, B-cells, monocytes, eosinophils, basophils.

The diagnostic kits disclosed herein may also be prepared that comprise at least one of the antibody, peptide, antigen binding fragment, or polynucleotide disclosed herein and instructions for using the composition as a diagnostic reagent or therapeutic agent. Containers for use in such kits may typically comprise at least one vial, test tube, flask, bottle, syringe or other suitable container, into which one or more of the diagnostic and/or therapeutic composition(s) may be placed, and suitably aliquoted. Where a second therapeutic agent is also provided, the kit may also contain a second distinct container into which this second diagnostic and/or therapeutic composition may be placed. Alternatively, a plurality of compounds may be prepared in a single pharmaceutical composition, and may be packaged in a single container means, such as a vial, flask, syringe, bottle, or other suitable single container. The kits of the present invention will also typically include a means for containing the vial(s) in close confinement for commercial sale, such as, e.g., injection or blow-molded plastic containers into which the desired vial(s) are retained. Where a radiolabel, chromogenic, fluorigenic, or other type of detectable label or detecting means is included within the kit, the labeling agent may be provided either in the same container as the diagnostic or therapeutic composition itself, or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery.

A device or apparatus for carrying out the diagnostic or monitoring methods described herein is also provided. Such an apparatus may include a chamber or tube into which sample can be input, a fluid handling system optionally including valves or pumps to direct flow of the sample through the device, optionally filters to separate plasma or serum from blood, mixing chambers for the addition of capture agents or detection reagents, and optionally a detection device for detecting the amount of detectable label bound to the capture agent immunocomplex. The flow of sample may be passive (e.g., by capillary, hydrostatic, or other forces that do not require further manipulation of the device once sample is applied) or active (e.g., by application of force generated via mechanical pumps, electroosmotic pumps, centrifugal force, or increased air pressure), or by a combination of active and passive forces. Devices for detection of analytes that involve magnetic based separation of the analytes of interest (for example the device disclosed in WO2008/072156, WO2008/102218, WO2010/035204, and WO2011/036638) can also be used to performed the tests and methods disclosed herein.

In related embodiments, also provided is a processor, a computer readable memory, and a routine stored on the computer readable memory and adapted to be executed on the processor to perform any of the methods described herein, and/or to generate as output the detected level of HNL and a threshold or range of threshold levels considered "normal", such that levels outside the "normal" range correlate with one or more of the conditions as described herein.

In some embodiments, computer readable media containing programs or routines to perform similar functions are also provided. Examples of suitable computing systems, environments, and/or configurations include personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, or any other systems known in the art.

The antibodies disclosed herein may be used in diagnostic assays for target antigen, e.g., detecting its expression in specific cells, tissues, or serum. The antibodies may also be used for in vivo diagnostic assays. Generally, for these purposes the antibody is labeled with a radionuclide so that the site can be localized using immunoscintiography.

The antibodies disclosed herein may be employed in any known assay method, such as competitive binding assays, direct and indirect sandwich assays, such as ELISAs, and immunoprecipitation assays. Zola, Monoclonal Antibodies: A Manual of Techniques, pp.147-158 (CRC Press, Inc. 1987). The antibodies may also be used for immunohistochemistry, to label cell samples using methods known in the art.

Experiments

1. Characterization of the antibodies and the HNL epitopes
   Epitope Mapping by High-Mass MALDI mass spectrometry Before starting the epitope mapping, a high-mass MALDI analysis has been performed on each sample (Antibodies and Antigen) in order to verify their integrity and aggregation level. For the integrity/aggregation test, the measurements were performed using an Ultraflex III MALDI ToF mass spectrometer (Bruker) equipped with CovalX's HM3 interaction module. CovalX's interaction module contains a special detecting system designed to optimize detection up to 2MDa with nano-molar sensitivity. 20 µl of each protein sample (Anti-HNL clone MAB1; Clone MAB2 and Clone MAB3 and HNL were pipetted to prepare 8 dilutions with final volume 10 µl. The concentration of the antibodies in these dilutions were 1.0 mg/ml, 0.5 mg/ml, 250 (µg/ml, 125 (µg/ml, 62.5 (µg/ml, 31.25 (µg/ml, 15.63 µg/ml, 7.82 µg/ml. HNL antigen was diluted to provide the following concentrations: 350 µg/ml, 175 µg/ml, 87.5 µg/ml, 43.75 µg/ml, 21.88 µg/ml, 10.94 µg/ml, 5.47 µg/ml, and 2.74 µg/ml. These 8 dilutions of the samples were prepared in order to obtain the following expected concentrations:

1 µl of each dilution obtained was mixed with 1 µl of a matrix composed of a re-crystallized sinapinic acid matrix (10 mg/ml) in acetonitrile/water (1:1, v/v), TFA 0.1% (K200 MALDI Kit). After mixing, 1 µl of each sample was spotted on the MALDI plate (SCOUT 384). After crystallization at room temperature, the plate was introduced in the MALDI mass spectrometer and analysed immediately in High-Mass MALDI mode. The analysis has been repeated in triplicate.

Cross-linking experiments allow the direct analysis of non-covalent interaction by High-Mass MALDI mass spectrometry. By mixing a protein sample containing non covalent interactions with a specially developed cross-linking mixture (Bich, C. et al. Anal. Chem., 2010, 82 (1), pp 172-179), it is possible to specifically detect non covalent complex with high-sensitivity. The covalent binding generated allows the interacting species to survive the sample preparation process and the MALDI ionization. A special High-Mass detection system allows characterizing the interaction in the High-Mass range.

Each mixture prepared for the control experiment (9 µl left) was submitted to cross-linking using CovalX's K200 MALDI MS analysis kit. 9 µl of the mixtures (from 1 to 1/128) is mixed with 1 µl of K200 Stabilizer reagent (2 mg/ml) and incubated at room temperature. After the incubation time (180 minutes) the samples were prepared for MALDI analysis as for Control experiments. The samples are analysed by High-Mass MALDI analysis immediately after crystallization. The MALDI ToF MS analysis has been performed using CovalX's HM3 interaction module with a standard nitrogen laser and focusing on different mass ranges from 0 to 1500 kDa. For the analysis, the following parameters have been applied: Mass Spectrometer: Linear and Positive mode, Ion Source 1:20 kV, Ion Source 2:17 kV, Lens: 12 kV, Pulse Ion Extraction: 400 ns, HM3: Gain Voltage: 3.14 kV, Acceleration Voltage: 20 kV Results Antibody Anti-HNL MAB1

In control experiments, one main peak for every dilution from 1 to ¹/₆₄ with MH+=146.935±0.098 kDa was detected. The observed molecular weight (kDa) is 146.935±0.098 Anti-HNL MAB1.

In cross-link experiments, one main peak for every dilution from 1 to ¹/₆₄ with MH+=148.717±0.112 kDa was detected. The observed molecular weight (kDa) is 148.717±0.112 Anti-HNL MAB1. No other non-covalent complexes have been detected in the higher mass range. Further, using complex tracker software no non-covalent complexes (were detected).

Antibody Anti-HNL MAB2

In control experiments, one main peak for every dilution from 1 to ¹/₆₄ with MH+=152.657±0.115 kDa was detected. The observed molecular weight (kDa) is 152.657±0.115 Anti-HNL MAB2

In cross-link experiments, one main peak for every dilution from 1 to ¹/₆₄ with MH+=154.521±0.142 kDa was detected. The observed molecular weight (kDa) is 154.521±0.142 Anti-HNL MAB2. No other non-covalent complexes have been detected in the higher mass range. Using complex tracker software non-covalent complexes were not detected.

Antibody Anti-HNL MAB3

In control experiments, one main peak for every dilution from 1 to ¹/₆₄ with MH+=147.717±0.133 kDa was detected. The observed molecular weight (kDa) is 147.717±0.133 Anti-HNL MAB3.

In cross-link experiments, one main peak for every dilution from 1 to ¹/₆₄ with MH+=149.134±0.089 kDa was detected. The observed molecular weight (kDa) is 149.134±0.089 Anti-HNL MAB3. No other non-covalent complexes have been detected in the higher mass range. Using complex tracker software no non-covalent complexes was detected.

Antigen HNL

In control experiments, one main peak for every dilution from 1 to ¹/₃₂ with MH+=45.431±0.33 kDa was detected. The observed molecular weight (kDa) is 45.431±0.33.

In cross-link experiments, one main peak for every dilution from 1 to ¹/₃₂ with MH+=48.509±0.052 kDa was detected. The observed molecular weight (kDa) is 48.509±0.052. No other non-covalent complexes have been detected in the higher mass range. Using complex tracker software no non-covalent complexes was detected.

Conclusion Aggregation Test

Using High-Mass MALDI mass spectrometry and chemical cross-linking, no noncovalent aggregates of the antibody anti-HNL and multimers of the antigens HNL was detected.

Characterization of the Nature of the Epitope

In order to determine the nature of the epitope (i.e. linear or conformational), it was evaluated if the interaction between the antigen proteins and the antibodies can be inhibited by unstructured peptides generated by proteolysis of the antigen.

If the peptides generated by complete proteolysis of the antigen are able to inhibit the binding of the antigen on the antibody, the interaction is not based on conformation. In this case the epitope is linear. A simple competition assay with a bank of overlapping peptides generated from the sequence of the antigen will be sufficient to determine the sequence of the epitope.

If the peptides generated by complete proteolysis of the antigen are unable to inhibit the binding of the antigen on the antibody, the conformation is necessary for interaction. In this case the epitope can be continue (with a special conformation, i.e. loop) or discontinue (due to tertiary structure). In this case the use of covalent labeling, peptide mapping, and high resolution mass spectrometry will be necessary.

For characterizing the nature of the epitope, the measurements were performed using an Ultraflex III MALDI ToF mass spectrometer (Bruker) equipped with CovalX's HM3 High-Mass system.

Control Experiments

Mix of mAb/Ags (Anti HNL MAB1/HNL; Anti HNL MAB2/HNL and Anti HNL MAB3/HNL) were prepared. 1 µl of the mixture obtained was mixed with 1 µl of a matrix composed of a re-crystallized sinapinic acid matrix (10 mg/ml) in acetonitrile/water (1:1, v/v), TFA 0.1% (K200 MALDI Kit). After mixing, 1 µl of each sample was spotted on the MALDI plate (SCOUT 384). After crystallization at room temperature, the plate was introduced in the MALDI mass spectrometer and analysed immediately. The analysis was repeated in triplicate.

Cross-Link Experiments

The mixture prepared for the control experiment (9 µl left) was submitted to cross-linking using CovalX's K200 MALDI MS analysis kit. 9 µl of the mixture is mixed with 1 µl of K200 Stabilizer reagent (2 mg/ml) and incubated at room temperature. After the incubation time (180 minutes) the samples were prepared for MALDI analysis as for Control experiments. The samples are analysed by High-Mass MALDI analysis immediately after crystallization.

Competition Assay

In order to determine the nature of the epitope, a proteolysis of HNL antigen with immobilized pepsin was performed. 25 µl of the antigen with a concentration of 10 µM were mixed with immobilized pepsin 2.5 µM and incubate at room temperature for 30 minutes. After the incubation time the sample is centrifuged and the supernatant was pipetted. The completion of the proteolysis is controlled by High-Mass MALDI mass spectrometry in linear mode and reflectron mode. The pepsin proteolysis was optimized in order to obtain a large amount of peptide in the 1000-3500 Da range. 5 µl of the antigen peptides generated by proteolysis (7.6 µM) were mixed with 5 µl of Anti-HNL antibody (3.8 µM) and incubated at 37° for 2 hours. After incubation of the antibodies with the antigen peptides, 5 µl of the mixture is mixed with 5 µl of the intact antigen (3.8 µM).

Interaction Analysis

For the competition assay, the antibody/antigen interaction analysis was performed with the same protocol (Control and Cross-link experiments) described above.

High-Mass MALDI MS analysis

The MALDI ToF MS analysis has been performed using CovalX's HM3 interaction module with a standard nitrogen laser and focusing on different mass ranges from 0 to 2000 kDa. For the analysis, the following parameters have been applied: Mass Spectrometer: Linear and Positive mode; Ion Source 1:20 kV; Ion Source 2:17 kV; Lens: 12 kV; Pulse Ion Extraction: 400 ns; HM3:Gain Voltage: 3.14 kV; Acceleration Voltage: 20 kV. To calibrate the instrument, an external calibration with clusters of Insulin, BSA and IgG was applied. For each sample, 3 spots were analyzed (300 laser shots per spots). The presented spectrum corresponds to the sum of 300 laser shots. The MS data were analyzed using CovalX's Complex Tracker analysis software version 2.0.

Results

Anti HNL MAB1/HNL

In control experiments, the antigen and the antibody had a MH+=45.862 kDa and MH+=148.577 kDa. Observed molecular weight (kDa) 45.725 HNL; 148.431 Anti-HNL MAB1.

A cross-linking experiment was completed after 180 minutes incubation time with the crosslinking reagent K200. After cross-linking, two additional peaks were detected with MH+=195.941 kDa and MH+=241.619 kDa. Using Complex Tracker software, we the control and cross-link spectra were overlaid. Two non-covalent complexes with the following stoichiometry were detected. The observed molecular weight (kDa) stoechiometry was 194.865 [Anti-HNL MAB1/HNL] and 241.287 [Anti-HNL MAB1/2HNL], respectively.

In competition experiments, no inhibition of the binding of the antibody Anti-HNL to antigen HNL was detected. The peptides of the antigen did not inhibit the binding of the antibody to the antigen.

Anti HNL MAB2/HNL

In control experiments, the antigen and the antibody had an MH+=45.755 kDa and MH+=148.531 kDa, respectively. The observed molecular weight (kDa) was 45.755 HNL, and 148.531 Anti-HNL MAB2.

A cross-linking experiment was completed after 180 minutes incubation time with the crosslinking reagent K200. After cross-linking, two additional peaks were detected with MH+=201.793 kDa and MH+=248.696 kDa. Using Complex Tracker software, the control and cross-link spectra was overlaid. Two non-covalent complexes with the following stoichiometry were detected: Observed Molecular Weight (kDa) Stoechiometry 194.881 [Anti-HNL MAB2/HNL] and 240.978 [Anti-HNL MAB2/2HNL].

In competition experiments, no inhibition of the binding of the antibody Anti-HNL to antigen HNL was detected. The peptides of the antigen did not inhibit the binding of the antibody to the antigen Anti HNL MAB3/HNL In control experiments, the antigen and the antibody were detected with MH+=45.742 kDa and MH+=148.554 kDa. The observed molecular weight (kDa) was 45.742 HNL and 148.554 Anti-HNL MAB3, respectively.

A cross-linking experiment was completed after 180 minutes incubation time with the crosslinking reagent K200. After cross-linking, two additional peaks were detected with MH+=196.482 kDa and MH+=243.468 kDa. Using Complex Tracker software, we overlaid the control and cross-link spectra. Two non-covalent complexes with the following stoichiometry were detected. The observed molecular weight (kDa) stoechiometry were 194.130 [Anti-HNL MAB3/HNL] and 240.793 [Anti-HNL MAB3/2HNL], respectively.

In competition experiments, no inhibition of the binding of the antibody Anti-HNL to antigen HNL was detected. The peptides of the antigen did not inhibit the binding of the antibody on the antigen.

Conclusion Competition Assay

The competition assay indicated that peptides of the antigen are not inhibiting the binding on the antibody on the antigen. The epitope of Anti-HNL on HNL is not linear.

Characterization and Peptide Mass Fingerprint of the antigen HNL

In order to characterize HNL, samples thereof were submitted to ASP-N, trypsin, chymotrypsin, elastase and thermolysin proteolysis followed by LC-LTQ Orbitrap MS/MS analysis. For the characterization of the antigen, a nano-LC chromatography was processed using a Ultimate 3000 (Dionex) system in line with a LTQ Orbitrap XL mass spectrometer (Thermo). 10 µl of the antigen (0.35 mg/mL) was mixed with 40 µl of ammonium bicarbonate (25 mM, pH 8.3). After mixing 2 µl of DTT (500 mM) is added to the solution. The mixture is then incubated 1 hour at 55° C. After incubation, 2 µl of iodioacetamide (1M) is added before 1 hour of incubation at room temperature in a dark room. After incubation, the solution is diluted ⅕ by adding 120 µl of the buffer used for the proteolysis with trypsin, chymotrypsin, ASP-N, elastase, or thermolysin:

145 µl of the reduced/alkyled antigen was mixed with 0.7 µl of trypsin (Roche Diagnostic) at ratio 1/100. The proteolytic mixture was incubated overnight at 37° C.

145 µl of the reduced/alkyled antigen was mixed with 0.35 µl of chymotrypsin (Roche Diagnostic) at ratio 1/200. The proteolytic mixture was incubated overnight at 25° C.

145 µl of the reduced/alkyled antigen was mixed with 0.35 µl of ASP-N (Roche Diagnostic) at ratio 1/200. The proteolytic mixture was incubated overnight at 37° C.

145 µl of the reduced/alkyled antigen was mixed with 0.70 µl of elastase (Roche Diagnostic) at ratio 1/100. The proteolytic mixture was incubated overnight at 37° C.

145 µl of the reduced/alkyled antigen was mixed with 1.40 µl of thermolysin (Roche Diagnostic) at ratio 1/50. The proteolytic mixture was incubated overnight at 70° C.

After proteolysis, 10 µl of the peptide generated by proteolysis were loaded onto a nano-liquid chromatography system (Ultimate 3000, Dionex) and subjected to analysis. DTA generation and Filtering was performed using LTQ OrbiTrap.

Characterization of the Molecular Interfaces

In order to determine the epitope of Anti-HNL MAB1; Anti-HNL MAB2 and Anti-HNL MAB3 on HNL antigen with high resolution the antibody/antigen complexes are incubated with deuterated cross-linkers and subjected to multi-enzymatic cleavage. After enrichment of the cross-linked peptides, the samples are analyzed by high resolution mass spectrometry (nLC-Orbitrap MS) and the data generated are analyzed using XQuest and Stavrox software.

Antibody/Antigen Complex

5 µl of the antigen sample (concentration 3.8 µM) was mixed with 5 µl of the antibody sample (Concentration 1.9 µM) in order to obtain an antibody/antigen mix with final concentration 0.95 µM/1.9 µM. The mixture was incubated at 37° C. for 180 minutes.

In a first step, 1 mg of d0 cross-linker was mixed with 1 mg of d12 cross-linker. The 2 mg prepared were mixed with 1 ml of DMF in order to obtain a 2 mg/ml solution of DSS do/d12. 10 µl of the antibody/antigen mix prepared previously were mixed with 1 µl of the solution of cross-linker d0/d12 prepared (2 mg/ml). The solution is incubated 180 minutes at room temperature in order to achieve the cross-linking reaction.

10 µl of the antigen (0.35 mg/mL) was mixed with 40 µl of ammonium bicarbonate (25 mM, pH 8.3). After mixing 2 µl of DTT (500 mM) is added to the solution. The mixture is then incubated 1 hour at 55° C. After incubation, 2 µl of iodioacetamide (1M) is added before 1 hour of incubation at room temperature in a dark room. After incubation, the solution is diluted 1/5 by adding 120 µl of the buffer used for the proteolysis.

145 µl of the reduced/alkyled antigen was mixed with 0.7 µl of trypsin (Roche Diagnostic) at ratio 1/100. The proteolytic mixture was incubated overnight at 37° C.

145 µl of the reduced/alkyled antigen was mixed with 0.35 µl of chymotrypsin (Roche Diagnostic) at ratio 1/200. The proteolytic mixture was incubated overnight at 25° C.

145 µl of the reduced/alkylated antigen was mixed with 0.35 µl of ASP-N (Roche Diagnostic) at ratio 1/200. The proteolytic mixture was incubated overnight at 37° C.

145 µl of the reduced/alkylated antigen was mixed with 0.70 µl of elastase (Roche Diagnostic) at ratio 1/100. The proteolytic mixture was incubated overnight at 37° C.

145 µl of the reduced/alkylated antigen was mixed with 1.40 µl of thermolysin (Roche Diagnostic) at ratio 1/50. The proteolytic mixture was incubated overnight at 70° C.

The cross-linker peptides were analyzed using Xquest version 2.0 and Stavrox 2.1. software.

Antibody Anti-HNL MAB1

After cross-linking, the peptides generated by multi-enzymatic proteolysis are covering 95% of the total antigen sequence.

Using the anti-HNL MAB1 hybridomas provided a cDNA sequencing has been performed with the following result:

```
Light Chain Variable region:
DIVMTQTPATLSVTPGDSVSLSCRASQSIITDLHWYQQRSHESPRLLIKS

ASQSISGIPSRFSGSGSGTDFTLTINSVETEDFGMYFCQQSNSWPLTFGA

GTKLELKRADAAPTVS

Heavy Chain Variable region:
VQLQESGPDLVAPSQSLSITCTVSGFSLSSYGVHWVRQPPGKGLEWLIVM

WSDGSTTSNSALKSRLSISKDNSKSQVFLKVNSLQSDDTAIYYCARHYGY

FTMDYWGQGTSVTVSS
```

Using chemical cross-linking, High-Mass MALDI mass spectrometry and nLC-Orbitrap mass spectrometry the interaction interface between the antigen HNL and the monoclonal antibody Anti-HNL MAB 1 was characterized. The epitope of this monoclonal antibody includes the following amino acids on HNL antigen: 144; 145; 154. On the antibody, the paratope includes the following amino acids: Heavy chain: 80; 86.

Antibody Anti-HNL MAB2

After cross-linking, peptides generated by multi-enzymatic proteolysis are covering 95% of the total antigen sequence. Using the anti-HNL MAB2 hybridomas provided a cDNA sequencing has been performed with the following result:

```
Light Chain Variable region:
DIVLTQSTSSLSVSLGDRVTINCRASQDISNYLNWYQEKPDGTVKLLIYF

TSRLHSGVPSRFSGSGSGTDYSLTITNLEQEDIATYFCQQGNTLPWTFGG

GTKLEIKRADAAPTV

Heavy Chain Variable region:
EVQLEESGPGLVAPSQSLSITCTISGFSLTSYGIHWLRQPPGKDLEWLVV

IWGDGSTTSNSALKSRLSISKDNSKSQVFFKMSGLQTDDTAIYYCARHRY

SDYHAMDYWGPGTSVTVS
```

Using chemical cross-linking, High-Mass MALDI mass spectrometry and nLC-Orbitrap mass spectrometry the interaction interface between the antigen HNL and the monoclonal antibody Anti-HNL MAB2 was characterized. The analysis indicates that the epitope of this monoclonal antibody includes the following amino acids on HNL antigen: 83; 88; 145; 154. On the antibody, the paratope includes the following amino acids: Heavy chain: 76; Light Chain: 114.

Antibody Anti-HNL MAB3

After cross-linking, the peptides generated by multi-enzymatic proteolysis are covering 95% of the total antigen sequence. Using the anti-HNL MAB3 hybridomas provided a cDNA sequencing has been performed with the following result:

```
Light Chain Variable region:
DIVLTQTTSSLSVSLGDRVTINCRASQDISNYLNWYQEKPDGTVKLLIYF

TSRLHSGVPSRFSGSGSGTDYSLTITNLEQEDIATYFCQQGNTLPWTFGG

GTKLEIKRADAAPTV

Heavy Chain Variable region:
EVKLQESGPGLVAPSQSLSITCTISGFSLTSYGIHWLRQPPGKDLEWLVV

IWGDGSTTSNSALKSRLSISKDNSKSQVFFKMSGLQTDDTAIYYCARHRY

SDYHAMDYWGPGTSVTVSS
```

Using chemical cross-linking, High-Mass MALDI mass spectrometry and nLC-Orbitrap mass spectrometry the interaction interface between the antigen HNL and the monoclonal antibody Anti-HNL MAB3 was characterized. The analysis indicates that the epitope of this monoclonal antibody includes the following amino acids on HNL antigen: 145; 154. On the antibody, the paratope includes the following amino acids: Light chain: 74; 76; 85.

2. Analysis of Clinical Samples Using Anti-HNL Antibodies

The high discriminatory power of HNL is most accentuated with measurements in serum and not with EDTA-plasma, which seems to suggest that the neutrophils in the test tube ex vivo continue to release their HNL upon serum preparation. This release activity reflects the state of activation of the neutrophils that was induced by the bacterial challenge but not by viruses. To be useful in the emergency department or in the doctor's office the total assay time from blood draw to result of any biomarker should be short i.e. <15-20 minutes, which is the philosophy behind the development of point-of-care (POC) assays. Such requirements are quite difficult with serum measurements of HNL, since, as indicated above, this requires a rather long pre-activation of the neutrophils. The possibility that activation of the neutrophils in the blood by the well-established neutrophil activator tri-peptide fMLP circumvent the problem was tested. The neutrophil activator is used to mimic the neutrophil activation occurring during whole blood coagulation and replaces the requirement to measure HNL in serum after a prolonged incubation.

In this example blood was collected from a large cohort of patients with signs of acute infection to compare the diagnostic performance of HNL concentrations in whole blood after activation with fMLP with the diagnostic performance of HNL in non-activated plasma. In addition the diagnostic performance of HNL test using this principle was compared with the diagnostic performance of contemporary tests such as blood neutrophil counts, CRP, the expression on neutrophils of the IgG1-receptor CD64 and procalcitonin.

Activation of Neutrophils by fMLP

Figure 2:
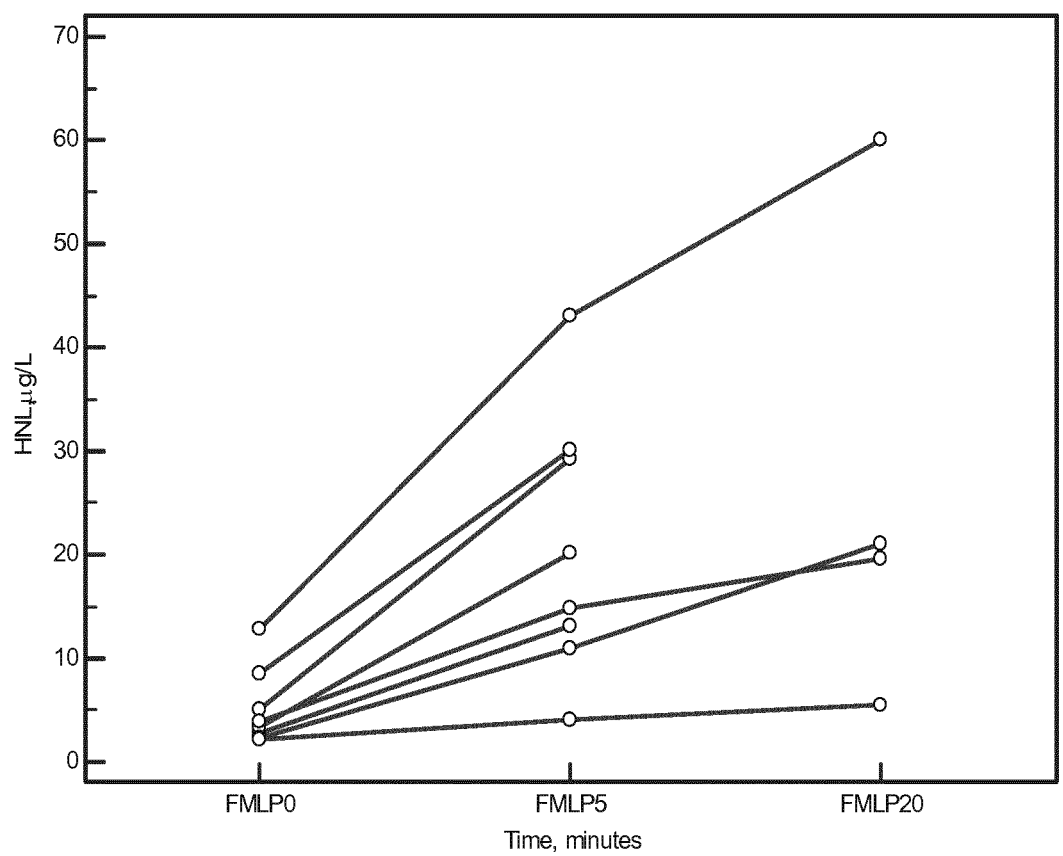
FIG. 2 shows the results of activation experiments with neutrophils purified from blood of patients and healthy controls using fMLP. Neutrophils were exposed to various concentrations of fMLP and incubated for 15 min at 37° C. and subsequently centrifuged and the supernatant assayed for the presence of HNL. The optimal concentration for the release of fMLP was found to be $5 \times 10^{-8}$ mol/L. In order to study the kinetics of release of HNL, purified cells were incubated for different lengths of time. Significant release was seen after 5 min of incubation and increased further by prolonged incubation.

Neutrophils purified from blood of patients and normal were exposed to various concentrations of fMLP and incubated for 15 min at 37° C. and subsequently centrifuged and the supernatant assayed for the presence of HNL. The optimal concentration for the release of fMLP was found to be $5 \times 10^{-8}$ mol/L. In order to study the kinetics of release of HNL, purified cells were incubated for different lengths of time. Significant release was seen after 5 min of incubation and increased further by prolonged incubation (FIG. 2).

Figure 3:
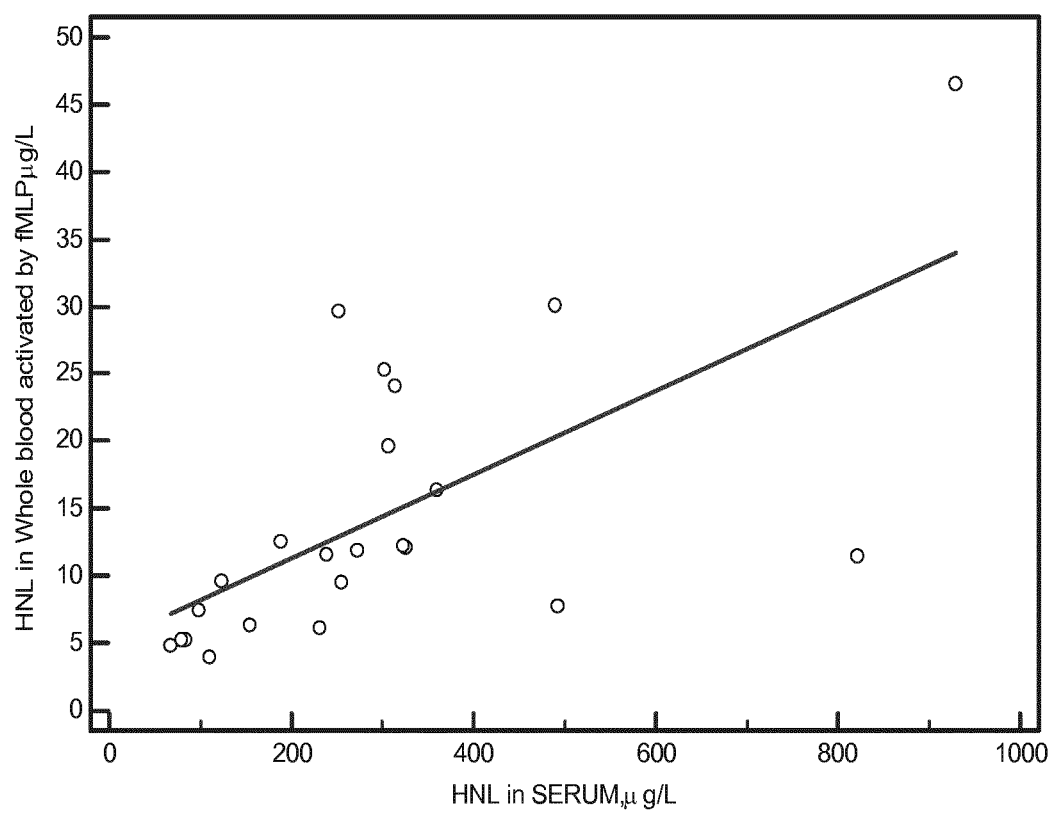
FIG. 3 shows tests regarding the release propensity of HNL through neutrophils after incubation with fMLP. In whole blood after coagulation, the release of HNL from neutrophils purified from XX patients with acute infections and YY healthy subjects was compared to the serum HNL concentrations of the respective subjects. A significant and linear correlation (r=0.743, p=0.002) was obtained between the supernatant and serum concentrations of HNL.

In order to test the possibility that the release propensity of neutrophils after incubation with fMLP reflected the release of HNL in whole blood after coagulation, the release of HNL from neutrophils purified from 23 patients with acute infections and 20 healthy subjects was compared to the serum HNL concentrations of the respective subjects. As can be seen from FIG. 3 a significant and linear correlation (r=0.743, p=0.002) was obtained between the supernatant and serum concentrations of HNL.

Clinical Results

Heparinized whole blood and EDTA-plasma were collected from 600 patients with symptoms of acute infection and from 144 apparently non-infected healthy subjects. Without knowledge of the investigated biomarkers (HNL, PCT and CD64 expression on blood neutrophils) results the infected patients were classified on clinical grounds as having a bacterial or viral cause of the disease. This classification included the knowledge of the concentrations of CRP and white blood cells and differentials. 240 patients were classified as having bacteria or virus as the likely cause of their infections and 325 patients were judged to have a possible or uncertain cause of their infections. 35 patients had mycoplasma as their cause of infection. In the patients with a likely cause of their infections, the infection was confirmed by objective tests such as bacterial culture and/or PCR and/or other objective tests. Also CRP and white blood cell counts were included in the diagnosis. This latter group of patients, without those having a mycoplasma infection, constituted altogether 384 subjects (healthy: 144, bacterial infections: 185, viral infections: 55) and was the group used in this report to examine the diagnostic performance of the biomarkers.

Figure 4:
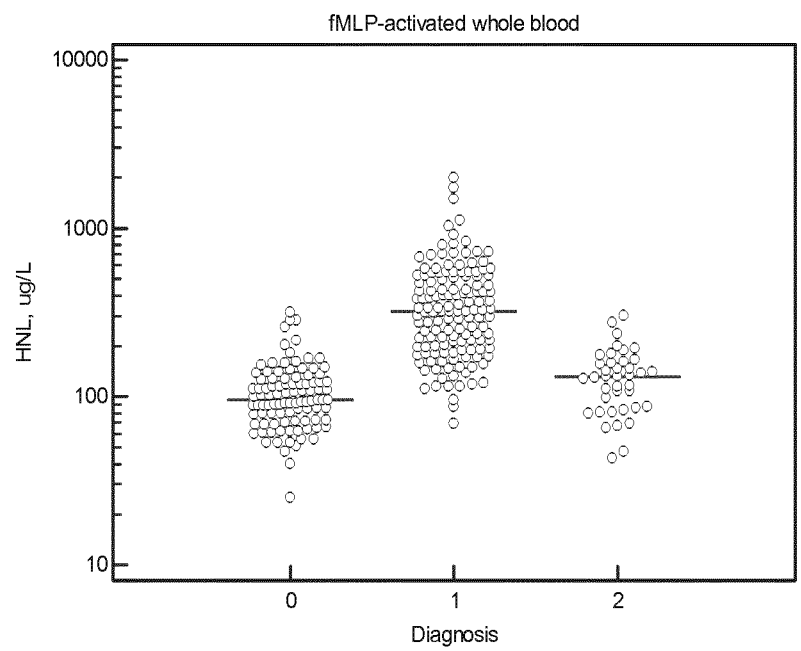
FIGS. 4a and b show the HNL concentrations in whole blood after fMLP activation for 20 min at 37° C. and in EDTA-plasma. HNL concentrations in fMLP-activated whole blood of healthy subjects (geometric mean 98 µg/L, 95% CI 90-107, µg/L) are significantly lower than concentrations measured in patients with bacterial (geometric mean 337 µg/L, 95% CI 300-379 µg/L) (p<0.0001) and patients with viral infections (geometric mean 117 µg/L, 95% CI 101-136 µg/L) (p<0.05).
Figure 4:
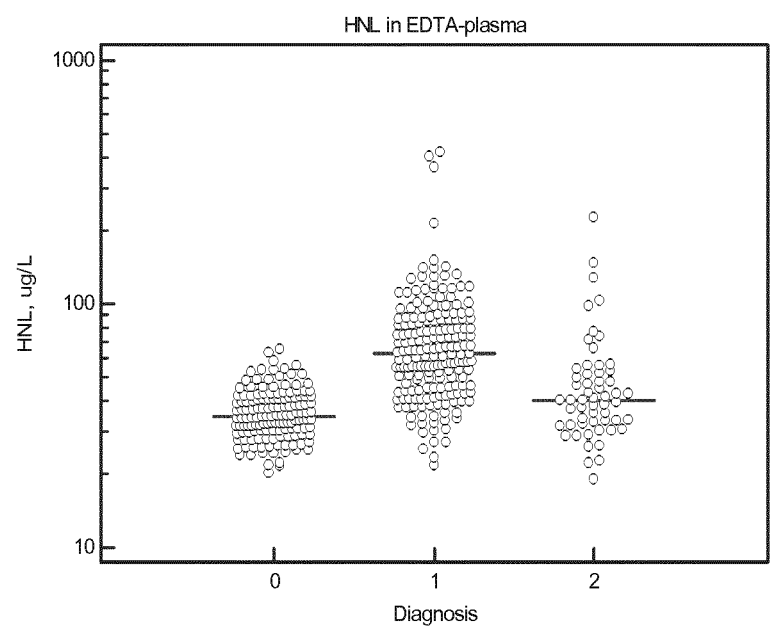

The diagnostic performance of HNL for the diagnosis of acute bacterial infection In FIGS. 4a and b the HNL concentrations in whole blood after fMLP activation for 20 min at 37° C. and in EDTA-plasma are shown. As compared to HNL concentrations in fMLP-activated whole blood of healthy subjects (geometric mean 98 µg/L, 95% CI 90-107, µg/L), the concentrations in patients with bacterial (geometric mean 337 µg/L, 95% CI 300-379 µg/L) (p<0.0001) and viral infections (geometric mean 117 µg/L, 95% CI 101-136 µg/L) (p<0.05) were significantly raised.

The concentrations of HNL in plasma of healthy subjects were 35 µg/L (geometric mean, 95% CI 34-36 µg/L) with significantly higher concentrations in patients with bacterial infections, 64 µg/L (geometric mean, 95% CI 60-69) (p<0.0001) and in patients with viral infections, 43 µg/L (geometric mean 95% CI 38-49) (p=0.0001). It is apparent that the overlap between healthy and bacterial is greater with EDTA-plasma. On average the additional amounts of HNL released from the neutrophils in whole blood activated by fMLP were 2.8-fold for healthy subjects, 5.3-fold for patients with bacterial infections and 2.7-fold for those with viral infections. Thus, no additional release of HNL over healthy subjects was seen with fMLP-activated whole blood.

Figure 5:
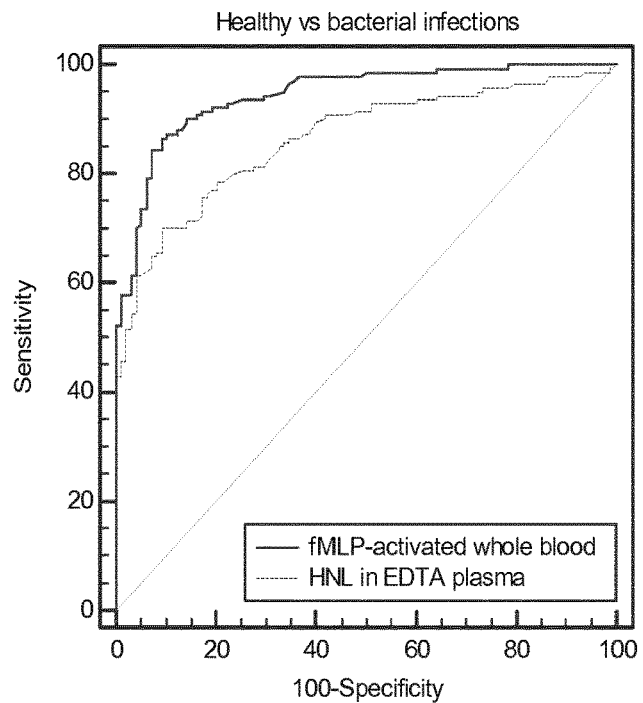
FIGS. 5a and b show the diagnostic performances of the two HNL assays i.e. in fMLP-activated whole blood and in EDTA-plasma. The distinction between healthy non-infected subjects and those with confirmed bacterial infection is shown by means of receiver operating characteristics (ROC) curves. The area under the curve (AUC) for the HNL test on fMLP-activated whole blood was 0.95 (95% 0.91-0.97) as compared to 0.88 (95% CI 0.84-0.91), p=0.0003 for HNL test on EDTA-plasma. For the fMLP-activated whole blood, the negative predictive value (NPV) at 125 µg/L HNL was 90% (95% CI 82-96%) and the positive value 83% (95% CI 77-89%). For EDTA-plasma at the HNL concentration of 40 µg/L the NPV was 86% (95% CI72-95%) and the PPV 63% (95% CI 57-69%). In the distinction between bacterial and viral infections the AUC for fMLP-activated whole blood was 0.92 (95% CI 0.87-0.96) and for EDTA-plasma 0.79 (95% CI 0.71-0.85), p=0.0006. At a concentration of 110 µg/L the NPV was 93% (95% CI 68-100%) and the PPV 85% (77-90%) for fMLP-activated whole blood. Corresponding figures for HNL at the concentration of 40 µg/L in EDTA-plasma were NPV 52% (95% CI 37-67%) and PPV 85% (95% CI 78-90%). The NPV did not exceed 60% at any concentration of HNL in EDTA-plasma. Thus, the clinical performance of HNL in fMLP-activated whole blood was superior to HNL in EDTA-plasma both in the distinction between healthy subjects and bacterial infections and in the distinction between bacterial and viral infections.
Figure 5:
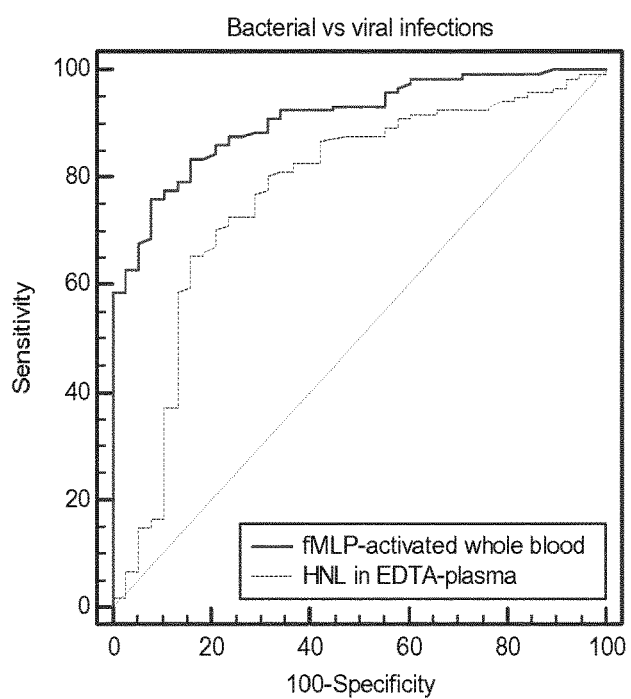
Figure 6:
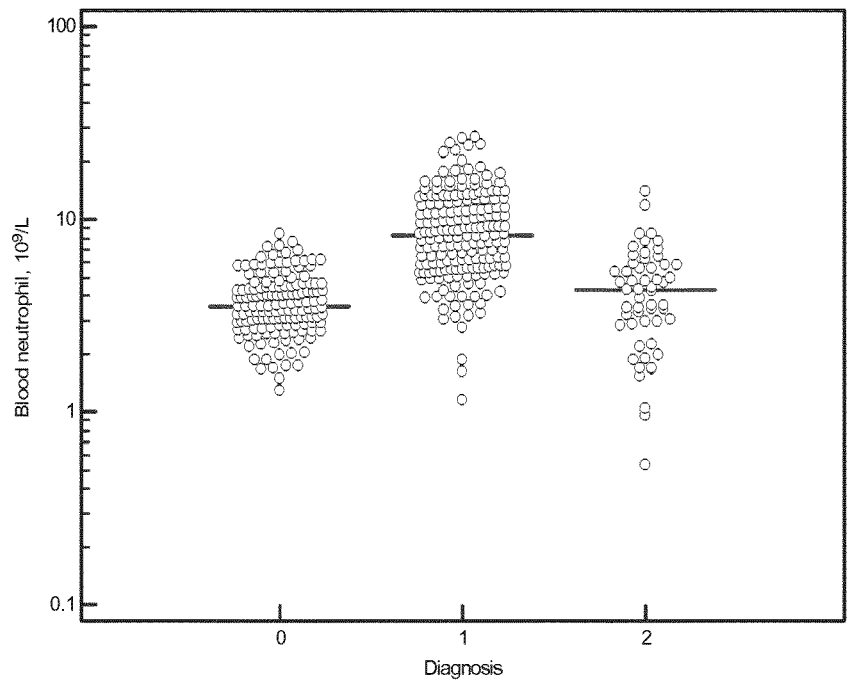
FIGS. 6a-d show the distribution of the biomarkers CRP, blood neutrophil counts, CD64 expression on blood neutrophils and procalcitonin in the studied populations. With the exception of neutrophil counts all other biomarkers were significantly raised in both bacterial and viral infections in comparisons to healthy subjects (p<0.0001).
Figure 6:
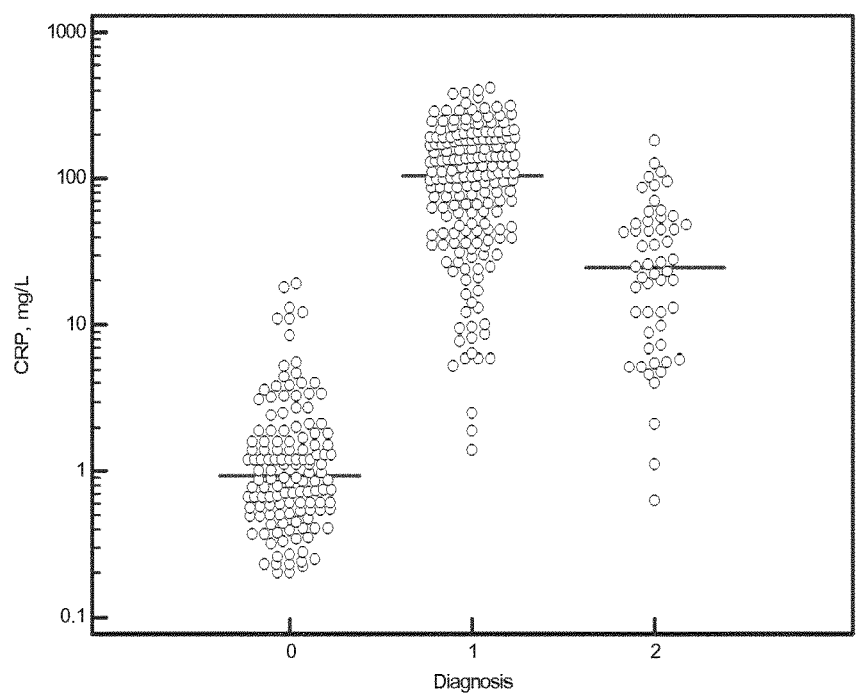
Figure 6:
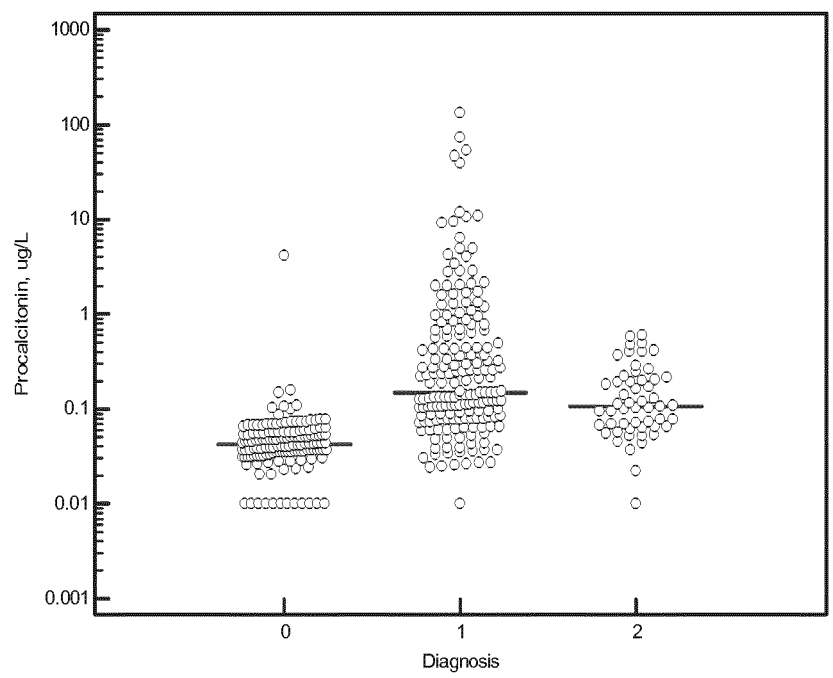
Figure 6:
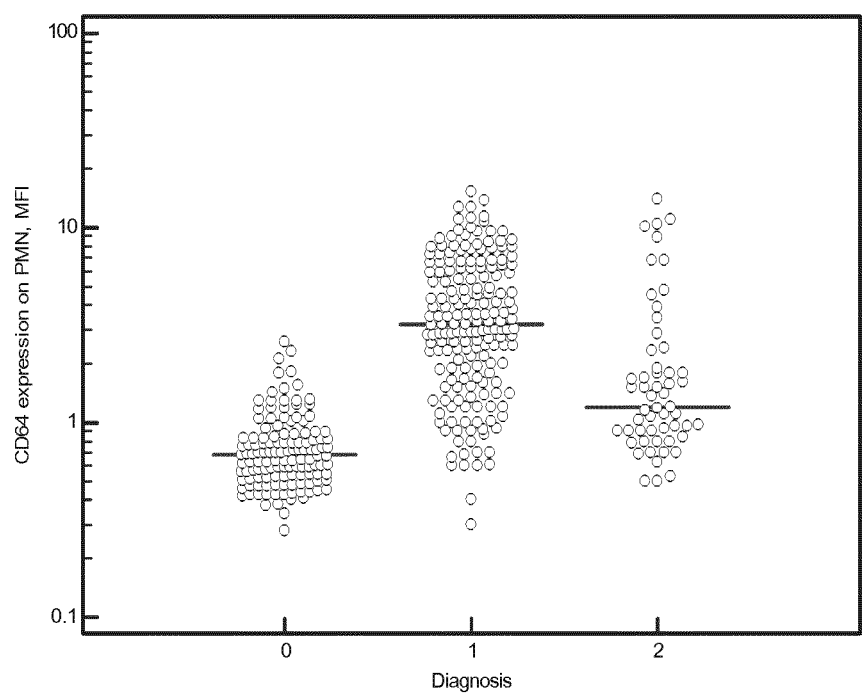
Figure 7:
FIG. 7 shows an HNL dimer. The HNL dimer is stabilized via a cysteine bridge indicated in black between the two HNL monomer structures. The regions involved in the antibody antigen binding are indicated in black (left and right hand of the figure).

FIGS. 5a and b show the diagnostic performances of the two HNL assays i.e. in fMLP-activated whole blood and in EDTA-plasma. In FIG. 5 a the distinction between healthy non-infected subjects and those with confirmed bacterial infection are shown by means of receiver operating characteristics (ROC) curves. The area under the curve (AUC) for the HNL test on fMLP-activated whole blood was 0.95 (95% 0.91-0.97) as compared to 0.88 (95% CI 0.84-0.91), p=0.0003 for HNL test on EDTA-plasma. For the fMLP-activated whole blood, the negative predictive value (NPV) at 125 µg/L HNL was 90% (95% CI 82-96%) and the positive value 83% (95% CI 77-89%). For EDTA-plasma at the HNL concentration of 40 µg/L the NPV was 86% (95% CI72-95%) and the PPV 63% (95% CI 57-69%). In the distinction between bacterial and viral infections the AUC for fMLP-activated whole blood was 0.92 (95% CI 0.87-0.96) and for EDTA-plasma 0.79 (95% CI 0.71-0.85), p=0.0006. At the concentration of 110 µg/L the NPV was 93% (95% CI 68-100%) and the PPV 85% (77-90%) for fMLP-activated whole blood. Corresponding figures for HNL at the concentration of 40 µg/L in EDTA-plasma were NPV 52% (95% CI 37-67%) and PPV 85% (95% CI 78-90%). The NPV did not exceed 60% at any concentration of HNL in EDTA-plasma. Thus, the clinical performance of HNL in fMLP-activated whole blood was superior to HNL in EDTA-plasma both in the distinction between healthy subjects and bacterial infections and in the distinction between bacterial and viral infections.

Diagnostic performance of CRP, blood neutrophil counts, CD64 expression on neutrophils and procalcitonin for the diagnosis of acute bacterial infection FIGS. 6a-d show the distribution of the biomarkers CRP, blood neutrophil counts, CD64 expression on blood neutrophils and procalcitonin in the studied populations. With the exception of neutrophil counts all other biomarkers were significantly raised in both bacterial and viral infections in comparisons to healthy subjects (p<0.0001). The biomarkers were all significantly higher in bacterial vs viral infections (p<0.0001). The mean concentrations are shown in table 1.

TABLE 1

Concentrations and expressions of four biomarkers.

| | CRP mg/L | Blood neutrophil count $10^9$/L | CD64-PMN, MFI | Procalcitonin µg/L |
|---|---|---|---|---|
| Healthy | 1.06 | 3.59 | 0.70 | 0.042 |
| | (0.90-1.26) | (3.38-3.81) | (0.65-0.75) | (0.038-0.047) |
| Bacterial infections | 81.0 | 8.21 | 3.13 | 0.262 |
| | (68.8-95.4) | (7.60-8.88) | (2.78-3.52) | (0.205-0.335) |
| Viral infections | 20.7 | 3.82 | 1.59 | 0.117 |
| | (14.7-29.0) | (3.23-4.53) | (1.26-2.01) | (0.093-0.149) |

The AUCs are given in table 2. In the distinction between healthy and bacterial infections four biomarkers showed AUCs >90 and these were CRP, HNL in fMLP-activated whole blood, the expression of CD64 on blood neutrophils and blood neutrophil counts. The AUC of HNL in fMLP activated whole blood was significantly higher than the AUCs of HNL in EDTA-plasma (p<0.001) and procalcitonin (p<0.05) and the AUC of the expression of CD64 on neutrophils was higher than EDTA-plasma HNL (p=0.002), but not significantly different from PCT (p=0.06). CRP showed the highest AUC, but statistics was not calculated because of the inherent risk of bias.

In the distinction between bacterial and viral infections only the AUC of fMLP-activated whole blood was >90%. This was significantly different from EDTA-plasma HNL (p=0.003), CD64 expression on neutrophils and procalcitonin (p<0.0001 for both comparisons). The AUC of EDTA-plasma HNL was significantly higher than that of procalcitonin (p=0.01).

TABLE 2

Areas under the ROC curves of all studied biomarkers

| | AUC (95% CI) |
|---|---|
| Healthy vs bacteria | |
| HNL, fMLP-activated whole blood | 0.95 (0.91-0.97) |
| Neutrophil counts | 0.92 (0.88-0.95) |
| P-HNL | 0.85 (0.79-0.89) |
| CRP | 0.99 (0.98-1.00) |
| CD64 expression on PMN | 0.94 (0.90-0.97) |
| Procalcitonin | 0.89 (0.84-0.93) |
| Bacteria vs virus | |
| HNL, fMLP-activated whole blood | 0.92 (0.87-0.96) |
| Neutrophil counts | 0.87 (0.81-0.92) |
| P-HNL | 0.79 (0.71-0.85) |
| CRP | 0.79 (0.72-0.86) |
| CD64 expression on PMN | 0.69 (0.61-0.77) |
| Procalcitonin | 0.65 (0.57-0.73) |

The invention claimed is:

1. A binding agent configured to specifically bind to a polypeptide epitope of human neutrophil lipocalin (HNL) with a binding affinity,
   wherein the binding agent comprises six murine complementarity-determining regions (CDRs),
   wherein each of the CDRs are configured to bind to amino acids 141 to 156 of the human polypeptide epitope of HNL as defined in SEQ ID NO: 1,
   wherein the HNL epitope is specifically bound,
   wherein the binding affinity is at least 75% or higher compared with a binding specificity achieved with the CDRs, wherein the CDRs are depicted in SEQ ID Nos: 8 to 13, 14 to 19, or 20 to 25,
   wherein the binding agent comprises a heavy chain variable region and a light chain variable region,
   wherein the heavy chain variable region comprises a first set of the murine CDRs, the first set comprising:
   a first heavy chain CDR (CDRH1), wherein CDRH1 is SEQ ID NO: 11;
   a second heavy chain CDR (CDRH2), wherein CDRH2 is SEQ ID NO: 12; and
   a third heavy chain CDR (CDRH3), wherein CDRH3 is SEQ ID NO: 13,
   wherein the light chain variable region comprises a second set of the murine CDRs, the second set comprising:
   a first light chain CDR (CDRL1), wherein CDRL1 SEQ ID NO: 8;
   a second light chain CDR (CDRL2), wherein CDRL2 SEQ ID NO: 9; and
   a third light chain CDR (CDRL3), wherein CDRL3 SEQ ID NO: 10.

2. The binding agent according to claim 1,
   wherein the binding agent has a heavy chain comprising the first set,
   wherein the heavy chain comprises a heavy chain variable region sequence selected from the group consisting of sequences depicted in SEQ ID NO: 3,
   wherein the binding agent has a light chain comprising the second set,
   wherein the light chain comprises a light chain variable region sequence selected from the group consisting of sequences depicted in SEQ ID NO: 2.

3. A diagnostic composition comprising a binding agent as defined in claim 1.

4. A diagnostic kit comprising containers comprising a binding agent as defined in in claim 1, and at least one of instructions for use, buffers, and a device, wherein the device is arranged for blood, plasma, serum, urine, cerebrospinal fluid (CSF), bone marrow, saliva, or sputum sample analysis.

5. The binding agent according to claim 1, wherein the binding agent is a monoclonal antibody, a chimeric antibody, or a humanized antibody.

6. The binding agent according to claim 1,
   wherein the binding agent has a heavy chain comprising the first set of,
   wherein the heavy chain comprises a sequence depicted in SEQ ID NO: 3.

7. The binding agent according to claim 1,
   wherein the binding agent has a light chain comprising the second set,
   wherein the light chain comprises a sequence depicted in SEQ ID NO: 2.

* * * * *

SEQUENCE LISTING

<160> NUMBER OF SEQ ID NOS: 26

<210> SEQ ID NO 1
<211> LENGTH: 198
<212> TYPE: PRT
<213> ORGANISM: Homo sapiens

<400> SEQUENCE: 1

Met Pro Leu Gly Leu Leu Trp Leu Gly Leu Ala Leu Leu Gly Ala Leu
1               5                   10                  15

His Ala Gln Ala Gln Asp Ser Thr Ser Asp Leu Ile Pro Ala Pro Pro
            20                  25                  30

Leu Ser Lys Val Pro Leu Gln Gln Asn Phe Gln Asp Asn Gln Phe Gln
        35                  40                  45

Gly Lys Trp Tyr Val Val Gly Leu Ala Gly Asn Ala Ile Leu Arg Glu
    50                  55                  60

Asp Lys Asp Pro Gln Lys Met Tyr Ala Thr Ile Tyr Glu Leu Lys Glu
65                  70                  75                  80

Asp Lys Ser Tyr Asn Val Thr Ser Val Leu Phe Arg Lys Lys Lys Cys
                85                  90                  95

Asp Tyr Trp Ile Arg Thr Phe Val Pro Gly Cys Gln Pro Gly Glu Phe
            100                 105                 110

Thr Leu Gly Asn Ile Lys Ser Tyr Pro Gly Leu Thr Ser Tyr Leu Val
        115                 120                 125

Arg Val Val Ser Thr Asn Tyr Asn Gln His Ala Met Val Phe Phe Lys
    130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
            180                 185                 190

Asp Gln Cys Ile Asp Gly
            195

<210> SEQ ID NO 2
<211> LENGTH: 116
<212> TYPE: PRT

<213> ORGANISM: Mus musculus

<400> SEQUENCE: 2

Asp Ile Val Met Thr Gln Thr Pro Ala Thr Leu Ser Val Thr Pro Gly
1               5                   10                  15

Asp Ser Val Ser Leu Ser Cys Arg Ala Ser Gln Ser Ile Ile Thr Asp
            20                  25                  30

Leu His Trp Tyr Gln Gln Arg Ser His Glu Ser Pro Arg Leu Leu Ile
        35                  40                  45

Lys Ser Ala Ser Gln Ser Ile Ser Gly Ile Pro Ser Arg Phe Ser Gly
    50                  55                  60

Ser Gly Ser Gly Thr Asp Phe Thr Leu Thr Ile Asn Ser Val Glu Thr
65                  70                  75                  80

Glu Asp Phe Gly Met Tyr Phe Cys Gln Gln Ser Asn Ser Trp Pro Leu
                85                  90                  95

Thr Phe Gly Ala Gly Thr Lys Leu Glu Leu Lys Arg Ala Asp Ala Ala
            100                 105                 110

Pro Thr Val Ser
        115

<210> SEQ ID NO 3
<211> LENGTH: 116
<212> TYPE: PRT
<213> ORGANISM: Mus musculus

<400> SEQUENCE: 3

Val Gln Leu Gln Glu Ser Gly Pro Asp Leu Val Ala Pro Ser Gln Ser
1               5                   10                  15

Leu Ser Ile Thr Cys Thr Val Ser Gly Phe Ser Leu Ser Ser Tyr Gly
            20                  25                  30

Val His Trp Val Arg Gln Pro Pro Gly Lys Gly Leu Glu Trp Leu Ile
        35                  40                  45

Val Met Trp Ser Asp Gly Ser Thr Thr Ser Asn Ser Ala Leu Lys Ser
    50                  55                  60

Arg Leu Ser Ile Ser Lys Asp Asn Ser Lys Ser Gln Val Phe Leu Lys
65                  70                  75                  80

Val Asn Ser Leu Gln Ser Asp Asp Thr Ala Ile Tyr Tyr Cys Ala Arg
                85                  90                  95

His Tyr Gly Tyr Phe Thr Met Asp Tyr Trp Gly Gln Gly Thr Ser Val
            100                 105                 110

Thr Val Ser Ser
        115

<210> SEQ ID NO 4
<211> LENGTH: 115
<212> TYPE: PRT
<213> ORGANISM: Mus musculus

<400> SEQUENCE: 4

Asp Ile Val Leu Thr Gln Ser Thr Ser Ser Leu Ser Val Ser Leu Gly
1               5                   10                  15

Asp Arg Val Thr Ile Asn Cys Arg Ala Ser Gln Asp Ile Ser Asn Tyr
            20                  25                  30

Leu Asn Trp Tyr Gln Glu Lys Pro Asp Gly Thr Val Lys Leu Leu Ile
        35                  40                  45

Tyr Phe Thr Ser Arg Leu His Ser Gly Val Pro Ser Arg Phe Ser Gly
    50                  55                  60

```
Ser Gly Ser Gly Thr Asp Tyr Ser Leu Thr Ile Thr Asn Leu Glu Gln
 65                  70                  75                  80

Glu Asp Ile Ala Thr Tyr Phe Cys Gln Gln Gly Asn Thr Leu Pro Trp
                 85                  90                  95

Thr Phe Gly Gly Gly Thr Lys Leu Glu Ile Lys Arg Ala Asp Ala Ala
            100                 105                 110

Pro Thr Val
        115

<210> SEQ ID NO 5
<211> LENGTH: 118
<212> TYPE: PRT
<213> ORGANISM: Mus musculus

<400> SEQUENCE: 5

Glu Val Gln Leu Glu Glu Ser Gly Pro Gly Leu Val Ala Pro Ser Gln
  1               5                  10                  15

Ser Leu Ser Ile Thr Cys Thr Ile Ser Gly Phe Ser Leu Thr Ser Tyr
                 20                  25                  30

Gly Ile His Trp Leu Arg Gln Pro Pro Gly Lys Asp Leu Glu Trp Leu
             35                  40                  45

Val Val Ile Trp Gly Asp Gly Ser Thr Thr Ser Asn Ser Ala Leu Lys
 50                  55                  60

Ser Arg Leu Ser Ile Ser Lys Asp Asn Ser Lys Ser Gln Val Phe Phe
 65                  70                  75                  80

Lys Met Ser Gly Leu Gln Thr Asp Asp Thr Ala Ile Tyr Tyr Cys Ala
                 85                  90                  95

Arg His Arg Tyr Ser Asp Tyr His Ala Met Asp Tyr Trp Gly Pro Gly
            100                 105                 110

Thr Ser Val Thr Val Ser
        115

<210> SEQ ID NO 6
<211> LENGTH: 115
<212> TYPE: PRT
<213> ORGANISM: Mus musculus

<400> SEQUENCE: 6

Asp Ile Val Leu Thr Gln Thr Thr Ser Ser Leu Ser Val Ser Leu Gly
  1               5                  10                  15

Asp Arg Val Thr Ile Asn Cys Arg Ala Ser Gln Asp Ile Ser Asn Tyr
                 20                  25                  30

Leu Asn Trp Tyr Gln Glu Lys Pro Asp Gly Thr Val Lys Leu Leu Ile
             35                  40                  45

Tyr Phe Thr Ser Arg Leu His Ser Gly Val Pro Ser Arg Phe Ser Gly
 50                  55                  60

Ser Gly Ser Gly Thr Asp Tyr Ser Leu Thr Ile Thr Asn Leu Glu Gln
 65                  70                  75                  80

Glu Asp Ile Ala Thr Tyr Phe Cys Gln Gln Gly Asn Thr Leu Pro Trp
                 85                  90                  95

Thr Phe Gly Gly Gly Thr Lys Leu Glu Ile Lys Arg Ala Asp Ala Ala
            100                 105                 110

Pro Thr Val
        115

<210> SEQ ID NO 7
```

```
<211> LENGTH: 119
<212> TYPE: PRT
<213> ORGANISM: Mus musculus

<400> SEQUENCE: 7

Glu Val Lys Leu Gln Glu Ser Gly Pro Gly Leu Val Ala Pro Ser Gln
1               5                   10                  15

Ser Leu Ser Ile Thr Cys Thr Ile Ser Gly Phe Ser Leu Thr Ser Tyr
            20                  25                  30

Gly Ile His Trp Leu Arg Gln Pro Pro Gly Lys Asp Leu Glu Trp Leu
        35                  40                  45

Val Val Ile Trp Gly Asp Gly Ser Thr Thr Ser Asn Ser Ala Leu Lys
50                  55                  60

Ser Arg Leu Ser Ile Ser Lys Asp Asn Ser Lys Ser Gln Val Phe Phe
65                  70                  75                  80

Lys Met Ser Gly Leu Gln Thr Asp Asp Thr Ala Ile Tyr Tyr Cys Ala
                85                  90                  95

Arg His Arg Tyr Ser Asp Tyr His Ala Met Asp Tyr Trp Gly Pro Gly
            100                 105                 110

Thr Ser Val Thr Val Ser Ser
        115

<210> SEQ ID NO 8
<211> LENGTH: 11
<212> TYPE: PRT
<213> ORGANISM: Mus musculus

<400> SEQUENCE: 8

Arg Ala Ser Gln Ser Ile Ile Thr Asp Leu His
1               5                   10

<210> SEQ ID NO 9
<211> LENGTH: 7
<212> TYPE: PRT
<213> ORGANISM: Mus musculus

<400> SEQUENCE: 9

Ser Ala Ser Gln Ser Ile Ser
1               5

<210> SEQ ID NO 10
<211> LENGTH: 9
<212> TYPE: PRT
<213> ORGANISM: Mus musculus

<400> SEQUENCE: 10

Gln Gln Ser Asn Ser Trp Pro Leu Thr
1               5

<210> SEQ ID NO 11
<211> LENGTH: 10
<212> TYPE: PRT
<213> ORGANISM: Mus musculus

<400> SEQUENCE: 11

Gly Phe Ser Leu Ser Ser Tyr Gly Val His
1               5                   10

<210> SEQ ID NO 12
<211> LENGTH: 16
<212> TYPE: PRT
<213> ORGANISM: Mus musculus
```

<400> SEQUENCE: 12

Val Met Trp Ser Asp Gly Ser Thr Thr Ser Asn Ser Ala Leu Lys Ser
1               5                   10                  15

<210> SEQ ID NO 13
<211> LENGTH: 9
<212> TYPE: PRT
<213> ORGANISM: Mus musculus

<400> SEQUENCE: 13

His Tyr Gly Tyr Phe Thr Met Asp Tyr
1               5

<210> SEQ ID NO 14
<211> LENGTH: 11
<212> TYPE: PRT
<213> ORGANISM: Mus musculus

<400> SEQUENCE: 14

Arg Ala Ser Gln Asp Ile Ser Asn Tyr Leu Asn
1               5                   10

<210> SEQ ID NO 15
<211> LENGTH: 7
<212> TYPE: PRT
<213> ORGANISM: Mus musculus

<400> SEQUENCE: 15

Phe Thr Ser Arg Leu His Ser
1               5

<210> SEQ ID NO 16
<211> LENGTH: 11
<212> TYPE: PRT
<213> ORGANISM: Mus musculus

<400> SEQUENCE: 16

His Arg Tyr Ser Asp Tyr His Ala Met Asp Tyr
1               5                   10

<210> SEQ ID NO 17
<211> LENGTH: 10
<212> TYPE: PRT
<213> ORGANISM: Mus musculus

<400> SEQUENCE: 17

Gly Phe Ser Leu Thr Ser Tyr Gly Ile His
1               5                   10

<210> SEQ ID NO 18
<211> LENGTH: 16
<212> TYPE: PRT
<213> ORGANISM: Mus musculus

<400> SEQUENCE: 18

Val Ile Trp Gly Asp Gly Ser Thr Thr Ser Asn Ser Ala Leu Lys Ser
1               5                   10                  15

<210> SEQ ID NO 19
<211> LENGTH: 11
<212> TYPE: PRT
<213> ORGANISM: Mus musculus

<400> SEQUENCE: 19

His Arg Tyr Ser Asp Tyr His Ala Met Asp Tyr
1               5                   10

<210> SEQ ID NO 20
<211> LENGTH: 11
<212> TYPE: PRT
<213> ORGANISM: Mus musculus

<400> SEQUENCE: 20

Arg Ala Ser Gln Asp Ile Ser Asn Tyr Leu Asn
1               5                   10

<210> SEQ ID NO 21
<211> LENGTH: 7
<212> TYPE: PRT
<213> ORGANISM: Mus musculus

<400> SEQUENCE: 21

Phe Thr Ser Arg Leu His Ser
1               5

<210> SEQ ID NO 22
<211> LENGTH: 9
<212> TYPE: PRT
<213> ORGANISM: Mus musculus

<400> SEQUENCE: 22

Gln Gln Gly Asn Thr Leu Pro Trp Thr
1               5

<210> SEQ ID NO 23
<211> LENGTH: 10
<212> TYPE: PRT
<213> ORGANISM: Mus musculus

<400> SEQUENCE: 23

Gly Phe Ser Leu Thr Ser Tyr Gly Ile His
1               5                   10

<210> SEQ ID NO 24
<211> LENGTH: 16
<212> TYPE: PRT
<213> ORGANISM: Mus musculus

<400> SEQUENCE: 24

Val Ile Trp Gly Asp Gly Ser Thr Thr Ser Asn Ser Ala Leu Lys Ser
1               5                   10                  15

<210> SEQ ID NO 25
<211> LENGTH: 11
<212> TYPE: PRT
<213> ORGANISM: Mus musculus

<400> SEQUENCE: 25

His Arg Tyr Ser Asp Tyr His Ala Met Asp Tyr
1               5                   10

<210> SEQ ID NO 26
<211> LENGTH: 72
<212> TYPE: PRT
<213> ORGANISM: Homo sapiens

<400> SEQUENCE: 26

Ser Tyr Asn Val Thr Ser Val Leu Phe Arg Lys Lys Lys Cys Asp Tyr

```
1               5                   10                  15
Trp Ile Arg Thr Phe Val Pro Gly Cys Gln Pro Gly Glu Phe Thr Leu
            20                  25                  30

Gly Asn Ile Lys Ser Tyr Pro Gly Leu Thr Ser Tyr Leu Val Arg Val
            35                  40                  45

Val Ser Thr Asn Tyr Asn Gln His Ala Met Val Phe Phe Lys Lys Val
        50                  55                  60

Ser Gln Asn Arg Glu Tyr Phe Lys
65                  70
```